US007427602B1

(12) United States Patent
Shea et al.

(10) Patent No.: US 7,427,602 B1
(45) Date of Patent: Sep. 23, 2008

(54) SUSTAINED DNA DELIVERY FROM STRUCTURAL MATRICES

(75) Inventors: Lonnie D. Shea, Evanston, IL (US); Jeffrey Bonadio, San Diego, CA (US); David J. Mooney, Ann Arbor, MI (US); Martin C. Peters, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/442,542

(22) Filed: Nov. 18, 1999

(51) Int. Cl.
*A61N 43/04* (2006.01)
*A61K 63/00* (2006.01)
*A61K 9/14* (2006.01)
*A61K 45/00* (2006.01)
*A61F 13/00* (2006.01)
*C12P 21/06* (2006.01)
*C12N 15/00* (2006.01)
*C12N 5/00* (2006.01)
*A61K 38/00* (2006.01)

(52) U.S. Cl. .................. 514/44; 424/93.1; 424/422; 424/484; 424/85.1; 435/69.1; 435/320.1; 435/325; 435/455; 514/2; 514/54

(58) Field of Classification Search ............... 435/69.1, 435/320.1, 325, 455; 424/93.1, 93.21; 514/44
See application file for complete search history.

(56) References Cited

U.S. PATENT DOCUMENTS

| | | | |
|---|---|---|---|
| 3,975,350 A | 8/1976 | Hudgin et al. | 260/30.4 |
| 4,871,384 A | 10/1989 | Kasuga | 65/30.1 |
| 4,933,185 A * | 6/1990 | Wheatley et al. | 424/461 |
| 5,514,378 A * | 5/1996 | Mikos et al. | 424/425 |
| 5,639,473 A * | 6/1997 | Grinstaff et al. | 424/450 |
| 5,763,416 A * | 6/1998 | Bonadio et al. | 514/44 |
| 5,785,965 A | 7/1998 | Pratt et al. | 424/93.21 |
| 5,792,751 A | 8/1998 | Ledley et al. | 514/44 |
| 5,942,496 A * | 8/1999 | Bonadio et al. | 514/44 |
| 5,965,125 A * | 10/1999 | Mineau-Hanschke | 424/93.21 |
| 6,033,719 A | 3/2000 | Keogh | 427/2.12 |
| 6,143,037 A | 11/2000 | Goldstein et al. | 623/66 |
| 6,187,329 B1 | 2/2001 | Agrawal et al. | 424/426 |
| 6,281,256 B1 * | 8/2001 | Harris et al. | 521/51 |
| 6,391,311 B1 | 5/2002 | Ferrara et al. | 424/198.1 |
| 6,423,085 B1 | 7/2002 | Murayama et al. | 606/200 |
| 6,537,567 B1 | 3/2003 | Niklason et al. | 424/423 |
| 6,541,022 B1 | 4/2003 | Murphy et al. | 424/422 |
| 6,642,363 B1 * | 11/2003 | Mooney et al. | 536/3 |
| 6,767,928 B1 | 7/2004 | Murphy et al. | 521/51 |
| 6,797,738 B2 * | 9/2004 | Harris et al. | 521/149 |

FOREIGN PATENT DOCUMENTS

EP 0 248 531 5/1987

OTHER PUBLICATIONS

Shapiro et al Biomaterials 18:583-590, 1997.*
Fang et al PNAS 03:5753-5758, 1996.*
Kawada et al FEBS Letts. 408;43-46, 1997.*
Connolly, "Bioelectronic Interfacing: Micro- and Nanofabrication Techniques for Generating Predetermined Molecular Arrays," *Tibtech*, 12:123-127, 1994.
James et al., "Small changes in polymer chemistry have a large effect on the bone-implant interface," *Biomaterials*, 20:2030-2212, 1999.
Li et al., "In Vitro Calcium Phosphate Formation on a Natural Composite Material, Bamboo," *Biomaterials*, 18:389-395, 1997.
Oliveira et al., "Surface modification tailors the characteristics of biomimetic coating nucleated on starch-based polymers," *Journal of Materials Science: Materials in Medicine*, 10:827-835, 1999.
Reis et al., "Treatments to induce the nucleation and growth of apatite-like layers on polymeric surface and foams," *Journal of Materials Science: Materials in Medicine*, 8:897-905, 1997.
Tanahashi and Matsuda, "Surface Functional Group Dependence on Apatite Formation on Self-Assembled Monolayers in a Simulated Body Fluid," *Journal Biomedical Materials Research*, 34:305-315, 1997.
Riessen et al., "Arterial Gene Transfer Using Pure DNA Applied Directly to a Hydrogel-Coated Angioplasty Balloon," *Human Gene Therapy*, 4:749-758, 1993.
Gunasekaran et al., "Mineralized Collages as a Substitute for Autograft Bone that can Deliver Bone Morphogenic Protein," *19th Ann. Meeting of the Society for Biomaterials*, Apr. 28-May 2, 1993.
Gunasekaran et al., "Role of Mineralized Collagen as an Osteoconductive Biomaterial," *19th Ann. Meeting of the Society for Biomaterials*, Apr. 28-May 2, 1993.
Abe, Kokubo and Yamamuro, "Apatite coating on ceramics, metals and polymers utilizing a biological process," *J. Mat. Sci.: Mat. Med.*, 1:233-238, 1990.
Bradt et al., "Biomimetic mineralization of collagen by combined fibril assembly and calcium phosphate formation," *Chem. Mater.*, 11:2694-2701, 1999.
Gao, Niklason and Langer, "Surface hydrolysis of poly (glycolic acid) meshes increases the seeding density of vascular smooth muscle cells," *J. Biomed. Mater. Res.*, 42(3):417-424, 1998.
Li, Bakker and van Blitterswijk, "The bone-bonding polymer polyactive® 80/20 induces hydroxycarbonate apatite formation in vitro," *J. Biomed. Mat. Res.*, 34:79-86, 1997.
Miyaji et al., "Bonelike apatite coating on organic polymers: Novel nucleation process using sodium silicate solution," *Biomaterials*, 20:913-919, 1999.

(Continued)

*Primary Examiner*—Sumesh Kaushal
(74) *Attorney, Agent, or Firm*—Marshall, Gerstein & Borun LLP

(57) ABSTRACT

Disclosed are particular 3-dimensional structural matrices containing nucleic acids, various fabrication processes and methods for the prolonged release of nucleic acids in various biological environments. The nucleic acid-matrix materials are created such that they maintain a defined space, allowing cellular migration, transfection and proliferation to occur in a controlled manner. The fabrication processes provide for both high incorporation efficiencies and control over the sustained nucleic acid release. The resultant nucleic acid-containing structural matrices are thus particularly useful in in vivo cell transfection and gene expression in the context of gene therapy.

34 Claims, 7 Drawing Sheets

OTHER PUBLICATIONS

Murphy, Kohn and Mooney, "Growth of continuous bonelike mineral within porous poly(lactide-co-glycolide) scaffolds in vitro," *J. Biomed. Mater. Res.*, 50(1):50-58, 2000.

Peters and Mooney, "Growth factor delivery from tissue engineering matrices: Inducing angiogenesis to enhance transplanted cell engraftment," In: *Controlled Drug Delivery: Designing Technologies for the Futute*, Park and Mrsny, Eds., Washington, D.C., American Chemical Society, Ch. 16, p. 157-166, 2000.

Shea et al., "DNA delivery from polymer matrices for tissue engineering," *Nature Biotechnology*, 17(6):551-554, 1999.

Sheridan et al., "Bioabsorbable polymer scaffolds for tissue engineering capable of sustained growth factor delivery," *Journal of Controlled Release*, 64:91-102, 2000.

Taguchi et al., "A study on hydroxyapatite formation on/in the hydroxyl groups-bearing nonionic hydrogels," *J. Biomater. Sci. Polymer Edn.*, 10(1):19-32, 1999.

Varma et al., "Porous calcium phosphate coating over phosphorylated chitosan film by a biomimetic method," *Biomaterials*, 20:879-884, 1999.

Wen et al., "Preparation of calcium phosphate coating on titanium implant materials by simple chemistry," *J. Biomed. Mater. Res.*, 41:227-236, 1998.

Zhang and Ma, "Porous poly(L-lactic acid)/apatite composites created by biomimetic process," *J. Biomed. Mater. Res.*, 45:285-293, 1999.

\* cited by examiner

SUSTAINED DNA DELIVERY FROM STRUCTURAL MATRICES

The U.S. Government owns rights in the present invention pursuant to Grant Numbers 1RO1DE13004, DE07057 and AR40673 from the National Institutes of Health.

The present application claims priority to U.S. application Ser. No. 09/310,802, filed May 12, 1999, now abandoned, which claims priority to second provisional application Ser. No. 60/109,054, filed Nov. 19, 1998 and to first provisional application Ser. No. 60/085,305, filed May 13, 1998; the entire specifications, claims and figures of which application and provisional applications are incorporated herein by reference without disclaimer.

Also specifically incorporated herein by reference without disclaimer are U.S. patent application Ser. No. 09/402,119, filed Sep. 20, 1999, now U.S. Pat. No. 6,281,256 which claims priority to PCT Application No. PCT/US98/06188 (WO 98/44027), filed Mar. 31, 1998, which designated the United States and which claims priority to U.S. Provisional Application Ser. No. 60/042,198, filed Mar. 31, 1997; and PCT Application No. PCT/US97/16890 (WO 98/12228), filed Sep. 19, 1997, which designates the United States and which claims priority to U.S. Provisional Application Ser. Nos. 60/026,362, 60/026,467 and 60/041,565, filed Sep. 19, 1996, Sep. 19, 1996 and Mar. 21, 1997, respectively. Applicants expressly reserve the right to claim priority to one or more of the foregoing incorporated applications.

BACKGROUND OF THE INVENTION

1. Field of the Invention

The present invention generally relates to the fields of porous polymer materials and their biological uses. More specifically, it concerns particular 3-dimensional structural matrices containing nucleic acids, which provide nucleic acids with prolonged bioavailability and control over cellular migration, transfection and proliferation. The invention thus provides defined nucleic acid-matrix materials and methods of making and using such compositions, e.g., in cell transfection, gene expression and in vivo gene therapy, as exemplified by uses in wound healing and bone repair.

2. Description of Related Art

Lost or deficient tissue function leads to millions of surgical procedures each year and a loss to the western economies of hundreds of billions of dollars (Langer and Vacanti, 1993). Tissue engineering has emerged as a potential means of growing new tissues and organs to treat such patients, and several approaches are currently under investigation to engineer structural tissues.

Improved biodegradable polymers and copolymers have recently been generated for use in the tissue engineering field. This has allowed developments in the generation of autologous and allogeneic tissues intended for use in transplantation. The role of biomaterials in the in vitro expansion of cultured cells is generally to serve as a vehicle to localize the cells of interest. Biomaterials can also be used in vivo to deliver biologically active substances.

Biodegradable homopolymers and copolymers of lactic and glycolic acid, poly(lactic-co-glycolic acid) (PLGA; now also termed poly(lactide-co-glycolide) or PLG), have become attractive candidates for fabricating tissue engineering matrices due to their flexible and well defined physical properties and relative biocompatibility. The degradation products of these polymers are also natural metabolites and are readily removed from the body.

Several techniques have been used to fabricate polymers into porous matrices for tissue engineering applications, including solvent-casting/particulate leaching (SC/PL) (Mikos et al., 1994); phase separation (Lo et al., 1995); fiber extrusion and fabric forming processing (Cavallaso et al., 1994); and gas foaming (Mooney et al., 1996). However, the current techniques each suffer from their particular drawbacks.

The solvent-casting/particulate leaching and phase separation approaches require the use of organic solvents. Residues of organic solvents that remain in these polymers after processing may damage transplanted cells and nearby tissue and/or inactivate biologically active factors incorporated into the polymer matrix for controlled release. Fiber forming typically requires high temperatures (above the transition temperature of polymer), and is not amenable to processing amorphous polymers. The high temperatures used in such processes would likely denature any biologically active molecules incorporated into the matrix.

The gas foaming method, as exemplified by Mooney et al. (1996), provides a technique to fabricate highly porous matrices from PLGA using a high pressure gas that avoids the use of organic solvents and high temperatures. However, the technique typically yields a closed pore structure, which is disadvantageous in many applications of cell transplantation. In addition, a solid skin of polymer results on the exterior surface of the foamed matrix and this may lead to mass transport limitations.

Therefore, there exists in the art a need for improved polymer materials for use in tissue engineering and in vivo protocols. In terms of in vivo, rather than in vitro uses, several other problems also need to be overcome. These include limitations such as providing biological materials to an appropriate site of the body, exposure of the materials to the appropriate cell types, efficient release and/or provision of the biological materials, maintenance of an effective concentration of biological materials, and prolonged and appropriate activity of the biological materials.

SUMMARY OF THE INVENTION

The present invention overcomes these and other drawbacks inherent in the prior art by providing improved polymer materials for use in in vivo protocols. The invention particularly provides matrices with controlled structural properties in functional association with nucleic acids. Exemplary structural matrices of the invention include alginate matrices and three-dimensional structural matrices with controlled pore structures, including interconnected or open pore structures, each of which are functionally combined with nucleic acids.

The predesigned structural matrix-nucleic acid compositions of the invention have advantages in that they prolong the bioavailability of nucleic acids, allowing cell exposure to nucleic acids for extended time periods. The porosity and other physical properties of the preferred nucleic acid-matrices are also controllable, allowing the number and type of cell populations that are exposed to the nucleic acids to be regulated. As such, the matrix-nucleic acid compositions of this invention represent an important advance in the state of the art of in vivo cell transfection, gene expression and gene therapy.

As used herein, the terms "structural matrix-nucleic acids" and "structural matrix-nucleic acid compositions" broadly refer to any structural matrix in combination with any nucleic acid, such as DNA, RNA, DNA-RNA hybrids, plasmids, vectors, cosmids, phages, viruses and such like. Unless otherwise specifically stated, such as in reference to an RNA construct, the terms "structural matrix-DNA" and "structural matrix-DNA compositions" are also used to succinctly refer any structural matrix in combination with any nucleic acid, such as DNA, RNA, DNA-RNA hybrids, plasmids, vectors, cosmids, phages, viruses and such like. Thus, the term "DNA", unless otherwise specifically stated, is employed for simplicity to refer to the entire spectrum of nucleic acids for use in the present invention.

The invention is broadly based upon any porous structural matrix. All approaches to form porous matrices may be used in the invention, such as, e.g., solvent cast and particulate leaching, phase inversion and other techniques to fabricate porous scaffolds. Preferred embodiments of the invention utilize matrices with pores formed by a gas foaming-particulate leaching process, including those formed from microspheres pre-loaded with nucleic acids. Other preferred embodiments of the invention utilize various types of alginate matrices.

One aspect of the present invention concerns compositions that comprise at least a first nucleic acid segment in association with a structural matrix, wherein:

(a) at least a portion of the structural matrix is comprised of a porous polymer that contains pores formed by gas foaming and pores formed by leaching out of a particulate from the polymer; or (b) at least a portion of the structural matrix is an alginate or modified alginate matrix.

Certain currently preferred methods for preparing porous polymer materials and matrices are those that involve a combination of gas foaming (GF) and particulate leaching (PL) steps, i.e., "GF/PL processes". The so-called "GF/PL" polymers thus produced have two types of porosity: the first formed by the gas-foaming processing and the second formed by the action of particulate leaching.

Such compositions, in which at least a portion of the structural matrix is comprised of a porous polymer that contains pores formed by gas foaming and pores formed by leaching out of a particulate from the polymer, are currently preferred for use in the present invention. At least some portions of such structural matrices may be comprised of a porous polymer that has a substantially uniform open pore structure. Structural matrices consisting essentially of a porous polymer that has an open pore structure are also provided.

One of the important aspects of the present invention is that the structural matrices have controlled pore structures. In certain embodiments, nucleic acid-containing polymers with interconnected and open pore structures will be preferred. The combination of the two foregoing porosity types can be regulated by controlling the processing conditions and starting materials used. Thus, a range of porous polymeric materials can be generated, each having particular advantageous properties.

Structural matrices that comprise at least a first matrix portion comprised of the porous polymer integrally connected to at least a second matrix portion comprised of an impermeable polymer are also included. Further provided are structural matrices that comprise at least a first matrix portion comprised of a porous polymeric material that has a substantially uniform open pore structure, wherein at least a second matrix portion is comprised of the same polymeric material in a form that lacks an open pore structure.

In the broadest aspects of the invention, as shown in U.S. application Ser. No. 08/199,780, filed Feb. 18, 1994, incorporated herein by reference, the controlled pore or alginate polymeric structures, once formulated, may be suitably admixed with the DNA, RNA or other genetic material, to yield the nucleic acid-matrix or gene-matrix preparation. The nucleic acid, DNA or gene may thus be adsorbed, absorbed or otherwise impregnated within the matrix.

In preferred embodiments of the invention, the polymeric structures are formulated with DNA, RNA or other genetic material, to yield the nucleic acid-matrix or gene-matrix preparations. The association of the nucleic acid, DNA or gene is such that it is generally physically immobilized within the polymer during the fabrication process or during a pre-fabrication step (such as in nucleic acid-microsphere preparation), although the nucleic acids may also be incorporated by impregnation, adsorption, or absorption.

For simplicity, control of sterility and to allow most effective incorporation of nucleic acids throughout the controlled, preferably open pore, structure of the matrix, the nucleic acids are preferably formulated into the matrices of the invention during the fabrication process, including during one or more pre-fabrication steps.

An important advantage of incorporation during fabrication, including pre-fabrication, is that the subsequent nucleic acid bioavailability, including release as an example, is actually controlled by the fabrication and/or pre-fabrication materials and steps, i.e., by controlling polymer formation, degradation and pore size, rather than later being a function only of desorption from the polymer surface. As used herein, the term "bioavailability" means any and all processes by which the nucleic acids from the matrix are rendered available for cellular uptake and expression. One preferred method of cellular uptake and expression is where cells migrate into the matrix, encounter and take up the nucleic acids and express the encoded products.

Accordingly, it will be understood that the term "release", as used in reference to the release of one or more nucleic acid from a structural matrix means that the nucleic acids are "expressible". In various operative methods of the invention, cells that migrate into the structural matrix-nucleic acid composition may further alter the chemical and physical properties of the matrix, thereby facilitating "release" or "further release". As such, in the broadest aspects of the invention, nucleic acids may still be released from structural matrices and expressed by cells even where the nucleic acids were originally covalently attached to one or more components of the matrix.

The overall fabrication is thus generally achieved by adding the genetic material to the mixture of polymer particles and leachable particulate materials prior to molding and compression, and by executing the methodology described herein. In certain embodiments, the nucleic acids are already incorporated within polymer particles, such as beads or microspheres, prior to adding the leachable particulate materials and executing the gas foaming-particulate leaching methodology.

In certain embodiments, closed pore polymer-nucleic acid combinations can be directly used in sustained nucleic acid provision or delivery embodiments, both in vitro and in vivo. The preparation of a closed pore matrix structure does not utilize any leachable particulate and can be simply achieved using a one step foaming process.

In preferred embodiments, e.g., to generate a nucleic acid matrix that facilitates cellular invasion, a matrix with an open pore structure will be employed. Open pore structure nucleic acid-matrices can be created using a one step GF/PL process, a GF/PL process with a pre-fabrication step or a two step GF/PL process. In a preferred one step GF/PL process, the polymer, leachable particulate and nucleic acid are mixed, foamed and leached. In a preferred GF/PL pre-fabrication process, polymer particles, such as beads or microspheres already pre-loaded with nucleic acids are then mixed with leachable particulate, foamed and leached. In a two step GF/PL process, the polymer and nucleic acid are first foamed and then broken into pieces. The ground pieces are then mixed with a leachable particulate, foamed again, and the particulate removed by leaching.

According to certain preferred nucleic acid-matrix preparation processes of the invention, a mixture of DNA, RNA, plasmids, vectors, viral particles or other genetic material is admixed with polymer particles and leachable particulate material(s). The three component mixture is then molded, optionally with compression, to a desired size and shape. The mixture is preferably molded by compression molding at room temperature, or other suitable temperature to effect the molding, to the size and shape that is substantially the same as that desired for its ultimate use.

According to other preferred nucleic acid-matrix preparation processes of the invention, the nucleic acids are first incorporated into polymer particles, preferably, beads or microspheres, to provide pre-loaded polymer particles, beads or microspheres. Any microsphere fabrication process may be used, including atomization/extraction processes operated at cryogenic temperatures. The polymer particles, beads or microspheres pre-loaded with nucleic acids are then admixed with the leachable particulate material(s) and the two component mixture is later subjected to gas-foaming particulate leaching. The nucleic acid-containing microspheres and leachable particulate are typically first molded, optionally with compression, to a desired size and shape, generally guided by the ultimate intended use.

The molded mixture, whether prepared from a three component admixture, or two component nucleic acid-loaded particles or microspheres, is then subject to a high pressure gas atmosphere so that the gas dissolves in the polymer. Next, a thermodynamic instability is created, for example by reduction of the pressure, so that the dissolved gas nucleates and forms gas pores within the polymer. The gas pores cause expansion of the polymer particles, microspheres or nucleic acid-loaded particles or microspheres and as they expand they fuse, creating a continuous polymer matrix containing the particulate material. Finally, the particulate material is leached from the polymer with a leaching agent creating a further porosity. Nucleic acids and genetic materials are substantially unaffected by each of the foregoing processes, including the pre-fabrication step.

The polymer and particulate materials are selected so that the particulate can be leached with a leaching agent that does not significantly dissolve the polymer or otherwise significantly adversely impact either the polymeric material or genetic material admixed therewith. The mixture is preferably as uniform as possible and can be provided by any conventional means, by pre-loading microspheres with the nucleic acids, or by combinations thereof.

Any polymer with which nucleic acids can be mixed, or into which nucleic acids can be incorporated, into which gas can be dissolved and pores formed thereby, and in which a particulate can be incorporated and leached therefrom can be used in the process. It is generally preferred, to facilitate dissolution of the gas, that the polymer be an amorphous or predominantly amorphous polymer. However, if it is desired to use a crystalline polymer, the crystallinity can be reduced to a level such that the gas can be dissolved therein and then the crystallinity restored after formation of the pores.

Depending upon the application of the materials, the polymer may be selected to be biodegradable or non-biodegradable. Biodegradable polymers will often be preferred. For the most preferred applications of the invention, the polymer is preferably biocompatible to the environment in which it is used, such as the human in vivo environment.

A preferred useful class of polymers for use in the invention are homopolymers and copolymers of lactic acid and glycolic acid, for example, poly-L-lactic acid (PLLA), poly-D,L-lactic acid (PDLLA), polyglycolic acid (PGA) and copolymers of D,L-lactide and glycolide (PLGA), particularly with 50% or more of the lactide in the copolymer. Polylactic-polyglycolic acid, known as PLGA, is now also termed poly(lactide-co-glycolide), or PLG, and such terms may be used interchangeably herein. Other useful polymers, for example, are aliphatic polyesters, such as polyhydroxybutyrate, poly-ε-caprolactone. Further, polyanhydrides, polyphosphazines, polypeptides may be used.

As polymer composition and molecular weight have an effect on the porosity and mechanical properties of three dimensional matrices, altering the polymer composition allows for functional control. In the GF/PL processes, copolymers of PLGA have been shown to foam to a much greater extent than either homopolymer of PGA or PLLA. This is likely due to an increased gas dissolution in amorphous polymers, as compared to crystalline polymers. An informed choice between copolymer and homopolymer can thus be made.

The molecular weight of the polymer also has an effect on scaffold porosity. Polymers with a high molecular weight (large i.v.) do not form scaffolds with as high porosity as the same polymers with a lower molecular weight. The longer polymer chains of the high molecular weight polymer likely entangle to a greater extent, thus providing a stronger resistance to expansion than the shorter polymer chains. Such can also be considered in choosing a polymeric matrix for use with the invention.

In certain preferred embodiments, advantageous pore formation is achieved by the use of a low molecular weight amorphous copolymer of lactide and glycolide.

In certain other preferred embodiments, advantages are achieved by pre-fabricating microspheres with nucleic acids prior to gas foaming/particulate leaching to form three-dimensional matrices. These approaches provide high incorporation efficiencies and sustained release, cellular uptake and expression of nucleic acids, which release, cellular uptake and expression can be controlled in part through the microsphere fabrication process.

Blends of different polymers may also be used, as may polymers that contain other agents, particularly those that affect the mechanical properties of the resulting matrix. For example, blends of different PLGA polymers that have distinct properties can be used to take advantage of the properties of each polymer. Also, other polymers can be blended with, e.g., PLGA polymers, particularly for modifying the mechanical properties thereof. For example, blends of PLGA polymers and alginate materials can provide a tougher matrix with greater elasticity and ability to withstand greater strain before breaking.

Similarly a plurality of microspheres pre-fabricated with nucleic acids may be used, where the microsphere population comprises at least two different polymers. The individual microspheres can themselves be mixtures of polymeric materials (heteropolymeric microspheres), or a mixture of microspheres can be employed in which each individual microsphere is comprised of a single polymer (homopolymeric microspheres). Different nucleic acids can be associated with either each type of polymer, each type of microsphere, or both, so that the ultimate release kinetics and cellular uptake and expression can be controlled.

The present invention therefore contemplates the use of blends of polymers that result in matrices with better pliability and/or strength. Blends using materials that act as plasticizers, toughening agents or modifiers of other properties may be preferred for certain aspects of the invention. Such materials can either be polymers or smaller molecule agents that may act in a temporary manner and then diffuse from a matrix.

The leachable particulate for use in the invention will be any particulate material that can be leached from the polymer matrix with a leaching agent and that does not significantly adversely affect the polymer or the genetic material in the admixture. Currently preferred are salts soluble in an aqueous medium, preferably water, and sugars and sugar alcohols soluble in aqueous media, preferably water, serum and/or biological tissue fluids. As salts, NaCl, Na citrate, Na tartrate, and KCl are useful particulate materials. Useful sugar and sugar alcohol particulates include trehalose, glucose, sucrose and mannitol, of which trehalose is currently preferred. Other useful particulates leachable by dissolution include, for example, gelatin, collagen, heparin and heparin derivatives, and alginate particulates.

It is also possible to use particulates that are leachable by organic solvents where the solvent does not adversely effect the polymer; however, this is not preferred since such would mitigate the advantage of lack of need for an organic solvent and lack of residue in the product. The use of organic solvents would also generally mean that the DNA should be added after matrix formulation.

In general, the size of any particulate will generally affect the size of the pores formed upon leaching of the particulate. Although not limiting of the invention, it is currently preferred that the particulate has an average size of from about 10 to about 500 microns. This size will correspond approximately to the size of the pores formed by the leaching thereof.

A gas is dissolved in the polymer, preferably in the molded, mixture of polymer, particulate and nucleic acid, or nucleic acid-loaded microsphere and particulate, by subjecting the polymer, mixture or microsphere mixture to a pressurized atmosphere of a gas that is inert to the system and that will dissolve in the polymer under suitable conditions. Examples of suitable gases include $CO_2$, air, nitrogen, helium, argon and oxygen.

Also, volatile liquids that provide a gas at the gas foaming temperature may be used, e.g., water. Other gases or volatile liquids that form gases known to be useful as blowing agents may also be used. These include, for example, fluorinated, including perfluorinated, hydrocarbons. Preferred for these are aliphatic or cycloaliphatic fluorinated hydrocarbons of up to 8 carbon atoms such as trifluoromethane, difluoromethane, difluoroethane, tetrafluoroethane, heptafluoroethane, perfluoropropane, perfluorobutane, perfluorocyclobutane, perfluoropentane, perfluorohexane, perfluoroheptane, pefluorooctane, perfluorocyclopentane, perfluorocyclohexane, hexafluoropropane and heptafluoropropane.

Sulfur hexafluoride may also be a useful blowing agent. Other known blowing agents include alkanes such as propane, butanes and pentanes; cycloalkanes and cycloalkenes such as cyclobutane, cyclopentene and cyclohexene; dialkyl ethers such as dimethyl ether, methyl ethyl ether and diethyl ether; cycloalkylene ethers such as furan; ketones such as acetone and methyl ethyl ketone; and carboxylates such as formic acid, acetic acid and propionic acid. All such agents may be used in these aspects of the invention.

The pressure is generally selected to facilitate dissolution of gas into the polymer and will, thus, depend upon the gas used, the polymer used and the temperature. Pressures of from about 600 to about 900 psi are generally useful for $CO_2$ and PLGA polymers, although this is not limiting on the invention. Gases at super- or sub-critical conditions can also be used. Furthermore, a volatile liquid that can be dissolved in the polymer and that forms a gas upon imposition of the thermodynamic instability can also be used. As an example, $CO_2$ can be dissolved in a mixture of poly[D,L-lactic-co-glycolic acid] polymer and NaCl particulate at a pressure of about 800 psi applied for about 48 h to allow saturation.

The specific gas used in foaming can be an important variable in the production of porous matrices for use herewith and the choice of gas used has an effect on the final scaffold structure. $CO_2$ produces highly porous matrices, whereas $N_2$ and He do not yield measurable pore formation. Although the mechanism underlying these results does not need to be known in order to practice the invention, the greater degree of foaming experienced with $CO_2$ as compared to both N2 and He may be the result of a specific interaction between $CO_2$ and the carbonyl groups of PLGA. Gas equilibration times and pressure release rates may also affect the porosity and stability of the matrices formed.

In order to initiate nucleation of the dissolved gas and growth of gas pores in the material, a thermodynamic instability is created. This phenomenon is described by Park et al. (1995; incorporated herein by reference). Preferably, this is done by lowering the pressure of the gas atmosphere, for example, down to about atmospheric pressure over a short time period. The time period being, for example, from a few seconds to about 15 or 30 minutes or so. The gas phase separates from the polymer via pore nucleation and growth of the pores occurs through diffusion of gas into areas adjacent the nucleation sites. The pore growth in turn reduces the polymer density.

Other methods for creating the instability, such as raising the temperature, may be used, but, are not preferred due to ease of processing of the current methods. The pore structure and pore size of the gas pores formed will be a factor of, for example, the type of gas used; the amount of gas, which will depend upon temperature and initial and final pressure of the gas atmosphere applied; the solubility of the gas in the particular polymer; the rate and type of pore nucleation; and the diffusion rate of the gas through the polymer to the nuclei. These and other factors can be adjusted to provide gas pores of a suitable size. Sufficient gas should be dissolved to cause formation of a continuous polymer matrix when the polymer expands during gas pore growth.

As a result of the thermodynamic instability, pore nucleation and gas pore formation and expansion, the polymer containing the particulate material and nucleic acid forms a continuous phase, i.e. matrix, around the gas pores.

The particulate is leached from the polymer with a leaching agent. Useful as leaching agent is any agent that will leach, e.g., dissolve and remove, the particulate from the polymer. An aqueous-based leaching agent, particularly water, is preferred. Body fluids can also be used as both in situ and in vitro leaching agents. The methods are executed such that the leaching agent that leaches the particulate from the polymer does not leach or otherwise remove a substantial amount of the genetic material from the polymer. However, as the preferred embodiments of the present invention involve the expression of the DNA or genetic material in target cells contacted by the gene-matrix preparation, and as gene expression provides for long-term effects, loss of some genetic material from the matrix during the leaching process will not be detrimental to practice of the invention.

Uses of the invention where the particulate is not removed before implantation, but rather dissolves in the body to create the porosity for cell invasion, are also provided. The dissolving particulates can be chosen to have a minimal effect on the surrounding tissue and to diffuse away. They may also be chosen to actually activate cell migration into the scaffolds, such that the particulate that leaches out modulates cellular invasion by controlling chemotaxis of cells to the site and such like.

In such embodiments, the same processes are used to fabricate the matrices, but leaching is not conducted before implantation. Rather, the solid material (containing polymer, nucleic acid and particulate) is implanted. The particulate is then allowed to leach or dissolve in the body simply by exposure to body fluids, thus creating the porous structure. The criteria for the particulate in such processes are that it be biocompatible and soluble in aqueous solutions. Sugars are preferred, such as sucrose, mannitol, glucose etc.

In such processes, there is further control over the kinetics of nucleic acid release and cellular uptake and expression, as these processes can be controlled in part by the rate of dissolution of the particulate in the body following implantation. Rapidly dissolving particulates allow faster nucleic acid release and bioavailability, while slower dissolving particulates retard nucleic acid release and bioavailability. In addition, this allows virtually 100% efficiency of DNA provision or delivery, as nucleic acids are not lost in the particulate leaching step, which accounts for most of the nucleic acids lost during processing.

Succinctly, the preparative methods comprise providing at least a first nucleic acid segment to a structural matrix, wherein at least a portion of the structural matrix is comprised of a porous polymer that contains pores formed by gas foaming and pores formed by leaching out of a particulate from the polymer.

The methods generally comprise leaching out the particulate material from an intermediate composition comprising a gas foamed polymeric material, at least a first nucleic acid segment and a leachable particulate material. The intermediate composition is preferably prepared by incorporating at least a first nucleic acid segment within a polymeric structure in particle form, e.g., as beads or microspheres, admixing with the leachable particulate material and subjecting the admixture to a gas foaming process.

In steps, these methods comprise incorporating at least a first nucleic acid segment within a polymeric structure in particle form, e.g., as beads or microspheres, admixing with the leachable particulate material, subjecting the admixture to a gas foaming process and leaching out the particulate material from the gas foamed admixture.

Such methods therefore generally comprise the steps of:
  (a) preparing an admixture comprising particles of a polymeric material capable of forming a polymeric structure, at least a first nucleic acid segment and a leachable particulate material;
  (b) subjecting the admixture to a gas foaming process to create a porous polymeric structure that comprises at least a first nucleic acid segment and the leachable particulate material; and
  (c) subjecting the porous polymeric structure to a leaching process that removes the leachable particulate material from the porous polymeric structure, thereby producing a polymeric structure of additional porosity that comprises at least a first nucleic acid segment.

In certain preferred embodiments, the admixture will comprise at least a first nucleic acid segment, beads or microspheres capable of forming a polymeric structure and the leachable particulate material. In further preferred embodiments, at least a first nucleic acid segment will be incorporated within the beads or microspheres prior to admixing and prior to gas foaming.

The microsphere admixtures therefore form other aspects of the invention, wherein compositions, admixtures and kits thereof are provided that comprise a leachable particulate material in combination with beads or microspheres of a polymer capable of forming a gas-foamed polymeric structure, wherein the beads or microspheres have incorporated therein at least a first nucleic acid segment.

The methods for making a structural matrix-nucleic acid composition may thus comprise:
  (a) pre-fabricating a polymeric particle that is capable of forming a polymeric structure, preferably a bead or microsphere, with at least a first nucleic acid segment to prepare a polymeric particle that incorporates at least a first nucleic acid segment;
  (b) preparing an admixture comprising a leachable particulate material in combination with the pre-fabricated polymeric particle, bead or microsphere that incorporates at least a first nucleic acid segment;
  (c) subjecting the admixture to a gas foaming process to create a porous polymeric structure that comprises at least a first nucleic acid segment and the leachable particulate material; and
  (d) subjecting the porous polymeric structure to a leaching process that removes the leachable particulate material from the porous polymeric structure, thereby producing a polymeric structure of additional porosity that comprises at least a first nucleic acid segment.

Alternatively, the admixtures may be prepared by:
  (a) preparing a pre-mixture comprising particles capable of forming a polymeric material and at least a first nucleic acid segment;
  (b) subjecting the pre-mixture to a first gas foaming process to create a porous polymeric material that comprises the at least a first nucleic acid segment;
  (c) breaking the porous polymeric material that comprises the at least a first nucleic acid segment to form ground particles; and
  (d) adding a leachable particulate material to the ground particles to prepare the admixture.

The methods for making a structural matrix-nucleic acid composition may thus comprise:
  (a) preparing a first admixture comprising at least a first nucleic acid segment and particles capable of forming a polymeric material;
  (b) subjecting the first admixture to a first gas foaming process to create a porous polymeric material that comprises the at least a first nucleic acid segment;
  (c) breaking the porous polymeric material that comprises the at least a first nucleic acid segment to form ground particles;
  (d) adding a leachable particulate material to the ground particles to prepare a second admixture;
  (e) subjecting the second admixture to a second gas foaming process to create a second porous polymeric material that comprises the at least a first nucleic acid segment and the leachable particulate material; and
  (f) subjecting the second porous polymeric material to a leaching process that removes the leachable particulate material from the second porous polymeric material, thereby producing a final polymeric material of additional porosity that comprises the at least a first nucleic acid segment.

The preferred DNA-matrix preparation methods, or "GF/PL processes", of the invention result in a surprisingly effective combination of gas foamed and particulate leached porosity, with the particulate leached pores also being termed "macropores". The combined use of gas-foaming and particulate leaching, as disclosed herein, provides a controlled range of DNA-containing matrices with interconnected and open pore structures, the particular composition of which is dictated by the processing conditions and materials employed.

Interconnected and open pore structures are preferably prepared by using a mixture of polymer and leachable particulate wherein the amount of leachable particulate is at least about 50% by volume. A higher amount of leachable particulate can be used to obtain a fully interconnected structure, up to about 99%.

Overall, the process of the invention can provide materials with a total porosity of, for example, from above 0 to 97% or even higher. In certain embodiments, it will be preferable to use matrices with a total porosity of about 40%, about 50%, about 60%, about 70%, about 80%, about 90%, about 95%, about 96% or about 97% or so.

The DNA-containing materials of the invention also generally exhibit much higher strength properties, e.g., tensile strength, as compared to previous materials. For example, preferred materials according to the invention have a tensile modulus in the range of about 850 kPa, and more preferably, up to and including about 1100 kPa, or even higher. The preferred materials also exhibit improved compression resistance. For instance, preferred materials have a compression modulus of, for example, about 250 kPa, and more preferably, up to and including about 289 kPa, or even higher. Typical prior art materials exhibit a tensile modulus of only about 334±52 kPa and a compression modulus of only about 159±130 kPa.

Polysaccharides, such as alginates, modified to bind biological agents may also be used in the invention. Alginates modified so that they have controllable physical properties, such as sol-gel properties, and the like, are contemplated.

Alginates comprising at least one alginate chain section bonded to at least one molecule useful for cellular interaction (cell adhesion molecules, cell attachment peptides, proteoglycan attachment peptide sequences, proteoglycans, and polysaccharides exhibiting cell adhesion) are also envisioned. Particular examples are RGD peptides, fibronectin, vitronectin, Laminin A, Laminin B1, Laminin B2, collagen 1 or thrombospondin. Various polypeptide or peptide growth factors or enzymes may also be used as the cellular interacting molecules.

The preparation and use of porous hydrogel materials formed by first creating gas pockets in the gel and then removing the gas to create a material with an open, interconnected pore structure is also included. Such matrices maintained their pore structure over extended time periods and have high mechanical integrity. U.S. Provisional Application Ser. No. 60/128,681, filed Apr. 9, 1999, the priority document for U.S. Pat. No. 6,511,650, is specifically incorporated herein by reference without disclaimer for the purposes of describing the preparation and use of such unique polymeric materials and matrices thereof.

Accordingly, at least a portion of the structural matrix may be a modified alginate matrix prepared by a method comprising:

(a) providing a solution of a hydrogel-forming material and a surfactant;

(b) mixing said solution in the presence of a gas to form a stable foam;

(c) exposing said stable foam to conditions or agents that result in gelling of the hydrogel-forming material and in the generation of gas bubbles therein; and (d) exposing the hydrogel containing gas bubbles to a vacuum to release the gas and form the hydrogel material having macroporous open pore porosity.

Irrespective of the form of matrix, the nucleic acid segment may be a DNA or RNA molecule, an antisense nucleic acid molecule, a nucleic acid segment comprised within a plasmid or recombinant expression vector, such as a recombinant viral expression vector, e.g., a nucleic acid segment that is operatively positioned downstream from a promoter within a recombinant adenovirus, a recombinant adeno-associated virus (AAV), a recombinant lentivirus or a recombinant retrovirus.

The nucleic acid segments may encode a non-translated therapeutic product, such as an antisense a ribozyme, or a selected protein or polypeptide. Marker proteins are included, as are therapeutic proteins and polypeptides, particularly human proteins and polypeptides. Exemplary nucleic acid segments encode proteins or polypeptides that stimulate growth or proliferation of cells, such as bone progenitor cells when expressed in such cells; that stimulate wound healing fibroblasts, granulation tissue fibroblasts and/or repair cells when expressed in such cells; that stimulate an antigenic or immunogenic response when expressed by cells of the immune system, such as antigen presenting cells; and cytotoxic or apoptosis-inducing proteins or polypeptides that induce cell death upon expression in a target cell.

Particular examples include nucleic acid segments that encode a transcription or elongation factor, cell cycle control protein, kinase, phosphatase, DNA repair protein, oncogene, tumor suppressor, angiogenic protein, anti-angiogenic protein, immune response stimulating protein, cell surface receptor, accessory signaling molecule, transport protein, enzyme, anti-bacterial or anti-viral protein or polypeptide.

Further examples include nucleic acid segments that encode a hormone, neurotransmitter, growth factor, growth factor receptor, interferon, interleukin, chemokine, cytokine, colony stimulating factor or chemotactic factor protein or polypeptide.

Particular examples are growth hormone (GH) proteins and polypeptides; parathyroid hormone (PTH) proteins and polypeptides, such as PTH1-34 polypeptides; bone morphogenetic protein (BMP) proteins and polypeptides, such as BMP-2A, BMP-2B, BMP-3, BMP-4, BMP-5, BMP-6, BMP-7 and BMP-8; TGF-$\alpha$, TGF-$\beta$1, TGF-$\beta$2 and latent TGF$\beta$ binding protein (LTBP) proteins and polypeptides; activin/inhibin proteins and polypeptides; fibroblast growth factor (FGF); granulocyte/macrophage colony stimulating factor (GMCSF); epidermal growth factor (EGF); platelet derived growth factor (PDGF); insulin-like growth factor (IGF) and leukemia inhibitory factor (LIF).

Compositions comprising at least a first and second and/or third nucleic acid segment are provided, as are those comprising a plurality of nucleic acid segments.

The compositions also comprise populations of cells, both in vitro and in vivo. Portions of the nucleic acid segments may be taken up by the cells comprised within such compositions either before or after transplantation to an animal or human, or during both stages.

The present invention also provides gene transfer kits that comprise any gene-matrix composition in accordance herewith in at least a first suitable container. Implantable medical devices comprising gene-matrix compositions in accordance herewith are also provided in bioimplantable forms.

The compositions, kits and devices of the invention have various uses, such as in the controlled release of nucleic acids; in expressing nucleic acid segments in cells; in culturing recombinant cells that express nucleic acid segments; in gene transfer to cells within tissue sites of animals and humans.

Uses of the compositions, kits and devices thus extend to the manufacture of medicaments for all aspects of gene therapy, such as stimulating bone tissue growth; promoting wound healing, tissue regeneration and organ regeneration; generating immune responses; killing aberrant, malignant and virally-infected cells; and in cell transplantation, tissue engineering and guided tissue regeneration.

The methods of the invention include the controlled release and bioavailability of nucleic acids, allowing the release of at least a first nucleic acid segment from a nucleic acid-structural matrix composition that comprises at least a first nucleic acid segment in association with a structural alginate or modified alginate matrix or a structural matrix that comprises at least a portion fabricated from a porous polymer that contains pores formed by gas foaming and pores formed by leaching out of a particulate from the polymer.

The release and bioavailability of the nucleic acids from the nucleic acid-structural matrix in all embodiments may be controlled by controlling the rate of degradation or dissolution the structural matrix, by controlling diffusion through the pores in the structural matrix, by desorption from the structural matrix, by a combination of such processes together, and/or with other biological, chemical and/or physical processes.

Methods for providing at least a first nucleic acid segment to a cell are provided, comprising contacting a cell with a nucleic acid-structural matrix composition of the invention in a manner effective to provide at least a first nucleic acid segment to the cell, i.e., in a manner effective to release at least a first nucleic acid segment from the nucleic acid-structural matrix composition in a manner such that it can be taken up by the cell.

Further provided are methods for expressing at least a first nucleic acid segment in a cell, comprising contacting a cell with a nucleic acid-structural matrix composition of the invention in a manner effective to express at least a first nucleic acid segment in the cell. The cell may be located in a tissue site of an animal or human, wherein the nucleic acid-structural matrix composition is provided thereto.

In vitro culture methods are also provided, which comprise growing cells in contact with a therapeutic gene-structural matrix composition of the invention. The cells may be separated from the therapeutic gene-structural matrix composition and used in vitro and/or provided to an animal. The cells may also be maintained in contact with the therapeutic gene-structural matrix composition, which may be provided to an animal or patient.

Expression methods are provides comprising contacting a tissue site of an animal or human with a nucleic acid-structural matrix composition of the invention in a manner effective to express at least a first nucleic acid segment in cells within the tissue site. Transcriptional and translated protein and polypeptide products are thus expressed, including therapeutic proteins and polypeptides.

Target cells include bone progenitor cells (e.g., stem cells, macrophages, granulation tissue fibroblasts, vascular cells, osteoblasts, chondroblasts and osteoclasts) located within bone progenitor tissue sites or bone fracture sites; repair cells or fibroblasts located within wound tissue sites, such as sites of connective tissue injury or organ damage; immune and antigen presenting cells; and aberrant, malignant and infected cells.

Methods for stimulating bone progenitor cells located within a bone progenitor tissue site of an animal or human comprise contacting the tissue site with an osteotropic gene-structural matrix composition of the invention in a manner effective to express at least a first osteotropic gene in the cells. Expression of the osteotropic gene in the cells stimulates the cells to promote bone tissue growth, e.g., in a bone cavity site that is the result of dental or periodontal surgery or the removal of an osteosarcoma.

Fibroblast stimulation methods comprise contacting a wound tissue site of an animal or human with a therapeutic gene-structural matrix composition of the invention in a manner effective to express at least a first therapeutic gene in the fibroblast cells. Expression of the therapeutic gene in the fibroblast cells stimulates the fibroblast cells to promote wound healing.

Methods for promoting wound healing comprise applying a biocompatible structural matrix containing a therapeutic gene expression construct to a wound site in an animal or human so that repair cells that migrate to the wound site infiltrate the matrix, acquire a therapeutic gene expression construct, and express the encoded gene product encoded in vivo, thereby promoting wound healing.

Further methods are for expressing at least a first immunogen-encoding gene in immune cells or antigen presenting cells within a tissue site of an animal or human, comprising contacting the tissue site with an immunogen-encoding gene-structural matrix composition of the invention in a manner effective to express at least a first immunogen-encoding gene in immune cells or antigen presenting cells within the tissue site.

These lead to immunization methods that comprise contacting a tissue site of an animal or human with an immunogenic gene-structural matrix composition of the invention in a manner effective to express at least a first immunogenic gene in immune or antigen presenting cells that migrate into the tissue site, thereby causing the immune or antigen presenting cells to stimulate an antigenic or immunogenic response in the animal or human. Expression of the at least a first immunogen-encoding gene in the immune or antigen presenting cells causes such cells to stimulate an immune response in the animal or humans. The immunogenic gene-structural matrix composition may comprise a plurality of immunogenic genes obtained from one or more pathogenic organisms.

Cytotoxic methods for treating diseased cells in an animal or human comprise contacting a tissue site of an animal or human with a cytotoxic gene-structural matrix composition of the invention in a manner effective to express at least a first cytotoxic gene in diseased cells within the tissue site. Cancer cells and virally-infected cells are treated thereby, including where the cytotoxic genes have direct cytotoxic effects, induce apoptosis and/or inhibit proliferation of the diseased cells.

Methods for transplanting cells into an animal or human comprise applying to a tissue site of an animal or human a cell-therapeutic gene-structural matrix combination of the invention. The cells of the cell-therapeutic gene-structural matrix combination may be recombinant cells that comprise the therapeutic gene(s) applied to the matrix.

Tissue engineering methods for animals and humans comprise contacting a tissue site of an animal or human with a therapeutic gene-structural matrix composition of the invention in a manner effective to both express at least a first therapeutic gene in cells within the tissue site and to provide a matrix for tissue growth. Guided tissue regeneration comprises contacting a regenerating tissue site of an animal or human with a therapeutic gene-structural matrix composition of the invention in a manner effective to both express at least a first therapeutic gene in cells within the regenerating tissue site and to provide a matrix for tissue regeneration.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of illustrative embodiments and the detailed examples presented herein.

FIG. 3A shows the statistically significant increase in vessel number stimulated by released PDGF relative to the control β-galactosidase at both 2 weeks ($p<0.05$) and 4 weeks ($p<0.01$). FIG. 3B shows the statistically significant increase in vessel area stimulated by released PDGF relative to the control β-galactosidase at both 2 weeks ($p<0.05$) and 4 weeks ($p<0.01$). Statistical analysis was performed using the software program Instat.

FIG. 5A and FIG. 5B show that the direct injection of PDGF plasmid DNA is unable to increase the granulation layer thickness or vessel number relative to control β-galactosidase at either 2 weeks or 4 weeks.

FIG. 6A and FIG. 6B demonstrate continuous and sustained release of plasmid DNA up to 30 days and >160 days, respectively.

DESCRIPTION OF ILLUSTRATIVE EMBODIMENTS

Figure 1:
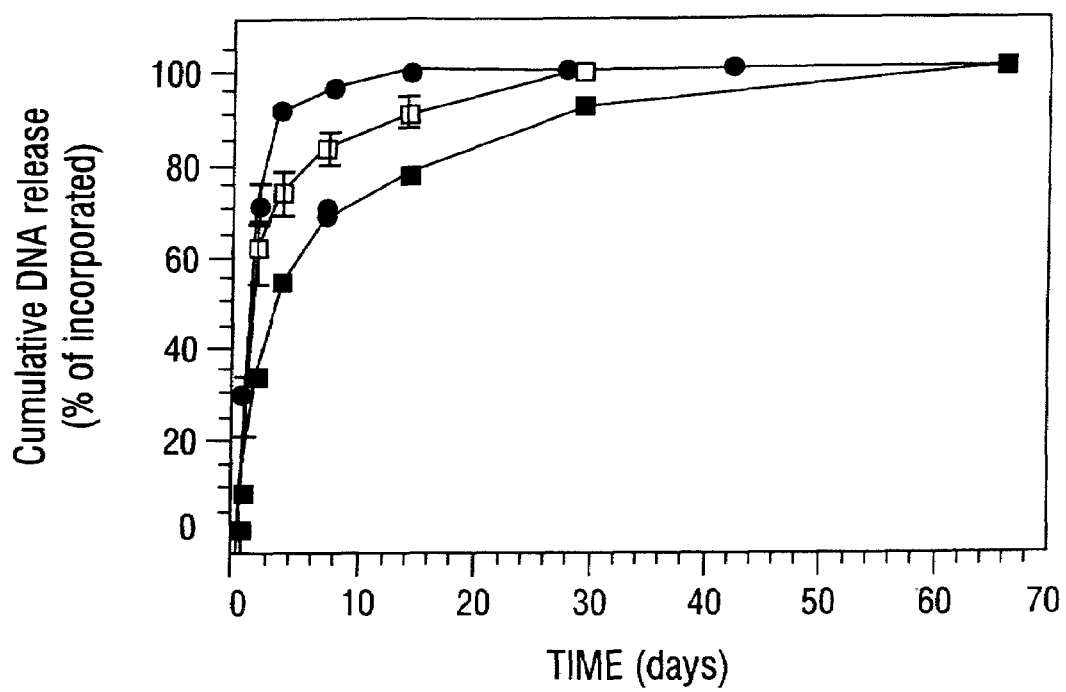
FIG. 1. Cumulative release of plasmid DNA from PLGA polymer sponges fabricated by the gas foaming procedure. The figures shows release from sponges of proportions 75:25 (i.v.=0.2) (●; closed circle), 85:15 (i.v.=0.7) (□; open square) and 75:25 (i.v.=0.7) (■; closed square). Note, i.v. means intrinsic viscosity, a frequently used measure of molecular weight.

One approach to tissue engineering involves transplanting cells on biodegradable polymer matrices. Matrices serve to deliver cells to a specific anatomical site, create and maintain a space for tissue development, and guide tissue formation before degrading (Kim and Mooney, 1998). Limitations of this approach include the need to isolate and expand cells in vitro, and poor survival of many cell types following transplantation (Mooney et al., 1997).

An alternative approach under investigation is the delivery of tissue-inductive proteins (e.g., BMPs, PDGF) (Deuel, 1997). However, such methods have a number of complications when applied to tissue engineering, including decreased protein stability in the delivery system (Langer, 1992).

Recently, delivery of plasmid DNA encoding for inductive factors has been proposed as a replacement to direct delivery of the protein (Jong et al., 1997; Labhasetwar et al., 1998). However, the delivery of plasmid DNA in vivo is typically associated with low levels of gene transfer and cellular expression, perhaps due to a limited exposure of cells to the plasmid (Ledley, 1996).

Indeed, in vivo gene therapy, particularly that utilizing the delivery of naked DNA, is generally limited by a number of factors, including delivery of DNA to the appropriate site at a desired concentration, poor transfection efficiency of the plasmid, expression of the transgene for short times, and exposure of the plasmid to the appropriate cell types.

In response to a variety of problems in the art, the present invention provides a series of pre-designed structural matrices that allow the exposure of cells to genetic material, such as plasmid DNA, for extended periods of time. Importantly, these matrices control the numbers and populations of cells that are exposed to the genes or DNA contained therein, and thus control the cells that can express the desired gene.

The entire specification, claims, figures and sequence listings of the following patent applications are specifically incorporated herein by reference without disclaimer: provisional application Ser. No. 60/085,305, filed May 13, 1998; provisional application Ser. No. 60/109,054, filed Nov. 19, 1998; U.S. application Ser. No. 08/199,780, filed Feb. 18, 1994, now U.S. Pat. No. 5,763,416; U.S. application Ser. No. 08/316,650, filed Sep. 30, 1994, now U.S. Pat. No. 5,942,496; U.S. application Ser. No. 08/479,722, filed Jun. 7, 1995, now U.S. Pat. No. 6,074,840; U.S. application Ser. No. 08/631,334, filed Apr. 12, 1996, now U.S. Pat. No. 6,143,037; PCT Application Serial No. PCT/US97/07301, filed Apr. 11, 1997 (WO 97/38729); U.S. application Ser. No. 08/662,341, filed Jun. 12, 1996, now U.S. Pat. No. 6,143,037; PCT Application Serial No. PCT/US97/10079, filed Jun. 11, 1997 (WO 97/47254); U.S. application Ser. No. 08/752,919, filed Nov. 20, 1996, now abandoned; PCT Application Serial No. PCT/US97/20882, filed Nov. 20, 1997 (WO 98/22492); U.S. patent application Ser. No. 09/402,119, filed Sep. 20, 1999, now U.S. Pat. No. 6,281,256; PCT Application Serial No. PCT/US98/06188, filed Mar. 31, 1998 (WO 98/44027), which designates the United States; U.S. Provisional Application Ser. No. 60/042,198, filed Mar. 31, 1997 the priority document for U.S. Pat. Nos. 6,281,256 and 6,797,738 and WO 98/44027; U.S. Provisional Application Ser. No. 60/026,362, filed Sep. 19, 1996, the priority document for U.S. Pat. No. 6,642,363; U.S. Provisional Application Ser. No. 60/026,467, filed Sep. 19, 1996, the priority document for U.S. Pat. No. 6,642,363; U.S. Provisional Application Ser. No. 60/041,565, filed Mar. 21, 1997, the priority document for U.S. Pat. No. 6,642,363; PCT Application Serial PCT/US97/16890, filed Sep. 19, 1997 (WO 98/12228); U.S. Provisional Application Ser. No. 60/066,926, filed Nov. 17, 1997, the priority document to U.S. application Ser. No. 09/572,786, now abandoned; and U.S. Provisional Application Ser. No. 60/128,681, the priority document for U.S. Pat. No. 6,511,650, filed Apr. 9, 1999. Applicants expressly reserve the right to claim priority to any one or more, or all of, the foregoing patent applications.

The inventors' novel approach involves incorporating nucleic acids, such as plasmid DNA, into 3-dimensional structural matrices that have a pre-defined structure and are fabricated from polymers with controlled physical and chemical properties. The resultant structural matrix DNA composition creates and maintains a space for cellular transfection to occur, and the matrix design controls the numbers and populations of cells exposed to the nucleic acid or plasmid DNA. The cellular invasion rate is particularly controlled by the pore size of the matrix.

Such controlled, structural matrices that incorporate DNA are ideal for use in tissue engineering as they provide for the sustained provision of genetic material and the transfection of large numbers of cells in vivo. They also have the advantage that the sustained provision of DNA from the controlled polymer matrix is able to transfect large numbers of cells, including those more distant from the administration site, leading to production of therapeutic proteins (tissue-inductive proteins) that will ultimately enhance tissue development.

In certain preferred embodiments, the three-dimensional structural matrices are composed of poly(lactic-co-glycolic acid) (PLGA) that has been fabricated in a manner effective to control the pore size and structure by the processing technique. These structural matrices create a space and provide suitable stability to allow interacting cells to form new three dimensional tissues. The preferred fabrication process involves a gas foaming/particulate leaching (GF-PL) technique that does not use organic solvents or high temperatures.

The processing conditions for preparation of the matrix can be varied to produce matrices with either an open pore, a closed pore structure, or a combination of open and closed pores. The pore structure is a major design criteria, as it controls the ability of cells to invade the polymeric matrix following implantation (Mooney and Langer, 1995). This control over the rate of cellular invasion into the matrix is an important feature of the present invention.

The matrices can also be fabricated with a variety of copolymers of lactide and glycolide, allowing the polymer composition and molecular weight to control the degradation rate of the matrix. As the degradation rate of the polymer is varied, the rate of plasmid provision or delivery will change. Hence, the provision or delivery rate can be controlled. This, in turn, affects the time over which the incoming cells are newly exposed to plasmid DNA. The matrices thus have "variable biodegradability", wherein a "biodegradable" matrix is generally defined as one that is capable of ultimately being resorbed into the body.

Using copolymers of lactide and glycolide allows matrices to be fabricated that permit the time period of nucleic acid provision from the matrix to be varied. This depends, in part, on the molecular weight of the polymer and the composition ratio of lactic acid/glycolic acid. Generally, a higher ratio of lactic acid/glycolic acid, such as for example 75/25, will provide for a longer period of controlled or sustained provision or release of the nucleic acids, whereas a lower ratio of lactic acid/glycolic acid will provide for more rapid provision or release of the nucleic acids.

In terms of the molecular weight of the polymer, generally a higher molecular weight polymer will provide for a longer period of controlled or sustained provision or release. By way of example only, as a reference, when the composition ratio of lactic acid/glycolic acid is 100/0, the preferable average molecular weight of polymer ranges from about 7,000 to 25,000; when 90/10, from about 6,000 to 30,000; and when 80/20, from about 12,000 to 30,000. The i.v. (intrinsic viscosity) terminology used in the art as a measure of molecular weight can also be applied to the polymers of the present invention. A range of polymers with different intrinsic viscosities may be employed, as exemplified by i.v.=0.2 and, more preferably, by i.v.=0.7 polymeric matrices.

One aspect of these novel approaches involves fabricating three-dimensional matrices from microspheres that are loaded with the nucleic acids that are to be provided from the matrix. Incorporating DNA within a polymeric structure in particle form, e.g., as beads or microspheres, or blended with other polymers or molecules, is therefore an important aspect of the invention. This is exemplified by the incorporation of nucleic acids, optionally with other biological factors, into microspheres of poly (lactide-co-glycolide) utilizing an atomization/extraction process operated at cryogenic temperatures. Three-dimensional matrices are then fabricated using gas a foaming/particulate leaching process.

These approaches provide high incorporation efficiencies and a sustained provision or release of functional biological factors, particularly nucleic acids. Provision or release of the nucleic acids can be controlled in part through the microsphere fabrication process. Also, the microspheres can be formed from polymers or copolymers (e.g., PLGA) that degrade at different rates, or combinations of microspheres can be employed to give defined matrix regions that degrade at a rate different to the polymer or copolymer utilized to form the bulk of the matrix. Polymers or copolymers such as PLGA may also be combined with alginates or modified alginates to achieve similar differential control.

Such systems provide an additional level of control over the DNA release kinetics from the matrices. This gives additional control over their bioactivity, as genes contained within the microsphere-derived polymeric structure can be designed to provide a controlled provision or release effect therefrom in addition to the release kinetics provided by the matrix. The bioavailability in this situation will likely be controlled by either disassociation of the DNA from the bead, release from the PLGA, or both. Thus, a high degree of control over bioavailability and release kinetics is provided over a potentially wide range.

Further, multiple genes can be included in a matrix (in multiple types of the described particles and/or in polymer comprising the bulk of matrix) that will become available or released at varying times. This will be useful to create a cascade of different protein production, or waves of release of the same protein (e.g., for use in immunizations). Incorporation of DNA into such particles (e.g., alginate beads) may also be more suitable for maintaining long-term bioactivity than immobilization directly in the polymer comprising the bulk of foamed matrix.

For example, the present invention provides matrices fabricated from combinations of polymers and bioactive nucleic acids and/or factors to provide spatial and temporal control of release and bioavailability. This includes matrices fabricated from microspheres composed of different PLG copolymers, with each copolymer loaded with a different nucleic acid and/or bioactive factor. Variations in the PLG co-polymer affect the polymer degradation and thus the time course of nucleic acid provision and release. Also, the microsphere fabrication rate can be varied to control the release of the nucleic acids and/or factors. The entire variety of porous and solid outer wall-bounded matrices may be constructed by these processes. Thus, the spatial and temporal control over release provided by these fabrication methods is significant, meaning that the nucleic acid-matrices can be used in the treatment of a wide variety of disorders and injuries that occur in a number of tissues.

Nondegradable polymers, or matrices comprised partly of nondegradable polymers, are intended for use in situations in which permanent implants, or portions thereof, are desired. Additionally, some matrix materials are not degraded, but are remodeled. For example, hydroxyapatite is not degraded, but is used by osteoblasts and used to remodel new bone. Such materials can be combined with the GF/PL matrix-DNA compositions of the present invention, or used in conjunction therewith, e.g., in various implantable devices.

The porous types of structural matrices are much preferred in the invention. Virtually any type of porous structural matrix may be used in the broadest aspects of the invention. Matrices formed by solvent cast and particulate leaching techniques, as well as phase inversion and other porous scaffold fabrication techniques, can therefore be employed. Controlled pore matrices formed by GF/PL are particularly preferred, as described.

In certain other embodiments, the three-dimensional structural matrices for use in the invention are alginate or other hydrogel matrices. Until recently, alginate was typically used in the physical form of a hydrogel, with small pores (nm size scale) that do not allow for cell movement in or out of the material. Therefore, where the present invention contemplates alginate and other hydrogels, modified or porous alginates and hydrogels are particularly envisioned.

Alginates modified so that they have controllable physical properties, such as sol-gel properties, and the like, are one such form contemplated. Alginates comprising at least one alginate chain section bonded to at least one molecule useful for cellular interaction (cell adhesion molecules, cell attachment peptides, proteoglycan attachment peptide sequences, proteoglycans, and polysaccharides exhibiting cell adhesion) are thus envisioned. The modified alginates of Example XIX are examples of the alginates contemplated.

In preferred aspects of using alginates and hydrogels in the invention, the structural matrices are composed of alginates or hydrogels that have been fabricated in a manner effective to control the pore size and structure by the processing technique. Preferred methods of fabricating such alginate and hydrogel matrices also involve a technique that creates gas pockets in the gel and then removes the gas. The removal of the gas creates a porous material, and the initial incorporation of sufficient gas allows one to create a material with an open, interconnected pore structure. Advantageous features of the resulting materials, in addition to their interconnected pore structure, include that the pore structure is maintained over extended time periods and that the gels maintain a high mechanical integrity that allows biological implantation without destruction or compression of the material.

Irrespective of the choice of controlled, structural matrix material, the DNA-matrices of the invention can be prepared to yield different quantities of plasmid DNA, from a relatively short delivery time, i.e., a pulse, to a sustained delivery over a number of months or even years. Changing the polymer type is the preferred mechanism for changing the length of time of DNA delivery in general. The choice of polymer type can also be used to control the length of time that an impermeable layer is maintained in the body. This can therefore be used to control the rate of DNA provision or release from certain portions of the matrices or devices, in order to give a "spatially controlled provision or release", as may be used, e.g., to preferentially provide or release the genetic material in the vicinity of a certain target cell population.

The inventors have already demonstrated a sustained, continuous release of plasmid DNA from structurally controlled matrices (Example XIV, Example XVIII and Example XX), and have further shown that this plasmid DNA is intact and capable of transfecting cells in vitro (Example XV). Importantly, implantation of the DNA-releasing matrices leads to transfection of the cells within and surrounding the matrix in vivo (Example XVI and Example XVII).

Matrix-mediated provision (delivery) of a plasmid encoding for platelet-derived growth factor (PDGF), a potent factor in tissue repair, is used herein to significantly enhance granulation tissue deposition and blood vessel growth in developing tissues (Example XVII). This result is in marked contrast to direct injection of the same PDGF plasmid, which did not stimulate tissue formation (Example XVII). Such results demonstrate that the make-up and structure of engineered tissues can be controlled in vivo using the present invention.

The foregoing results confirm that the present invention can be effectively used in multiple applications, including tissue engineering and regeneration, and other gene therapy applications, such as DNA vaccination and correction of metabolic deficiencies via gene therapy.

A. Structurally Controlled Matrices

1. Controlled Pore Matrices

The present invention allows DNA to be utilized for tissue engineering applications as it provides techniques to deliver stable plasmids that transfect sufficient cells to produce inductive doses of desired proteins. One set of matrices preferred for use in the invention are polymers processed utilizing high pressure gas foaming. This provides a means of efficient plasmid DNA incorporation into polymeric matrices, and a controlled and sustained provision or delivery of plasmid DNA.

The inventive approach, in contrast to other approaches previously developed to fabricate three-dimensional matrices from biodegradable polymers (Peters and Mooney, 1998), utilizes neither organic solvents nor high temperatures in the polymer processing. Residual organic solvents in solvent-processed matrices may decrease the activity of incorporated factors or promote inflammatory responses in vivo, and high temperatures will similarly inactivate many biologically active molecules contained within the matrix.

The preferred processes for matrix generation are thus termed "GF/PL processes" (gas foaming/particulate leaching processes), as opposed to the less adequate solvent-casting/particulate leaching (SC/PL) processes used prior to the invention. The entire text and figures of U.S. patent application Ser. No. 09/402,119, filed Sep. 20, 1999, now U.S. Pat. No. 6,281,256, PCT Application No. PCT/US98/06188 (WO 98/44027), filed Mar. 31, 1998, which designates the United States, and U.S. Provisional Application Ser. No. 60/042,198, filed Mar. 31, 1997, the priority document for U.S. Pat. Nos. 6,281,256 and 6,797,738 and WO 98/44027, are also each specifically incorporated herein by reference without disclaimer for the purposes of even more fully describing matrix generation using GF/PL processes.

While materials prepared by an SC/PL process can also provide some extent of an interconnected pore matrix, the inventors have discovered that the materials prepared by the inventive GF/PL process exhibit a distinct pore structure and significantly advantageous mechanical properties over SC/PL prepared materials. This advantage is in addition to the absence of organic solvents and/or high temperatures in preparation of the material and the absence of organic solvent residue in the prepared materials. For example, the materials of the invention exhibit much higher strength properties, e.g., tensile strength.

While not intending to be bound by this theory, it is reasonably hypothesized that the improved mechanical properties and stronger matrix of the materials prepared by the inventors' GF/PL process result, at least in part, from greater uniformity of polymer distribution in the materials and/or greater uniformity in size and distribution of porosity in the materials. SC/PL prepared polymers will not have such a uniform pore structure because the solvent evaporates from the polymer in a non-uniform manner and thus the polymer concentration changes non-uniformly in the material. For instance, SC/PL materials typically have non-uniformity because as the solvent evaporates the polymer concentration increases at the bottom of the matrix, i.e. the area where the matrix touches the glass cover slip. In contrast, the GF/PL materials exhibit a very uniform pore structure indicating that the polymer foams uniformly throughout the particulate bed during the gas-foaming step.

Alternatively, it is hypothesized that in the GF/PL process the mechanical properties may be enhanced by tensile alignment of the polymer chains may be occurring during the elongation that occurs during foaming (Mooney et al., 1997).

In any event, it is of great advantage in tissue engineering, biodelivery and other applications that the materials of the invention have maximized tensile strength and compression resistance. This allows the materials to be handled and manipulated without mechanical breakdown and provides for better survival during use, particularly in the in vivo environment.

The following embodiment is provided as a representative, non-limiting, example of the matrix preparation aspects of the invention. Discs comprised of polymer (e.g., poly[D,L-lactic-co-glycolic acid]) and NaCl particles were compression molded at room temperature, and subsequently allowed to equilibrate with high pressure $CO_2$ gas (800 psi). Creation of a thermodynamic instability led to the nucleation and growth of gas pores in the polymer particles, and the formation of a continuous polymer matrix. The NaCl particles were subsequently leached to yield macropores, and a macropore structure. The overall porosity and level of pore connectivity was regulated by the ratio of polymer:salt particles.

Both the compressive modulus (159±130 kPa for SC/PL vs. 289±25 kPa for GF/PL) and tensile modulus (334±52 kPa for SC/PL vs. 1100±236 kPa for GF/PL) of matrices formed with this approach were significantly greater than those formed with a standard solvent casting/particulate leaching process. The potential of these matrices for engineering new tissue was demonstrated by finding that smooth muscle cells readily adhered and proliferated on these matrices, forming new, high density tissues ($3 \times 10^7$ cells/ml) in culture.

The overall novel process, a combination of high pressure gas foaming and particulate leaching techniques, allows one to fabricate matrices from biodegradable polymers with a well controlled porosity and pore structure. The materials prepared by the process of the invention exhibit a wide range of utilities, and may be applied to any use that requires a porous polymeric material, particularly with an open pore structure.

The term "biocompatible matrix", as used herein, means that the matrix has all the features commonly associated with being "biocompatible", in that it is in a form that does not produce a significant adverse, allergic or other untoward reaction when administered to an animal. The materials of the present invention have improved biocompatibility in that organic solvents are not required for their manufacture. This is important as the present materials are intended for bioapplications wherein organic solvent residue is not tolerable.

For example, the materials are useful as matrices for in vitro cell culture in which cells are compatible and grow to achieve their intended function, such as in tissue replacement, eventually replacing the matrix depending on its biodegradability. The stable structures of the materials of the invention thus provide ideal cell culture conditions. Furthermore, the materials can be used to provide matrices already bound to cells, which may then be surgically implanted into a body.

The materials of the invention prepared by the GF/PL process generally further have applications similar to those of materials prepared by the SC/PL and phase separation techniques, for example, in a variety of cell transplantation applications, including for hepatocytes (Mooney et al., 1994; Mooney et al., 1995; incorporated herein by reference) chondrocytes and osteoblasts (Ishaug, et al., 1994; incorporated herein by reference). However, the materials of the invention have better mechanical properties and avoid the problem of organic solvent residue that may damage transplanted or migrating cells and nearby tissue and/or inactivate biologically active factors.

Smooth muscle cells readily adhere to the matrix material of the invention and create three-dimensional tissues within these porous structures; thus, they provide a suitable environment for cell proliferation. In vitro studies have already indicated concentrated cell growth around the periphery of a sponge matrix, with the peripheral concentration likely being due to less $O_2$ diffusion to cells at the center of the matrix in view of the thickness (3.4 mm) of the sponge used.

This invention also allows the preparation of polymers, such as polymeric sponges, that have an impermeable layer on one side, thus providing a selective permeability feature.

The impermeable layer is composed of the same polymers but without the extent of porosity, and a variety of methods can be used to couple the impermeable layer to, e.g., a polymeric sponge.

In a particular embodiment that is representative of this utility, the polymeric sponge is created by grinding PLGA followed by sieving to obtain particles with a diameter between about 108 and about 250 microns. These polymeric particles are mixed with sodium chloride and pressed into shape with a die at a pressure of approximately 1500 psi. The polymer/salt solid is then foamed by placing the solid in a pressure bomb and exposing it to $CO_2$ at a pressure of about 800 psi for about 48 h followed by a relatively rapid reduction in pressure. This reduction in pressure produces thermodynamic instabilities in distribution of $CO_2$ causing pore formation. The polymer/salt solid is then placed in water for 24 h to leach out the salt. Note that the water is changed during the leaching process. This process produces a polymer sponge that is greater than 95% porous. The degradation rate of the sponge can be modified by varying the composition of lactic and glycolic acid.

An impermeable layer can be created on one side of the sponge by one of the following techniques, preferably performed before gas foaming of the material. The sponge can be pressed into shape on a layer of PGA at a temperature greater than the melting temperature for PGA. The melted PGA will be able to adhere to the sponge thus forming a thin layer. This layer is impermeable because the foaming process and the leaching process have a negligible effect on pure PGA. An impermeable layer of PLGA can also be created on the sponge by pressing the sponge onto a layer of PLGA. Spraying a solution of PLA in chloroform onto one side of the sponge can also create an impermeable layer.

Furthermore, it is possible to use the same polymer material and alter the amount of leachable particulate in each section so that one section forms an open pore structure and one does not. Also, by using different polymers, materials wherein one section foams, and the impermeable layer section does not, can be provided. Although PLGA does foam following release of pressure from the bomb, an impermeable skin forms on the thin layer of PLGA that remains intact during the leaching process. Alternatively, following the foaming and leaching process, the polymeric sponge can be dipped in either melted PGA or in a solution of PLGA in chloroform. These procedures can be used to create a sponge that has a porosity of greater than 95% with an impermeable side.

Another useful application for the polymer matrices of the invention is for guided tissue regeneration (GTR). This application is based on inducing the progenitor cells that reside in the underlying healthy tissue, and that are responsible for tissue regeneration, to migrate into a defect and regenerate the lost tissue. An important feature of matrices for GTR is the transport of cells into the matrix, a property that is dictated by the pore size distribution and pore continuity, i.e. interconnectivity. The chosen matrix will therefore allow the desired cells to invade the matrix, while preferably preventing access to other cell types.

Another potential application of the matrix and sponge materials for GTR is for the treatment of periodontal disease. Periodontal disease is characterized by the loss of attachment of the periodontal ligament to the alveolar bone. The epithelial cells of the gingiva begin to grow into the site where the periodontal ligament was attached. A sponge of the matrix material according to the invention with an impermeable side may be used to prevent the downgrowth of epithelial cells while allowing the appropriate cells to occupy the porous sponge, thereby regenerating the periodontal ligament (Shea et al., 1977).

In light of the absence of organic solvents from the foregoing matrices, the residue of which would remain in the polymers and would damage nearby cells and tissues, the inventors decided to explore the potential for incorporating biologically active factors into the matrices. In addition to their use in drug and growth factor delivery, the inventors contemplated that the unique matrix materials could prove useful in the provision or delivery of genetic material. However, the ability of such matrices to provide sustained bioavailable DNA that maintained its structural and functional integrity, and particularly their ability to mediate gene transfer and functional expression, surpassed reasonable expectations.

The ability to control the rate of plasmid provision or release over a wide range of times, by mechanisms other than desorption from the matrix, and yet to achieve sufficient provision or release for gene transfer and expression, is a particular benefit of the invention. One of the mechanisms for achieving such control involves matrix fabrication from microspheres containing nucleic acids, e.g., made by atomization/extraction processes operated at cryogenic temperatures. Fabrication of these materials into three-dimensional matrix using gas foaming/particulate leaching is efficient and provides for sustained nucleic acid provision. The matrices fabricated from nucleic acid-containing microspheres can be used in virtually any application in which a controlled provision or delivery of bioactive factors is desired, including drug delivery, gene therapy, and tissue engineering.

2. Porous Hydrogel Matrices

In certain other preferred embodiments, the three-dimensional structural matrices for use in the invention are composed of alginates or hydrogels that have pore sizes and structures controlled by the processing technique. These structural matrices also create a space and provide suitable stability to allow interacting cells to form new three dimensional tissues.

The preferred fabrication processes for such alginate and hydrogel matrices involve techniques that create gas pockets in the gel and then remove the gas. This generates porous materials with open, interconnected pore structures and high mechanical integrity. These alginate and hydrogel structures therefore have a "sufficient degree of porosity" or a "sufficiently open interconnected pore structure". Such alginate and hydrogel materials may be described as having a significantly macroporous and open pore structure, e.g., such that the pores are sufficiently open and sized to allow cellular transport therein. Thus, the macroporous alginates and hydrogels will preferably have pores of at least 1 µm, particularly from 10 to 1000 µm. While not limited thereto, the overall porosity may be from 35 to 75%.

Methods for preparing such alginate or other hydrogel materials having macroporous open pore porosity, generally comprise:
  (a) providing a solution of a hydrogel-forming material and a surfactant;
  (b) mixing the solution in the presence of a gas to form a stable foam;
  (c) exposing the stable foam to conditions and/or agents that result in gelling of the hydrogel-forming material and in the generation of gas bubbles therein; and
  (d) exposing the hydrogel containing gas bubbles to a vacuum to release the gas and form the hydrogel material having macroporous open pore porosity.

The methods may be further described as comprising:
(a) providing a solution of a hydrogel-forming material, a surfactant and, optionally, a gas-generating component;
(b) mixing the solution in the presence of a gas to form a stable foam;
(c) exposing the stable foam to conditions and/or agents that result in gelling of the hydrogel-forming material and, if the gas-generating component is present, to conditions or agents that result in generation of gas from the gas-generating component, to form a hydrogel containing gas bubbles therein; and
(d) exposing the hydrogel containing gas bubbles therein to a vacuum to release the gas and to form the hydrogel material having macroporous open pore porosity.

The methods may be even further described as comprising:
(a) providing a solution of a hydrogel-forming material, a surfactant and a gas-generating component, which solution is capable of being mixed in the presence of a gas to incorporate the gas in the solution and form a stable foam;
(b) mixing the solution in the presence of a gas to form a stable foam;
(c) exposing the stable foam to conditions and/or agents that result in gelling of the hydrogel-forming material and to conditions or agents that result in generation of gas from the gas-generating component, to form a hydrogel containing gas bubbles therein; and
(d) exposing the hydrogel containing gas bubbles therein to a vacuum to release the gas and to form the hydrogel material having macroporous open pore porosity.

Any hydrogel-forming material that can provide the desired effect of resulting in a foam that allows preparation of the open pore material can be used in these aspects of the invention. Examples of materials that can form hydrogels include polylactic acid, polyglycolic acid, PLGA polymers and copolymers; alginates and alginate derivatives; gelatin; collagen; agarose; natural and synthetic polysaccharides; polyamino acids, such as polypeptides, particularly poly(l-ysine); polyesters, such as polyhydroxybutyrate and poly-$\epsilon$-caprolactone; polyanhydrides; polyphosphazines; poly(vinyl alcohols); poly(alkylene oxides), particularly poly(ethylene oxides); poly(allylamines) (PAM); poly(acrylates); modified styrene polymers, such as poly(4-aminomethylstyrene); pluronic polyols; polyoxamers; poly(uronic acids); poly(vinylpyrrolidone); and copolymers of the above, including graft copolymers.

A preferred material for the hydrogel is alginate or modified alginate material. Alginate molecules are comprised of (1-4)-linked $\beta$-D-mannuronic acid (M units) and $\alpha$-L-guluronic acid (G units) monomers, which vary in proportion and sequential distribution along the polymer chain. Alginate polysaccharides are polyelectrolyte systems that have a strong affinity for divalent cations (e.g. $Ca^{+2}$, $Mg^{+2}$, $Ba^{+2}$) and form stable hydrogels when exposed to these molecules. Biomedical calcium cross-linked alginate hydrogels may be used as described in Hanks et al., (1993); Matthew et al., (1995); Atala et al., (1994); and Smidsrød et al., (1990); each incorporated herein by reference.

An alternative embodiment utilizes an alginate or other polysaccharide of a lower molecular weight and/or at about the renal threshold for clearance by humans. Preferably, the alginate or polysaccharide is reduced to a molecular weight of 1000 to 80,000 daltons, more preferably 1000 to 60,000 daltons. Alginate materials of high guluronate content are also useful, since the guluronate units, as opposed to the mannuronate units, provide sites for ionic crosslinking through divalent cations to gel the polymer.

The reduction in molecular weight can be effected by hydrolysis under acidic conditions or by oxidation, to provide the desired molecular weight. Hydrolysis can be conducted to result in a sodium poly(guluronate) of lower molecular weight that is essentially absent of mannuronic acid units. The oxidation to lower molecular weight is preferably conducted with a periodate oxidation agent, particularly sodium periodate (PCT/US97/16890% WO 98/12228).

For alginate materials, it is preferred to use starting solutions of alginate salt in an amount, for example, of about 3% to 10% w:w (weight based on weight of water), more preferably about 3% to 5% w:w. For other materials, the amount used in the starting solution will depend upon the material used, however, it is preferred to use at least about 3% w:w in the starting solution. This will preferably result in concentrations of the alginate or other hydrogel-forming material in the solution to be foamed of more than about 3% weight, particularly about 3-10%, more particularly, about 3-5%.

The "hydrogel-forming material" is the precursor, ungelled form of the hydrogel. It will be a soluble form of the hydrogel that is capable of being gelled by application of some condition or agent. For example, alginate salts, such as sodium alginate, are gelled in the presence of divalent cations, such as calcium present in calcium chloride. Other materials may be gellable by a change in pH or temperature, for example.

As the surfactant, any surfactant that will facilitate formation and stabilization of gas bubbles in the solution, without preventing the other steps of the method, can be used. Useful examples thereof include bovine serum albumin (BSA), the pluronic class of surfactants (e.g., F108 and F68), polyethylene glycol and propylene glycol alginate surfactants. The amount of surfactant used will depend on the amount and type of the hydrogel being formed and an amount that facilitates formation and stabilization of gas bubbles in the solution, without preventing the other steps of the method, can be used.

For use of BSA as the surfactant, the method may be conducted using a BSA concentration in the final solution to be foamed of about 0.05-1% weight. The amount used will depend on the amount of the alginate or other hydrogel material used. A BSA stock solution of about 1 to 10% weight BSA in water can be used for this purpose. For example, using about 2 grams of a 3 to 5% w:w of alginate, about 240 to 400 mg of a 15% solution of BSA has been found useful. The weight ratio of BSA to alginate may be from about 1:10 to about 1:60, preferably about 1:10 to about 1:20, for some applications, but it is not limited thereto.

If a gas-generating component is provided, it is preferred to use sodium bicarbonate, which will release carbon dioxide gas when exposed to a mild acid, for example, acetic acid. For this purpose, about a 10% volume acetic acid solution may be used, which provides at least an amount of acetic acid equimolar to the amount of sodium bicarbonate to be released. For example, the bicarbonate can be added in powder form or as a bicarbonate solution of 1.0M to 2.0M to provide a concentration of 0.5 to 5.0% weight in the solution to be foamed.

When using an alginate hydrogel and a BSA surfactant, it has further been found that the ratio of BSA to bicarbonate has an effect on the product. It is preferred in this case that the weight ratio of about 15% weight BSA solution to the about 1.0 to 2.0M bicarbonate solution is about 2:1 to 1:1.

Other materials that release gases upon application of some condition or agent may be used provided they will result in formation of gas bubbles in the hydrogel that are releasable upon application of a vacuum and do not otherwise interfere in the preparation.

A gas-generating component may not be necessary if the solution of hydrogel-forming material and surfactant can be mixed in the presence of gas to provide suitable gas bubbles in the resulting hydrogel. Preferably, the solution is mixed in the presence of air to result in the foaming and subsequent formation of air bubbles when the hydrogel is gelled. When a gas-generating component is used, the hydrogel may have gas bubbles of air provided by the mixing as well as gas bubbles generated by the gas-generating component. Any mixing means that results in adequate foaming can be used.

The stable foam resulting from mixing of the above-described solution is gelled in a manner dependent upon the hydrogel-forming material, e.g., by contact with a gelling agent or a change in pH or temperature. For alginate hydrogels, the gelling is effected by contact with divalent cations in solution, e.g., a calcium chloride solution of from about 0.1 to 1.0M, preferably about 0.5M.

The manner of exposing the solution to the gelling agent or condition will depend on the desired shape of the resulting porous hydrogel material. For example, hydrogel beads can be provided by adding the stable foam dropwise to a solution of the gelling agent, such as through a syringe or a syringe pump for scaled up applications. In a similar manner, the stable foam may be provided continuously through a syringe device to provide the porous hydrogel in a fibrous form.

The stable foam may also be cast in a desired shape and subject to the gelling agent or gelling condition to provide a shaped article, which may be particularly useful for tissue regeneration applications. Other forms of the material may be prepared using means available in the art.

In any event, the resulting hydrogel will contain gas bubbles and exposure thereof to a vacuum will draw out the entrapped gas bubbles to create an open pore macroporous hydrogel.

In one preferred embodiment, these processes involve first providing a solution of sodium alginate in water. Sodium bicarbonate and bovine serum albumin (BSA) are then added to this solution and mixed to allow for incorporation of air bubbles in the resulting solution to create a stable foam. This solution is then placed in a syringe and extruded dropwise into a stirred solution of calcium chloride and acetic acid in water (gelling solution). The calcium ions serve to gel the alginate, while the acetic acid reacts with the bicarbonate to generate carbon dioxide gas in the hydrogel. The gelled alginate in the form of microbeads is collected separately from the solution. The alginate is subsequently exposed to a vacuum to draw out the entrapped gas bubbles (both of air and carbon dioxide) and create the open pore structure.

It is important to note that as the hydrogel is varied the specific, optimal conditions will vary as well. For example, utilization of a lower molecular weight alginate will decrease the solution viscosity, necessitating a higher alginate concentration and/or higher BSA concentration, and vice versa. Varying the guluronic acid content of the alginate will alter the strength of the hydrogel and require either an increased vacuum to remove gas bubbles or a decreased starting alginate concentration. All such optimizations will be understood by one of ordinary skill in the art in light of the present disclosure.

B. Genes and DNA Segments

As used herein, the terms "nucleic acid" and "DNA segment" are generally used to refer to nucleic acids and DNA molecules that have been isolated free from total cell components, and often, free from total genomic DNA of a particular species. However, total genomic DNA or cellular nucleic acids are surprisingly useful in the present invention, particularly in transfer to antigen presenting cells, in DNA vaccination embodiments.

The nucleic acids to be combined with matrices, for use in the present invention, extend to the full variety of nucleic acid molecules. The nucleic acids thus include genomic DNA, cDNAs, single stranded DNA, double stranded DNA, triple stranded DNA, oligonucleotides, Z-DNA, mRNA, tRNA and other RNAs. DNA molecules are generally preferred, even where the DNA is used to express a therapeutic RNA, such as a ribozyme or antisense RNA.

A "gene" or DNA segment encoding a selected protein or RNA, generally refers to a DNA segment that contains sequences encoding the selected protein or RNA, but is isolated away from, or purified free from, total genomic DNA of the species from which the DNA is obtained. Included within the terms "gene" and "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

This invention provides novel ways in which to utilize various known DNA segments and recombinant vectors. However, there is no requirement that highly purified DNA or vectors be used, so long as any coding segment employed encodes a selected protein or RNA and does not include any coding or regulatory sequences that would have a significant adverse effect on the target cells. Therefore, it will also be understood that useful nucleic acid sequences may include additional residues, such as additional non-coding sequences flanking either of the 5' or 3' portions of the coding region or may include various internal sequences, i.e., introns, which are known to occur within genes.

Many suitable DNA segments may be obtained from existing, including commercial sources. One may also obtain a new DNA segment encoding a protein of interest using any one or more of a variety of molecular biological techniques generally known to those skilled in the art. For example, cDNA or genomic libraries may be screened using primers or probes with designed sequences. Polymerase chain reaction (PCR™) may also be used to generate a DNA fragment encoding a protein of interest.

After identifying an appropriate selected gene or DNA molecule, it may be inserted into any one of the many vectors currently known in the art, so that it will direct the expression and production of the selected protein when incorporated into a target cell. In a recombinant expression vector, the coding portion of the DNA segment is positioned under the control of a promoter/enhancer element. The promoter may be in the form of the promoter that is naturally associated with a selected gene, as may be obtained by isolating the 5' non-coding sequences located upstream of the coding segment or exon, for example, using recombinant cloning and/or PCR technology.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a selected gene in its natural environment. Such promoters may include those normally associated with other selected genes, and/or promoters isolated from any other bacterial, viral, eukaryotic, or mammalian cell. Naturally, it will be important to employ a promoter that effectively directs the expression of the DNA segment in the chosen target cells.

The use of recombinant promoters to achieve protein expression is generally known to those of skill in the art of molecular biology, for example, see Sambrook et al. (1989; incorporated herein by reference). The promoters employed may be constitutive, or inducible, and can be used under the appropriate conditions to direct high level or regulated expression of the introduced DNA segment. Expression of genes under the control of constitutive promoters does not require the presence of a specific substrate to induce gene expression and will occur under all conditions of cell growth. In contrast, expression of genes controlled by inducible promoters is responsive to the presence or absence of an inducing agent.

Promoters isolated from the genome of viruses that grow in mammalian cells, e.g., RSV, vaccinia virus 7.5K, SV40, HSV, adenoviruses MLP, MMTV LTR and CMV promoters, may be used herewith, as well as promoters produced by recombinant DNA or synthetic techniques. Currently preferred promoters are those such as CMV, RSV LTR, the SV40 promoter alone, and the SV40 promoter in combination with the SV40 enhancer.

Exemplary tissue specific promoter/enhancer elements and transcriptional control regions that exhibit tissue specificity include, but are not limited to: the elastase I gene control region that is active in pancreatic acinar cells; the insulin gene control region that is active in pancreatic β cells; the immunoglobulin gene control region that is active in lymphoid cells; the albumin, α1-antitrypsin and α-fetoprotein gene control regions that are active in liver; the β-globin gene control region that is active in myeloid cells; the myelin basic protein gene control region that is active in oligodendrocyte cells in the brain; the myosin light chain-2 gene control region that is active in skeletal muscle; and the gonadotropic releasing hormone gene control region that is active in the hypothalamus. U.S. application Ser. No. 08/631,334, filed Apr. 12, 1996, now U.S. Pat. No. 5,962,427 and PCT Application Serial No. PCT/US97/07301, filed Apr. 11, 1997, (WO 97/38729), are both incorporated herein by reference for the purposes of incorporating references even further describing the foregoing elements.

Specific initiation signals may also be required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon should be provided. The initiation codon must be in phase with the reading frame of the protein coding sequences to ensure translation of the entire insert. These exogenous translational control signals and initiation codons can be of a variety of origins, both natural and synthetic. The efficiency and control of expression may be enhanced by the inclusion of transcription attenuation sequences, enhancer elements, etc.

A variety of vectors may be used including, but not limited to, those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Vectors that allow for the in vitro transcription of RNA, such as SP6 vectors, may also be used to produce large quantities of RNA that may be incorporated into matrices.

The selected genes and DNA segments may also be in the form of a DNA insert located within the genome of a recombinant virus, such as, for example a recombinant herpes virus, retroviruses, vaccinia viruses, adenoviruses, adeno-associated viruses or bovine papilloma virus. While integrating vectors may be used, non-integrating systems, which do not transmit the gene product to daughter cells for many generations will often be preferred. In this way, the gene product is expressed during a defined biological process, e.g., a wound healing process, and as the gene is diluted out in progeny generations, the amount of expressed gene product is diminished.

In such embodiments, to place the gene in contact with a target cell, one would prepare the recombinant viral particles, the genome of which includes the gene insert, and simply contact the target cells or tissues with a matrix containing the virus, whereby the virus infects the cells and transfers the genetic material. The following U.S. patents are each incorporated herein by reference for even further exemplification of viral gene therapy: U.S. Pat. No. 5,747,469, concerning adenovirus, retrovirus, adeno-associated virus, herpes virus and cytomegalovirus gene therapy; U.S. Pat. No. 5,631,236, concerning adenovirus gene therapy; and U.S. Pat. No. 5,672, 344, concerning herpesvirus gene therapy.

Adenoviral vectors are particularly contemplated for use with the present gene-matrix invention. The technical side of the generation of adenoviral constructs is well known to those of ordinary skill in the art, as exemplified by the techniques described by Ghosh-Choudhury & Graham (1987); McGrory et. al. (1988); Gluzman et. al. (982); Rosenfeld et. al. (1991; 1992); and Stratford-Perricaudetet. al. (1990; 1992); each incorporated herein by reference.

Adenoviral vectors for use in connection with the invention will preferably be replication defective vectors. For example, as achieved through the deletion of the viral early region 1 (E1A) region such that the virus is competent to replicate only in cells, such as human 293 cells, which express adenovirus early region 1 genes from their cellular genome. This is important because the virus will therefore not kill normal cells that do not express early gene products.

Using vectors that do not have an adenovirus E1 region, it will be most convenient to introduce a new coding region at the position from which the E1 coding sequences have been removed. However, the position of insertion of a gene within the adenovirus sequences is not critical to the present invention. Transcription units may also be inserted in lieu of the deleted E3 region in E3 replacement vectors, as previously by Karlsson et. al. (1986).

Other than the requirement that the adenovirus vector be replication defective, the nature of the adenovirus vector is not believed to be crucial to the successful practice of the invention. The adenovirus may be of any of the 42 different known serotypes or subgroups A-F. Adenovirus type 5 of subgroup C may be preferred for use with the present invention. This is because Adenovirus type 5 is a human adenovirus about which a great deal of biochemical and genetic information is known, and it has historically been used for most constructions employing adenovirus as a vector.

As with all expression constructs for use with the invention, the promoter used in connection with adenoviral expression is not critical. The human cytomegalovirus (CMV) immediate early gene promoter may be used (Thomsen et. al., 1984), which results in the constitutive, high-level expression of foreign genes. However, other viral and mammalian cellular promoters are also suitable, provided that the levels of expression are sufficient to achieve a physiologic effect, where desired. Selection of a promoter specifically active in a given tissue is naturally an option. Choice of a promoter that is regulated in response to specific physiological signals also permits inducible expression of the gene in response to certain stimuli.

Genes with sequences that vary from those described in the literature are also contemplated for use in the invention, so long as the altered or modified gene still encodes a protein that functions to effect the target cells in the desired (direct or indirect) manner. These sequences include those caused by point mutations, those due to the degeneracies of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the activity of a protein, to increase its biological stability or half-life, to change its glycosylation pattern, confer temperature sensitivity or to alter the expression pattern of the protein, and the like. All such modifications to the nucleotide sequences are encompassed by this invention.

It is an advantage of the present invention that one or more than one selected gene may be used in the gene transfer methods and compositions. The nucleic acid delivery methods may thus entail the administration of one, two, three, or more, selected genes. The maximum number of genes that may be applied is limited only by practical considerations, such as the effort involved in simultaneously preparing a large number of gene constructs or even the possibility of eliciting an adverse cytotoxic effect. The particular combination of genes may be chosen to alter the same, or different, biochemical pathways. For example, a growth factor gene may be combined with a hormone gene; or a first hormone and/or growth factor gene may be combined with a gene encoding a cell surface receptor capable of interacting with the polypeptide product of the first gene.

In using multiple genes, they may be combined on a single genetic construct under control of one or more promoters, or they may be prepared as separate constructs of the same of different types. Thus, an almost endless combination of different genes and genetic constructs may be employed. Certain gene combinations may be designed to, or their use may otherwise result in, achieving synergistic effects on cell stimulation and tissue growth, and any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic segment or gene could be administered in combination with further agents, such as, e.g. proteins or polypeptides or various pharmaceutically active agents. So long as genetic material forms part of the composition, there is virtually no limit to other components which may also be included, given that the additional agents do not cause a significant adverse effect upon contact with the target cells or tissues. The nucleic acids may thus be delivered along with various other agents, for example, in certain embodiments one may wish to administer an angiogenic factor, and/or an inhibitor of bone resorption, as disclosed in U.S. Pat. Nos. 5,270,300 and 5,118,667, respectively, each incorporated herein by reference.

As the chemical nature of genes, i.e., as a string of nucleotides, is essentially invariant, and as the process of gene transfer and expression are fundamentally the same, it will be understood that the type of genes transferred by the controlled pore matrices of the present invention is virtually limitless. This extends from the transfer of a mixture of genetic material expressing antigenic or immunogenic fragments for use in DNA vaccination; to the stimulation of cell function, as in wound-healing; to aspects of cell killing, such as in transferring tumor suppressor genes, antisense oncogenes or apoptosis-inducing genes to cancer cells.

Various, entirely non-limiting aspects of the invention are exemplified by the wound-healing and bone stimulation embodiments described below.

1. Wound-Healing Genes

U.S. application Ser. No. 08/199,780, filed Feb. 18, 1994, now U.S. Pat. No. 5,763,416; U.S. application Ser. No. 08/631,334, filed Apr. 12, 1996, now U.S. Pat. No. 5,962,427; and PCT Application Serial No. PCT/US97/07301, filed Apr. 11, 1997, (WO 97/38729); each incorporated herein by reference, describe applications of the invention to in vivo methods for targeting and transfer of DNA into mammalian repair cells.

These aspects of the invention are based on the discovery that mammalian repair cells proliferate and migrate into a wound site, where they actively take up and express DNA. DNA-matrix combinations may thus be provided to incorporate a therapeutic protein of interest into a repair cell. In the practice of the invention, repair cells that normally originate in viable tissue surrounding the wound, proliferate and migrate into the gene activated matrix, wherein they encounter, take up and express the DNA. Transfected repair cells therefore act as in situ bioreactors (localized within the wound site) that produce agents (DNA-encoded RNAs, proteins, etc.) that heal the wound.

The nucleic acids to be used in the practice of these aspects of the invention may include any DNA encoding translational products (i.e., proteins) or transcriptional products (i.e., antisense or ribozymes) that promote tissue repair or that are capable of disrupting a disease process. For example, the DNA may comprise genes encoding therapeutically useful proteins, such as growth factors, cytokines, hormones, etc. Additionally, the DNA may encode antisense or ribozyme molecules that inhibit the translation of mRNAs encoding proteins that inhibit wound healing, or that induce excess inflammation.

The expression of antisense RNA molecules will generally act to directly block the translation of mRNA by binding to targeted mRNA and preventing protein translation. The expression of ribozymes, which are enzymatic RNA molecules capable of catalyzing the specific cleavage of RNA, may also be used to block protein translation. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of RNA sequences. RNA molecules may be generated by transcription of DNA sequences encoding the RNA molecule.

DNA molecules that code for factors that promote wound healing include DNAs encoding extracellular, cell surface, and intracellular RNAs and proteins. Examples of suitable extracellular proteins include growth factors, cytokines, therapeutic proteins, systemic and local hormones and active fragments of hormones, inhibitors of cytokines, peptide growth and differentiation factors, interleukins, chemokines, interferons, colony stimulating factors and angiogenic factors.

Particular examples of such proteins include, but are not limited to, the superfamily of TGF-β molecules, including the five TGF-β isoforms and bone morphogenetic proteins (BMP), latent TGF-β binding proteins, LTBP; keratinocyte growth factor (KGF); hepatocyte growth factor (HGF); platelet derived growth factor (PDGF); insulin-like growth factor (IGF); macrophage-colony stimulating factor (M-CSF); acidic fibroblast growth factor (FGF); the basic fibroblast growth factors, FGF-1, FGF-2 etc.; vascular endothelial growth factor (VEGF); Factor VIII and Factor IX; erythropoietin (EPO); tissue plasminogen activator (TPA); activins and inhibins.

Hormone genes that may be used in the practice of the invention include those that encode growth hormone (GH) and calcium regulatory agents, such as parathyroid hormone (PTH). Examples of extracellular proteins also include the extracellular matrix proteins such as collagen, laminin, and fibronectin.

Examples of cell surface proteins include the family of cell adhesion molecules (e.g., the integrins, selectins, Ig family members such as N-CAM and L1, and cadherins); cytokine signaling receptors, such as the type I and type II TGF-β receptors and the FGF receptor; and non-signaling co-receptors such as betaglycan and syndecan.

Examples of intracellular RNAs and proteins include the family of signal transducing kinases; cytoskeletal proteins, such as talin and vinculin; cytokine binding proteins, such as the family of latent TGF-β binding proteins; and nuclear trans acting proteins such as transcription factors and enhancing factors.

The wound healing DNA molecules may also code for proteins that block pathological processes, thereby allowing the natural wound healing process to occur unimpeded. Examples of blocking factors include ribozymes that destroy RNA function and DNAs that, for example, code for tissue inhibitors of enzymes that destroy tissue integrity, e.g., inhibitors of metalloproteinases associated with arthritis.

2. Osteogenic Genes

As described in U.S. application Ser. No. 08/199,780, filed Feb. 18, 1994, now U.S. Pat. No. 5,763,416; U.S. application Ser. No. 08/631,334, filed Apr. 12, 1996, now U.S. Pat. No. 5,962,427; and PCT Application Serial No. PCT/US97/07301, filed Apr. 11, 1997, (WO 97/38729); each incorporated herein by reference for this purpose, the present invention may be used in conjunction with one or more osteogenic or osteotropic genes.

As used herein, the terms "osteogenic and osteotropic gene" are used to refer to a gene or DNA coding region that encodes a protein, polypeptide or peptide that is capable of promoting, or assisting in the promotion of, bone formation, or one that increases the rate of primary bone growth or healing (or even a gene that increases the rate of skeletal connective tissue growth or healing). The terms promoting, inducing and stimulating are used interchangeably throughout this text to refer to direct or indirect processes that ultimately result in the formation of new bone tissue or in an increased rate of bone repair. Thus, an osteogenic gene is a gene that, when expressed, causes the phenotype of a cell to change so that the cell either differentiates, stimulates other cells to differentiate, attracts bone-forming cells, or otherwise functions in a manner that ultimately gives rise to new bone tissue.

In using the new osteotomy model of the invention, an osteogenic gene is characterized as a gene that is capable of stimulating proper bone growth in the osteotomy gap to any degree higher than that observed in control studies, e.g., parallel studies employing an irrelevant marker gene such as β-galactosidase. This stimulation of "proper bone growth" includes both the type of tissue growth and the rate of bone formation. In using the model with a 5 mm osteotomy gap, an osteogenic gene is generally characterized as a gene that is capable of promoting or inducing new bone formation, rather than abnormal bone fracture repair, i.e. fibrous non-union. In using the 2 mm osteotomy gap, one may characterize osteogenic genes as genes that increase the rate of primary bone healing as compared to controls, and more preferably, genes capable of stimulating repair of the osteotomy defect in a time period of less than nine weeks.

In general terms, an osteogenic gene may also be characterized as a gene capable of stimulating the growth or regeneration of skeletal connective tissues such as, e.g., tendon, cartilage, and ligament. Thus, in certain embodiments, the methods and compositions of the invention may be employed to stimulate the growth or repair of both bone tissue itself and also of skeletal connective tissues.

A variety of osteogenic genes are now known, all of which are suitable for use in connection with the present invention. Osteogenic genes and the proteins that they encode include, for example, systemic hormones, such as parathyroid hormone (PTH) and estrogen; many different growth factors and cytokines; chemotactic or adhesive peptides or polypeptides; molecules such as activin (U.S. Pat. No. 5,208,219, incorporated herein by reference); specific bone morphogenetic proteins (BMPs); and even growth factor receptor genes.

Examples of suitable osteogenic growth factors include those of the transforming growth factor (TGF) gene family, including TGFs 1-4, and particularly TGF-β1, TGF-β2 and TGF-β2, (U.S. Pat. Nos. 4,886,747 and 4,742,003, incorporated herein by reference), with TGF-α (U.S. Pat. No. 5,168,051, incorporated herein by reference) also being of possible use; and also fibroblast growth factors (FGF), such as acidic FGF and bFGF; granulocyte/macrophage colony stimulating factor (GMCSF); epidermal growth factor (EGF); platelet derived growth factor (PDGF); insulin-like growth factors (IGF), including IGF-I and IGF-II; and leukemia inhibitory factor (LIF), also known as HILDA and DIA. Any of the above or other related genes, or DNA segments encoding the active portions of such proteins, may be used in the novel methods and compositions of the invention.

Certain preferred osteogenic genes and DNA segments are PTH, those of the TGF superfamily, such as TGF-β1, TGF-β2, TGF-β3, and members of the BMP family of genes. TGF genes are described in U.S. Pat. Nos. 5,168,051; 4,886,747 and 4,742,003, each incorporated herein by reference. TGFα may not be as widely applicable as TGFβ, but is proposed for use particularly in applications involving skeletal soft tissues.

Several BMP genes that have already been cloned may be used in the nucleic acid transfer and delivery protocols of the invention. Suitable BMP genes are those designated BMP-2 through BMP-15. BMP-1 is not considered to be particularly useful at this stage. The DNA sequences for several BMP (or OP) genes have been described both in scientific articles and in U.S. patents such as U.S. Pat. Nos. 4,877,864; 4,968,590; 5,108,753; and 5,700,774; each incorporated herein by reference.

Specifically, BMP-1 sequences are disclosed in U.S. Pat. No. 5,108,922; BMP-2A (also referred to as BMP-2) in U.S. Pat. Nos. 5,166,058, 5,631,142, 5,618,924 and 5,013,649; BMP-2B (also referred to as BMP-4) in U.S. Pat. Nos. 5,013, 649, 5,618,924 and 5,399,677, the latter including mutant sequences; BMP-3 in U.S. Pat. No. 5,116,738; BMP-5 in U.S. Pat. Nos. 5,106,748, 5,543,394, 5,635,373 and 5,399,677, the latter including mutant sequences; BMP-6 in U.S. Pat. Nos. 5,187,076, 5,399,677 (including mutants) and 5,459,047; BMP-7 in U.S. Pat. Nos. 5,108,753, 5,366,875, 5,399,677 (including mutants) and 5,141,905; BMP-8 in U.S. Pat. No. 5,688,678; BMP-9 in U.S. Pat. No. 5,661,007; BMP-10 in U.S. Pat. Nos. 5,637,480 and 5,703,043; BMP-11 in U.S. Pat. Nos. 5,639,638 and 5,700,911; BMP-12 in U.S. Pat. No. 5,658,882; BMP-13 in U.S. Pat. No. 5,658,882; and BMP-15 in U.S. Pat. No. 5,635,372; each of the foregoing patents being incorporated herein by reference.

OP-1 sequences are disclosed in U.S. Pat. Nos. 5,011,691, 5,258,494 and 5,670,336; OP-3 in U.S. Pat. Nos. 5,652,118 and 5,652,337; COP-5 in U.S. Pat. Nos. 5,011,691, 5,182,365 and 5,258,494; and COP-7 in U.S. Pat. Nos. 5,011,691 and 5,182,365. BOP sequences are disclosed in U.S. Pat. No. 5,250,302. Other U.S. patents related to this include: U.S. Pat. Nos. 5,266,683, 5,324,819, 5,344,654, 5,354,557, 5,656,593 and 5,674,844, each of which are incorporated herein by reference, and are intended to be used in order to supplement the present teachings regarding the preparation of BMP and OP genes and DNA segments that express osteogenic polypeptides.

The definition of a "BMP gene", as used herein, is a gene that hybridizes, under relatively stringent hybridization conditions (see, e.g., Sambrook et al. (1989) Molecular Cloning: A Laboratory Manual, Cold Spring Harbor Laboratory, incorporated herein by reference), to DNA sequences presently known to include BMP gene sequences. By way of example only, U.S. Pat. No. 5,166,058, teaches that hBMP-2 is encoded by a nucleotide sequence from nucleotide #356 to nucleotide #1543 of the sequence shown in Table II of the patent. One may thus obtain a BMP-2 DNA segment using molecular biological techniques, such as polymerase chain reaction ("PCR") or screening a cDNA or genomic library, using primers or probes with sequences based on the above nucleotide sequence. The practice of such techniques is a routine matter for those of skill in the art (Sambrook et al., 1989; incorporated herein by reference). Certain documents further particularly describe suitable mammalian expression vectors, e.g., U.S. Pat. No. 5,168,050, incorporated herein by reference.

The PTH gene, or a DNA segment encoding the active fragment thereof, such as a DNA segment encoding a polypeptide that includes the amino acids 1-34 (hPTH1-34; Hendy et al., 1981; incorporated herein by reference; U.S. Pat. No. 5,700,774, incorporated herein by reference) is another preferred gene.

As disclosed in the above patents, and known to those of skill in the art, the original source of a recombinant gene or DNA segment to be used in a therapeutic regimen need not be of the same species as the animal to be treated. In this regard, it is contemplated that any recombinant PTH, TGF or BMP gene may be employed to promote bone repair or regeneration in a human subject or an animal, such as, e.g., a horse. Particularly preferred genes are those from human, mouse and bovine sources, in that such genes and DNA segments are readily available, with the human or mouse forms of the gene being most preferred for use in human treatment regimens. Recombinant proteins and polypeptides encoded by isolated DNA segments and genes are often referred to with the prefix "r" for recombinant and "rh" for recombinant human. As such, DNA segments encoding rBMPs, such as rhBMP-2 or rhBMP-4, are contemplated to be particularly useful in connection with this invention.

It is also contemplated that one may clone further genes or cDNAs that encode an osteogenic protein or polypeptide. The techniques for cloning DNA molecules, i.e., obtaining a specific coding sequence from a DNA library that is distinct from other portions of DNA, are well known in the art. The screening procedure may be based on the hybridization of oligonucleotide probes, designed from a consideration of portions of the amino acid sequence of known DNA sequences encoding related osteogenic proteins. The operation of such screening protocols are well known to those of skill in the art and are described in detail in the scientific literature, for example, in Sambrook et al. (1989), incorporated herein by reference.

By way of example only, genes to be supplied by the invention include, but are not limited to, those encoding and expressing: hormones, neurotransmitters, growth factors, growth factor receptors, interferons, interleukins, chemokines, cytokines, colony stimulating factors and chemotactic factors; transcription and elongation factors, cell cycle control proteins, including kinases and phosphatases, DNA repair proteins, apoptosis-inducing genes; oncogenes, antisense oncogenes and tumor suppressor genes; angiogenic and anti-angiogenic proteins; immune response stimulating and modulating proteins; cell surface receptors, accessory signaling molecules and transport proteins; enzymes; and antibacterial and anti-viral proteins.

3. Biological Functional Equivalents

As mentioned above, modification and changes may be made in the structure of a selected gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by change the codons of the DNA sequence, according to the following codon table:

| Amino Acids | | | Codon Table | | | | |
|---|---|---|---|---|---|---|---|
| | | | Codons | | | | |
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |

-continued

Codon Table

| Amino Acids | | | Codons | | | | | |
|---|---|---|---|---|---|---|---|---|
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the DNA sequences of osteogenic genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those that are within ±1 are particularly preferred, and those within ±0.5 are even more particularly preferred.

As outline above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

C. Therapeutic Approaches

1. Matrix-DNA Therapeutic Formulations and Kits

Once the appropriate matrix fabrication parameters and the desired gene(s) have been selected, the genes are associated with, or impregnated within, the biocompatible matrix to form a "matrix-gene composition". The matrix-gene composition can then be placed in contact with the target cells or tissue in vivo. The matrix can be impregnated with a gene or DNA segment simply by soaking the matrix in a solution containing the DNA, such as a plasmid solution, for a brief period of time of anywhere from about 5 minutes or so, up to and including about an hour. "Matrix-gene compositions" are thus all those in which a gene is adsorbed, absorbed, ionically bound, or otherwise maintained in contact with the matrix.

In preferred embodiments, the DNA is provided to the controlled or open pore matrices during the fabrication process. Both one-step and two-step DNA-incorporation gas foaming/particulate leaching processes are provided by the present invention. By incorporating the genetic material during the fabrication process, its provision or release can be controlled by controlling the release of polymer degradation (choice of polymer materials) and by controlling the diffusion of DNA through the pores (choice of fabrication parameters, controlling pore size). Otherwise, release would be governed only by desorption of DNA from the polymer surface. In essence, controlled and sustained provision or release can only be effectively achieved by incorporating the DNA during the matrix fabrication process.

In the preferred aspects of the one-step DNA-GF/PL processes, polymer particles and DNA are mixed with sodium chloride, compressed into a disc, and placed in a pressure vessel with a high pressure gas. As with the basic method, release of the pressure causes the polymer particles to expand, collide and fuse, thereby producing an interconnected structural matrix. Pores are again formed by leaching out the salt and leaving a matrix with an open pore structure.

The two-step DNA-GF/PL fabrication process also preferably involves mixing the polymer with DNA, compressing into a disc, and placing in a pressure vessel with high pressure gas. Release of the pressure produces an interconnected matrix; however, the polymer has a closed pore structure. In those less preferred aspects of the invention, where cellular invasion is not desired during use of the plasmid-containing matrix, the closed pore polymer can be used for sustained DNA delivery. The second step of this two-step process involves grinding the initial matrix into small pieces, mixing them with salt, pressing into a disc, and placement in a pressure vessel. The matrix is then foamed and the salt removed via leaching.

In certain other preferred embodiments, the three-dimensional structural matrices are composed of alginate that has been fabricated in a manner effective to control the pore size and structure by the processing technique. These structural matrices create a space and provide suitable stability to allow interacting cells to form new three dimensional tissues. The preferred fabrication processes also involve a gas foaming technique, as described above.

Data is presented herein to show that plasmids released from gas foamed and alginate matrices remain intact and functional. These plasmids are able to transfect cells in vitro and in vivo. In vivo, the transfected cells produce the encoded proteins in sufficient quantities to yield physiologically observable effects on tissue formation, e.g., increases in vascularization and granulation tissue in response to PDGF. Importantly, this physiological response is only observed with a matrix-mediated delivery of plasmid, and not by direct injection of equivalent plasmid quantities.

The provision or delivery of genetic material, particularly plasmid DNA, from the present three-dimensional, structural matrices is thus contemplated for use in virtually any application in which one would desire to provide genetic material to cells. As the three-dimensional structural matrices are designed to support cellular invasion, the matrix-DNA preparations are especially useful in the treatment of a wide variety of disorders and injuries in vivo. In fact, gene transfer using this invention is not limited to any particular tissue, but is widely applicable.

The approach of the present invention for inducing tissue formation is advantageous compared to other approaches that involve direct protein or plasmid DNA delivery. A traditional approach to achieve tissue formation with inductive molecules is the direct delivery of a growth factor (Deuel, 1997). Although this approach can induce a physiological response, it is difficult to achieve long-term delivery of functional proteins, due to the limitations of protein stability at 37° C. and immunogenicity (Langer, 1998).

The high stability of plasmid DNA may provide a significant advantage over direct delivery of the protein. However, direct injection of plasmid DNA into tissues typically leads to small numbers ($10^2$'-10) of transfected cells (Ledley, 1996). The present controlled delivery of plasmid DNA from PLGA matrices, in contrast, results in large numbers ($\sim 10^5$-$10^6$) of transfected cells that can produce the inductive factor (Example XVII). Clinical applications of proteins such as human PDGF would not result in adverse effects, such as inflammatory responses, as the produced proteins would be native to the human body.

The present invention demonstrates a controlled and sustained provision or release of plasmid DNA from a biodegradable tissue engineering matrix. Plasmid has been delivered in a sustained manner from a non-degradable polymer (Jong et al., 1997), and a polymer thin film coating (Labhasetwar et al., 1998). PLGA microspheres have also been used to deliver plasmid DNA encoding antigens to elicit a specific immune response (Hedley et al., 1998). One of the significant advantages of the present invention is the control of the DNA provision or delivery rate afforded by controlling the degradation rate of the biodegradable polymer used.

In the fabrication methods of the invention, DNA is incorporated within pores of the matrix during the foaming process when the polymer expands and entraps the DNA within the pores. The variation in DNA release kinetics obtained with this system (FIG. 1) is likely due to a differential foaming of the polymers due to their compositional and molecular weight differences. These results mean that one can readily control the time of plasmid DNA provision or release from the matrix in vivo, and thus the time frame for expression of the plasmid.

The potential for gene therapy approaches in tissue engineering has been previously demonstrated by transplantation of ex vivo transfected cells on porous polymer matrices. This led to local expression of a therapeutic protein that enhanced the survival of transplanted cells, and the formation of new vascular tissues (Nor et al., 1999). However, this approach carries with it all of the disadvantages of cell transplantation. With the present invention's delivery of plasmid DNA, cell transplantation is not a necessity (although it is certainly an embodiment included within the invention).

In the practice of the present invention, as the target cells penetrate or grow into the matrix, they contact the DNA therein, allowing the cells to take up the desired gene or cDNA and express the encoded protein. The matrices thus both deliver the gene composition and also provide a surface for new tissue growth, i.e., will act as an in situ scaffolding through which cells may migrate.

In the process of tissue engineering, tissue formation is characterized by temporal expression of a sequence of genes involved in development (Stein et al., 1996). The matrix system of the present invention, in contrast to previously described systems (Nor et al., 1999; Fang et al., 1996), is ideal for temporally defined provision or delivery and expression of a number of plasmids encoding for various genes in an engineered tissue.

A particular advantage of the present invention is that a combination of polymers can be used to prepare matrix-DNA formulations to provide or deliver multiple plasmids at different rates. This can be achieved using a single matrix-DNA preparation fabricated from multiple different polymers that are associated with different genes, such that each polymer releases a different gene at a different time. Equally, a number of individual DNA-matrices can be prepared, each one fabricated from a different polymer and each containing a different gene. Either way, the invention allows for the simple and controllable provision or delivery of multiple genes to a defined site in the body at an appropriate time frame.

Each of the gene transfer methods of the present invention thus generally comprise contacting target cells or tissues with a composition comprising a nucleic acid segment in combination with the defined structural matrix in a manner effective to transfer the nucleic acid segment into the cells. The cells may be cultured cells or recombinant cells maintained in vitro, when all that is required is to add the nucleic acid composition to the cells, e.g., by adding it to the culture media.

More preferably, the target cells are located within a tissue site of an animal, when the nucleic acid-matrix composition is applied to the site in order to effect, or promote, nucleic acid transfer into the target cells in vivo. In transferring nucleic acids into target cells within an animal, a preferred method involves first fabricating a biocompatible matrix with additional genetic material and then using the impregnated matrix to contact an appropriate tissue site within the animal.

The amount of gene construct that is applied to the matrix and the amount of matrix-gene material that is applied to the tissue will be determined by the attending physician or veterinarian considering various biological and medical factors. For example, one would consider the particular gene and matrix; the amount of tissue desired to be formed; the site of tissue damage; the condition of the damaged tissue; the patient's or animal's age, sex, and diet; the severity of any infection; the time of administration; and further clinical factors, such as serum levels of various factors and hormones. The suitable dosage regimen will therefore be readily determinable by one of skill in the art in light of the present disclosure, bearing in mind the individual circumstances.

An extremely wide variety of genetic material can be transferred to target cells or tissues using the compositions and methods of the invention. For example, the nucleic acid segment may be DNA (double or single-stranded) or RNA (e.g., mRNA, tRNA, rRNA). The nucleic acids may also include at least one "coding segment", i.e., that encodes a protein or polypeptide. Antisense nucleic acid molecules, such as antisense RNA, that function to disrupt gene expression are also contemplated. The nucleic acid segments may thus be genomic sequences, including exons or introns alone or exons and introns, or coding cDNA regions, or in fact any construct that one desires to transfer to a target cell or tissue. In terms of DNA vaccination, e.g., via nucleic acid transfer into antigen presenting cells (APCs), the nucleic acids transferred may even be total or partial genomic or cellular-extracted nucleic acids from pathogenic organisms, thereby generating an immune response against any one or more of the components of the pathogen.

Suitable nucleic acid segments may also be in virtually any form, such as naked DNA or RNA, including linear nucleic acid molecules and plasmids; functional inserts within the genomes of various recombinant viruses, including viruses with DNA genomes and retroviruses; and any form of nucleic acid segment, plasmid or virus associated with a liposome or a gold particle, the latter of which may be employed in connection with the gene gun technology.

The invention is preferably employed to promote expression of a desired gene in target cells or tissues and to impart a particular desired phenotype to the cells. This "expression" is useful in the increased expression of a gene that is normally expressed (i.e., "over-expression"); in the expression of a gene that is not normally associated with the target cells in their natural environment; and in the expression of a gene in a diseased or otherwise defective target cell that should normally express the gene, but is lacking due to a defect that needs correcting; and/or in the expression and processing of antigenic or immunogenic fragments, allowing cell surface presentation, particularly by APCs.

Alternatively, the invention may be used to suppress the expression of a gene that is naturally expressed in target cells and tissues, and again, to change or alter the phenotype. Gene suppression may be a way of expressing a gene that encodes a protein that exerts a down-regulatory function, or it may utilize antisense technology.

Irrespective of the chosen therapeutic embodiment, particularly influenced by the gene(s) used, the DNA-matrices of the present invention may be formulated as therapeutic devices, generally molded or designed matrix-gene compositions. The devices may be of virtually any size or shape, so that their dimensions are adapted to fit the biological area of the animal that is to be treated.

Therapeutic kits comprising, in suitable container means, a defined biocompatible matrix and one or more selected genes form another aspect of the invention. Such kits will generally contain a pharmaceutically acceptable formulation of the matrix and a pharmaceutically acceptable formulation of a selected gene.

The kits may comprise a single container means that contains both the biocompatible matrix and the gene(s). In this sense, the container means may contain a pharmaceutically acceptable sterile matrix having associated with it, the gene composition. The matrix may even be a gelatinous matrix-DNA formulation, e.g., in the form of a syringeable composition. In which cases, the container means may itself be a syringe, pipette, or other such like apparatus, from which the matrix-DNA material may be applied to a tissue site or wound area. Gene-matrices that are "ready to use", such as sponges, implants, tubes, band-aids, bandages, gels, patches, pads, nanoparticles, lyophilized components, powders and telfa pads are thus provided. However, single containers containing a dry, or lyophilized, mixture of a matrix and gene composition, which may or may not require pre-wetting before use, are also provided.

Alternatively, the kits of the invention may comprise distinct container means for each component. In such cases, one container would contain the gene, either as a sterile DNA solution or in a lyophilized form, and the other container would include the matrix, which may or may not itself be prewetted with a sterile solution.

The kits may also comprise a second or third container means for containing a sterile, pharmaceutically acceptable buffer or other diluent. Such a solution may be required to formulate either the DNA component, the matrix component, both components separately, or a pre-mixed combination of the components, into a more suitable form for application to the body. It should be noted, however, that all components of a kit could be supplied in a dry form, which would allow for "wetting" upon contact with body fluids. Thus, the presence of any type of pharmaceutically acceptable buffer is not a requirement for the kits of the invention.

The container means will generally be a container such as a vial, test tube, flask, bottle, syringe or other container means, into which the components of the kit may placed. The matrix and gene components may also be aliquoted into smaller containers, should this be desired. The kits of the present invention may also include a means for containing the individual containers in close confinement for commercial sale, such as, e.g., injection or blow-molded plastic containers into which the desired vials or syringes are retained.

Irrespective of the number of containers, the kits of the invention may also comprise, or be packaged with, an instrument for assisting with the placement of the ultimate matrix-gene composition within the body of an animal. Such an instrument may be a syringe, pipette, forceps, or any such medically approved delivery vehicle.

In other embodiments of the invention, the DNA matrices may be used to coat surgical devices, such as suture materials or implants. In some instances, medical devices such as implants, sutures, wound dressings, etc., may be coated with the nucleic acid compositions of the invention using conventional coating techniques that are well known in the art. Such methods include, by way of example and not limitation, dipping the device in the nucleic acid composition, brushing the device with the nucleic acid composition and/or spraying the device with the aerosol nucleic acid compositions of the invention. The device is then dried, either at room temperature or with the aid of a drying oven, optionally at reduced pressure. A preferred method for coating sutures is provided in Example IX.

For sutures coated with a polymeric matrix containing plasmid DNA, it is suitable to applying a coating composition containing a total of about 0.01 to 10 mg plasmid DNA, and preferably about 1 to 5 mg plasmid DNA, to a 70 cm length of suture using about 5 to 100, preferably about 5 to 50, and more preferably about 15 to 30 coating applications, in order to yield a therapeutically effective and uniform coating.

Sutures that may be coated include any suture of natural or synthetic origin, typically including, by way of example and not limitation: silk; cotton; linen; polyolefins such as polyethylene and polypropylene; polyesters such as polyethylene terephthalate; homopolymers and copolymers of hydroxycarboxylic acid esters; collagen (plain or chromicized); catgut (plain or chromicized); and suture-substitutes, such as cyanoacrylates. The sutures may take any convenient form such as braids or twists, and may have a wide range of sizes as are commonly employed in the art.

The sutures coated with polymeric matrices containing nucleic acids encoding therapeutic proteins can be used to stimulate wound healing in vivo. The advantages of using such coated sutures cover virtually every field of surgical use in humans and animals.

2. Wound Healing

Wound healing is usually a co-ordinated, stereotyped sequence of events that includes: tissue disruption and loss of normal tissue architecture; cell necrosis and hemorrhage; hemostasis (clot formation); infiltration of segmented and mononuclear inflammatory cells, with vascular congestion and tissue edema; dissolution of the clot as well as damaged cells and tissues by mononuclear cells (macrophages); formation of granulation tissue (fibroplasia and angiogenesis). This sequence of cellular events has been observed in wounds from all tissues and organs generated in a large number of mammalian species (Gailet et al., 1994). Therefore, the cellular sequence described above is a universal aspect of the repair of all mammalian tissues.

Currently available wound healing therapies involve the administration of therapeutic proteins. Such therapeutic proteins may include regulatory factors involved in the normal healing process such as systemic hormones, cytokines, growth factors and other proteins that regulate proliferation and differentiation of cells. Growth factors, cytokines and hormones having wound healing capacity include, for example, the TGF-β superfamily of proteins, acidic fibroblast growth factor (aFGF), macrophage-colony stimulating factor (M-CSF) and calcium regulatory agents, such as parathyroid hormone (PTH).

As with other therapies described herein, a number of problems are associated with the use of proteins in wound healing therapies. First, the purification and/or recombinant production of therapeutic proteins is an expensive and time-consuming process. Despite best efforts, purified protein preparations are often unstable, making storage and use cumbersome. Protein instability can also lead to unexpected inflammatory reactions (to protein breakdown products) that are toxic to the host.

Second, systemic delivery of therapeutic proteins is often associated with serious unwanted side effects in unwounded tissue. Due to inefficient delivery to specific cells and tissues in the body, administration of high doses of protein are required to ensure that sufficient amounts of the protein reach the appropriate tissue target. The circulation of high doses of therapeutic proteins is often toxic due to pleiotropic effects of the administered protein, and may give rise to serious side effects. In light of the short half life in the body, due to proteolytic degradation, the proteins must also be administered repeatedly, which may give rise to an immune reaction to the therapeutic proteins.

Third, exogenous delivery of recombinant proteins is inefficient. Attempts have been made to limit the administration of high levels of protein through immobilization of therapeutic protein at the target site. However, this therapeutic approach complicates the readministration of the protein for repeated dosing.

Fourth, for a variety of proteins, such as membrane receptors, transcription factors and intracellular binding proteins, biological activity is dependent on correct expression and localization in the cell. For many proteins, correct cellular localization occurs as the protein is post-translationally modified inside the cells. Therefore, such proteins cannot be administered exogenously in such a way as to be taken up and properly localized inside the cell.

In contrast to the many deficiencies of protein therapies for wound healing, the present invention provides rational methods for the in vivo production of physiological amounts of desired proteins at their site of action. The present matrix-gene invention also overcomes the problems associated with currently devised gene therapies, namely the inability to transfer DNA efficiently into a targeted cell population and to achieve high level expression of the gene product in vivo. The matrix-gene compositions and devices of this invention may thus be used in wound healing and related tissue repair, including, but not limited to healing of burns, incisions, ulcers and various other forms of tissue damage.

The invention thus provides methods for specific targeting and transfer of nucleic acids into mammalian repair cells involved in wound healing, e.g., in order to express therapeutic products at the wound site. These methods of the invention generally involve administering a gene-matrix into a fresh wound site in the body. In this setting, repair cells are localized to the wound site, where they become transfected and produce DNA-encoded agents (RNAs, proteins, etc.) that enhance wound healing.

The invention is based, in part, on the discovery that repair cells, active in the wound healing process, proliferate and migrate from surrounding tissue into the area of the wound and infiltrate the gene activated matrix. The matrix acts as a scaffolding that promotes cell ingrowth, and, in turn, gene transfer, through the local accumulation of repair cells near the DNA. While in the matrix, repair cells are efficient at taking up the DNA and expressing it as translational products, i.e. proteins, or transcriptional products, i.e. antisense and ribozymes. This is surprising, as such repair cells are normally difficult to efficiently transfect, either in vitro or in vivo. The repair cells are thus evidently activated to proliferate by the wound healing process and the matrix environment. The transfected repair cells then serve as local bioreactors amplifying the production of the gene product in vivo.

While any number of DNA sequences can be used in the method, preferred DNA sequences are those that encode translational products (i.e. proteins) or transcriptional products (i.e. antisense or ribozymes) that (a) promote tissue repair; or (b) are capable of disrupting a disease process (thereby allowing normal tissue healing to take place).

The invention overcomes the shortcomings of procedures currently used for wound healing involving the administration of therapeutic proteins. First, DNA, which is both stable and non-toxic, can be safely administered in high doses in vivo. Second, repeated administration, while possible, is not required. The cells that take up and express the DNA provide a supply of gene product at the site of the wound. Third, the invention can be practiced in a way that addresses the temporal requirements of dosing. For example, the DNA can be presented in vectors that integrate into the genome of the targeted cell. In this case, all daughter cells will contain and express the transferred DNA, thereby acting as a continuous source for the therapeutic agent. In contrast, non-integrating systems may be utilized wherein the DNA does not integrate into the genome and the gene is not passed on to daughter cells. In such an instance, when the wound healing process is completed and the gene product is no longer needed, the gene product will not be expressed.

The invention, as shown in the examples herein, can be used to reproducibly transfer and express genes in a variety of wounded soft and hard tissues in vivo. The matrix-based invention thus provides genes to a suitable number of repair cells to achieve functional effects in vivo, i.e. in the absence of any further targeting or cellular identification by the practitioner. By analogy, the DNA acts much like "bait" in a "trap": the DNA is encountered by unwitting repair cells that have proliferated and then migrated into the gene activated matrix. These cells, in turn, are surprisingly capable of taking up DNA and expressing it as a therapeutic agent.

In one embodiment of the invention, the method of the invention may be used as a drug delivery system through transfer of DNA into mammalian repair cells for the purpose of stimulating soft and hard tissue repair and tissue regeneration. The repair cells will be those cells that normally arrive at the area of the wound to be treated. Accordingly, there is no difficulty associated with the obtaining of suitable target cells to which the present therapeutic compositions should be applied. All that is required is the implantation of a gene-activated matrix at the wound site. The nature of this biological environment is such that the appropriate repair cells will actively take up and express the "bait" DNA in the absence of any further targeting or cellular identification by the practitioner.

The methods of the invention can be used to transfer DNA into mammalian repair cells, e.g., to stimulate skeletal tissue regeneration (see Section C3, below); ligament and tendon repair; and to stimulate soft tissue and/or blood vessel repair. A "repair cell" or "mammalian repair cell", as used herein, is any cell or mammalian cell that contributes to a beneficial response to injury. Preferably, the repair cells are stimulated to migrate and proliferate in response to tissue injury. Repair cells are thus a component of the wound healing response and include, for example, fibroblasts, capillary endothelial cells, capillary pericytes, mononuclear inflammatory cells, segmented inflammatory cells and granulation tissue cells.

As used herein, the term "wound site" is generally defined as any location in the host animal or patient that arises from tissue injury, such as tissue damage that occurs as a result of disease, traumatic tissue injury, or surgical procedures.

"Wound healing" is generally achieved by using the transfected repair cells to produce the encoded therapeutic agents, which then influence the local repair environment. For example, growth factors or cytokines produced by the transfected repair cells bind and stimulate targeted effector cells that express cognate cell surface receptors, thereby stimulating and amplifying the cascade of physiological events normally associated with the wound healing process.

Alternatively, the repair cells may take up and express DNA encoding proteins that inhibit the activity of antagonists of the wound healing process. The DNA may also encode antisense or ribozyme RNA molecules that may be used to inhibit translation of mRNAs encoding inflammatory proteins or other factors that inhibit wound healing or cause excessive fibrosis.

The gene-matrix of the invention can be transferred to an animal or patient using a variety of techniques. For example, when stimulating wound healing and regeneration, the matrices are transferred directly to the site of the wound, i.e. the fractured bone, injured connective tissue, etc. For use in skin repair, the matrices are topically administered. For use in organ regeneration, the matrices are surgically placed in a wound made in the organ.

Since the operative methods are based on the natural migration and proliferation of repair cells into a wound site, and infiltration into the gene-matrix located at the wound site, followed by the uptake of DNA, it is understood that the matrices should be transferred at or near a site in the body where the wound healing process is being induced. Matrices can thus be directly applied to the site of the wound by the hand of the physician, or placed surgically in a normal tissue site in order to treat nearby diseased tissue. In instances where the DNA-matrices are to be injected, the matrices are drawn up into a syringe and injected into an animal or patient at the site of the wound. Multiple injections may be made in the area of the wound.

An important feature of the invention is that the repair process may be engineered to result in either the formation of scar tissue and/or tissue regeneration. For example, overexpression of therapeutic proteins at the site of the wound may result in regeneration of the injured tissue without the formation of scar tissue. In many instances, for example, such as bone repair, such regeneration is desirable because scar tissue is not optimally designed to support normal mechanical function. This is also true in instances such as the treatment of burns and connective tissue damage.

Equally, around a suture it may be desirable to form scar tissue to hold inherently weak tissue together. Therefore, the methods of invention may be used to stimulate wound healing either with, or without, the formation of scar tissue, depending on the tissue type and the type and level of therapeutic protein expressed.

The wound-healing methods of the invention can be universally applied to wounds that involve many different cells, tissues and organs. These include, but are not limited to, bone repair; connective tissue repair, such as cartilage, tendon and ligament repair; blood vessel repair; skeletal muscle repair; skin repair; organ regeneration; and regulation of vasculogenesis and/or angiogenesis. The end result of therapeutic protein expression is the augmentation of tissue repair and regeneration. The invention is also useful in blocking disease processes, thereby allowing natural tissue healing to take place.

The gene-matrices may also be used to treat patients with impaired healing capacity resulting from, for example, the effects of aging or diabetes. The matrices may also be used for treatment of wounds that heal slowly due to natural reasons, e.g., in the elderly, and those who do not respond to existing therapies, such as in those individuals with chronic skin wounds.

Soft Tissue Repair

Skeletal connective tissue damage due to traumatic injury can be treated using matrices containing genes encoding a variety of growth factors. Connective tissue normally consists of cells and extracellular matrix organized in a characteristic tissue architecture. Tissue wounding disrupts this architecture and stimulates a wound healing response. The methods of the present invention are particularly well suited for stimulation of growth and regeneration of connective tissue, as it is important that the injured tissue regenerate without the formation of scar tissue—as scar tissue can interfere the normal mechanical function of connective tissue.

Various growth factors may be used to promote soft tissue repair. These include, but are not limited to, members of the TGF-$\alpha$ superfamily (e.g., TGF-$\beta$ itself), that stimulate expression of genes coding for extracellular matrix proteins, and other cytokines such as EGF and PDGF. Examples of other genes that may be used include: (a) cytokines, such as the peptide growth and differentiation factors, interleukins, chemokines, interferons, colony stimulating factors; (b) angiogenic factors, such as FGF and VEGF; (c) extracellular matrix proteins, such as collagen, laminin, and fibronectin; (d) the family of cell adhesion molecules, e.g., the integrins, selectins, Ig family members such as N-CAM and L1, and cadherins; (e) cell surface cytokine signaling receptors, such as the type I and type II TGF-$\beta$ receptors and the FGF receptors; (f) non-signaling co-receptors, such as betaglycan and syndecan; (g) the family of signal transducing kinases; (h) cytoskeletal proteins, such as talin and vinculin; (i) cytokine binding proteins, such as the family of latent TGF-β binding proteins; and (j) nuclear trans acting proteins, such as transcription factors.

Once formed, such matrices are then placed in the host mammal in the area of the connective tissue wound. Gene activated matrices can be injected directly into the area of connective tissue injury. Alternatively, surgical techniques, such as arthroscopic surgery, may be used to deliver the matrices to the area of the connective tissue wound.

Organ Regeneration

The invention may also be used to stimulate the repair and regeneration of organ tissue, e.g., following traumatic injury or surgery. In the case of liver, the liver may be damaged due to excessive alcohol consumption or due to infection with various types of infectious agents, such as the hepatitis family of viruses. The kidney may likewise fail to function normally as a result of damage resulting from kidney disease. Mucous membranes of the esophagus, stomach or duodenum may contain ulcerations caused by acid and pepsin in gastric juices. The ulcerations may also arise from colonization of gastric mucosal cells with *Helicobacter pylori* bacteria. These organs and diseases serve only as examples, indeed the methods of the invention may be used to treat diseases, or to stimulate organ regeneration in any organ of the body.

Matrices containing DNA encoding cytokines that stimulate proliferation and differentiation of cells, and/or regulate tissue morphogenesis, are transplanted to the appropriate organ site. Such factors include, but are not limited to: the transforming growth factor family of proteins; platelet derived growth factor (PDGF); insulin like growth factor (IGF); and fibroblast growth factory (FGF). In some instances, it may be useful to express growth factors and/or cytokines that stimulate the proliferation of cell types specific for a given organ, e.g., hepatocytes, kidney or cardiac cells, etc. For example, hepatocyte growth factor may be expressed to stimulate the wound healing process in the liver. For treatment of ulcers, resulting from *Helicobacter* infection, the gene activated matrices may contain DNA encoding antimicrobial proteins.

The gene activated matrices of the invention may be surgically implanted into the organ that is to be treated. Alternatively, laproscopic surgical procedures may be utilized to transfer the gene activated matrices into the body. In cases where the treatment is in response to tissue injury, the natural wound healing process will stimulate the migration and proliferation of the repair cells to the transplanted matrices. Alternatively, where the gene activated matrices are transferred to organs that have not been injured, for example, where matrices are implanted to express therapeutic proteins not involved in wound healing, the wound healing process can be stimulated by induction of tissue injury.

Regulation of Angiogenesis

Another use of the invention is to regulate the formation and spreading of blood vessels, or vasculogenesis and angiogenesis, respectively. Both these physiological processes play an important role in wound healing and organ regeneration.

Initially, at the site of a wound, granulation tissue, which is a mixture of collagen, matrix and blood vessels, is deposited and provides wound strength during tissue repair. The formation of new blood vessels involves the proliferation, migration and infiltration of vascular endothelial cells, and is known to be regulated by a variety of polypeptide growth factors. Several polypeptides with endothelial cell growth promoting activity have been identified, including acidic and basic fibroblastic growth factors (FGF), vascular endothelial growth factor (VEGF), and placental derived growth factor (PDGF).

To stimulate the formation and spreading of blood vessels, DNA encoding such growth factors is incorporated into matrices and these matrices are implanted into the host. In some instances, it may be necessary to induce the wound healing process through tissue injury.

It is often desirable to inhibit the proliferation of blood vessel formation, such as in angiogenesis associated with the growth of solid tumors, which rely on vascularization for growth. Tumor angiogenesis is inhibited through the transfer of DNAs encoding negative inhibitors of angiogenesis, such as thrombospondin or angiostatin. In specific embodiments of the invention, DNA encoding, for example, thrombospondin or angiostatin, is thus incorporated into a matrix and the matrix implanted into an animal or patient at or near the site of a tumor.

Repair of the Skin

The present invention may also be used to stimulate the growth and repair of skin tissue. In wounds that involve injury to areas of the skin, and particularly in the case of massive burns, it is important that the skin grow very rapidly in order to prevent infections, reduce fluid loss, and reduce the area of potential scarring. Skin damage resulting from burns, punctures, cuts and/or abrasions is treatable using the gene activated matrices of the present invention. Skin disorders such as psoriasis, atopic dermatitis or skin damage arising from fungal, bacterial and viral infections or treatment of skin cancers such as melanoma, can also be treated using the methods of the invention.

Matrices containing DNA encoding cytokines that stimulate proliferation and differentiation of cells of the skin, including central basal stem cells, keratinocytes, melanocytes, Langerhans cells and Merkel cells can be used to treat skin injuries and disorders. The gene activated matrices serve two functions: the protection of the wound from infection and dehydration; and supplying the DNA for uptake by repair cells. The gene activated matrices of the invention can be combined with, or fabricated into, dermal patches, cadaver skin, band-aids, gauze pads, collagen lattices, topical creams or gels. Prior to the application of the matrices to the wound site, damaged skin or devitalized tissue may be removed.

The DNA to be incorporated into the matrices can encode a variety of different growth factors, including keratinocyte-growth-factor (KGF) or epidermal growth factor (EGF). DNA encoding IL-1, which has been shown to be a potent inducer of epithelial cell migration and proliferation as part of the healing process, may also be incorporated into these matrices of the invention.

3. Bone Repair

Bone has a substantial capacity to regenerate following fracture. Defects in the process of bone repair and regeneration are linked to the development of several human diseases and disorders, e.g., osteoporosis and osteogenesis imperfecta. Failure of the bone repair mechanism is, of course, also associated with significant complications in clinical orthopaedic practice, for example, fibrous non-union following bone fracture, implant interface failures and large allograft failures. The lives of many individuals can now be improved by application of the present invention to stimulate and strengthen the fracture repair process. Indeed, DNA release from matrices in general has already been shown to be operative for gene transfer into bone progenitor cells and wound-healing fibroblasts in vivo (see, e.g., U.S. application Ser. No. 08/199,780, filed Feb. 18, 1994, now U.S. Pat. No. 5,763,416, and U.S.

application Ser. No. 08/631,334, filed Apr. 12, 1996, now U.S. Pat. No. 5,962,427, each incorporated herein by reference).

A very significant patient population to benefit from the new and improved therapies provided hereby are those patients suffering from osteoporosis. The term osteoporosis refers to a heterogeneous group of disorders characterized by decreased bone mass and fractures. Clinically, osteoporosis is segregated into type I and type II. Type I osteoporosis occurs predominantly in middle aged women and is associated with estrogen loss at the menopause, while osteoporosis type II is associated with advancing age.

An estimated 20-25 million people are at increased risk for fracture because of site-specific bone loss. The cost of treating osteoporosis in the United States is currently estimated to be in the order of $10 billion per year. Demographic trends, i.e., the gradually increasing age of the US population, suggest that these costs may increase 2-3 fold by the year 2020 if a safe and effective treatment is not found.

Osteogenesis imperfecta (OI) refers to a group of inherited connective tissue diseases characterized by bone and soft connective tissue fragility. The overall incidence is currently estimated to be 1 in 5,000-14,000 live births. Hearing loss, dentinogenesis imperfecta, respiratory insufficiency, severe scoliosis and emphysema are just some of the conditions that are associated with one or more types of OI. While accurate estimates of the health care costs are not available, the morbidity and mortality associated with OI certainly result from the extreme propensity to fracture (OI types I-IV) and the deformation of abnormal bone following fracture repair (OI types II-IV). The most relevant issue with OI treatment is to develop new methods by which to improve fracture repair and thus to improve the quality of life of these patients.

The techniques of bone reconstruction, such as is used to reconstruct defects occurring as a result of trauma, cancer surgery or errors in development, would also be improved by new methods to promote bone repair. Reconstructive methods currently employed, such as using autologous bone grafts, or bone grafts with attached soft tissue and blood vessels, are associated with significant drawbacks of both cost and difficulty. For example, harvesting a useful amount of autologous bone is not easily achieved, and even autologous grafts often become infected or suffer from resorption.

The process of bone repair and regeneration resembles the process of wound healing in other tissues. A typical sequence of events includes; hemorrhage; clot formation; dissolution of the clot with concurrent removal of damaged tissues; ingrowth of granulation tissue; formation of cartilage; capillary ingrowth and cartilage turnover; rapid bone formation (callus tissue); and, finally, remodeling of the callus into cortical and trabecular bone. Therefore, bone repair is a complex process that involves many cell types and regulatory molecules. The diverse cell populations involved in fracture repair include stem cells, macrophages, fibroblasts, vascular cells, osteoblasts, chondroblasts, and osteoclasts.

Regulatory factors involved in bone repair are known to include systemic hormones, cytokines, growth factors, and other molecules that regulate growth and differentiation. Various osteoinductive agents have been purified and shown to be polypeptide growth-factor-like molecules. These stimulatory factors include BMPs (also termed OPs), which are part of the TGF-β superfamily.

Examples of suitable osteogenic growth factors include TGF-β1, TGF-β2, TGF-β2, and even TGF-α; GMCSF; EGF; PDGF; IGF-I and IGF-II; LIF; and BMPs and OPs, as exemplified by those in U.S. Pat. Nos. 4,877,864; 4,968,590; 5,011, 691; 5,013,649; 5,106,748; 5,108,753; 5,108,922; 5,116,738; 5,141,905; 5,166,058; 5,182,365; 5,187,076; 5,250,30; 5,258,494; 5,266,683; 5,324,819; 5,344,654; 5,354,557; 5,366,875; 5,399,677; 5,459,047; 5,543,394; 5,618,924; 5,631,142; 5,635,372; 5,635,373; 5,637,480; 5,639,638; 5,652,118; 5,652,337; 5,656,593; 5,658,882; 5,661,007; 5,674,844; 5,688,678; 5,670,336; 5,700,774; 5,700,911; and 5,703,043; each incorporated herein by reference.

Other growth factors or hormones that have been reported to have the capacity to stimulate new bone formation include acidic fibroblast growth factor (Jingushi et al., 1990); estrogen (Boden et al., 1989); macrophage colony stimulating factor (Horowitz et al., 1989); and calcium regulatory agents such as PTH (Raisz & Kream, 1983).

The defined DNA-matrices of the present invention are particularly useful for transferring nucleic acids into wounded tissues, such as bone cells and tissues undergoing repair and regeneration. The use of the invention in transferring nucleic acids into bone progenitor cells or tissues is particularly advantageous.

Certain methods of the invention comprise contacting bone progenitor cells, preferably within a bone progenitor tissue site of an animal, with a matrix-nucleic acid composition in order to effect, or promote, nucleic acid transfer into bone progenitor cells in vivo. As used herein, the term "bone progenitor cells" refers to any or all of those cells that have the capacity to ultimately form, or contribute to the formation of, new bone tissue. This includes various cells in different stages of differentiation, such as, for example, stem cells, macrophages, fibroblasts, vascular cells, osteoblasts, chondroblasts, osteoclasts, and the like. Gene transfer into granulation tissue fibroblasts is particularly preferred as this is relevant to a variety of wound healing processes, not just to bone progenitor cells.

Bone progenitor cells also include cells that have been isolated and manipulated in vitro, e.g., subjected to stimulation with agents such as cytokines or growth factors or even genetically engineered cells. The particular type or types of bone progenitor cells that are stimulated using the methods and compositions of the invention are not important, so long as the cells are stimulated in such a way that they are activated and, in the context of in vivo embodiments, ultimately give rise to new bone tissue.

The term "bone progenitor cell" is also used to particularly refer to those cells that are located within, are in contact with, or migrate towards (i.e., "home to"), bone progenitor tissue and which cells directly or indirectly stimulate the formation of mature bone. As such, the progenitor cells may be cells that ultimately differentiate into mature bone cells themselves, i.e., cells that "directly" form new bone tissue. Cells that, upon stimulation, attract further progenitor cells or promote nearby cells to differentiate into bone-forming cells (e.g., into osteoblasts, osteocytes and/or osteoclasts) are also considered to be progenitor cells in the context of this disclosure— as their stimulation "indirectly" leads to bone repair or regeneration. Cells affecting bone formation indirectly may do so by the elaboration of various growth factors or cytokines, or by their physical interaction with other cell types. Although of scientific interest, the direct or indirect mechanisms by which progenitor cells stimulate bone or wound repair is not a consideration in practicing this invention.

Bone progenitor cells and bone progenitor tissues may be cells and tissues that, in their natural environment, arrive at an area of active bone growth, repair or regeneration (also referred to as a wound repair site). In terms of bone progenitor cells, these may also be cells that are attracted or recruited to such an area. These may be cells that are present within an artificially-created osteotomy site in an animal model, such as those disclosed herein.

Bone progenitor cells may also be isolated from animal or human tissues and maintained in an in vitro environment. Suitable areas of the body from which to obtain bone progenitor cells are areas such as the bone tissue and fluid surrounding a fracture or other skeletal defect (whether or not this is an artificially created site), or indeed, from the bone marrow. Isolated cells may be stimulated using the methods and compositions disclosed herein and, if desired, be returned to an appropriate site in an animal where bone repair is to be stimulated. In such cases, the nucleic acid containing cells would themselves be a form of therapeutic agent. Such ex vivo protocols are well known to those of skill in the art.

In important embodiments of the invention, the bone progenitor cells and tissues will be those cells and tissues that arrive at the area of bone fracture or damage that one desires to treat. Accordingly, in treatment embodiments, there is no difficulty associated with the identification of suitable target progenitor cells to which the present therapeutic compositions should be applied. All that is required in such cases is to obtain an appropriate stimulatory composition, as disclosed herein, and contact the site of the bone fracture or defect with the composition. The nature of this biological environment is such that the appropriate cells will become activated in the absence of any further targeting or cellular identification by the practitioner.

Certain methods of the invention involve, generally, contacting bone progenitor cells with a matrix composition comprising one or more osteogenic genes (with or without additional genes, proteins or other biomolecules) so as to promote expression of the gene in the cells. As outlined above, the cells may be contacted in vitro or in vivo. The inventors surprisingly found that there are no particular molecular biological modifications that need to be performed on the DNA in order to promote effective expression of the gene in progenitor cells. Contacting the cells with matrix-associated DNA, e.g., a linear DNA molecule, or DNA in the form of a plasmid or other recombinant vector, that contains the gene of interest under the control of a promoter, along with the appropriate termination signals, is sufficient to result in uptake and expression of the DNA, with no further steps necessary.

In preferred embodiments, the process of contacting the progenitor cells with the osteogenic gene-matrix composition is conducted in vivo. Again, a direct consequence of this process is that the cells take up and express the gene and that they, without additional steps, function to stimulate bone tissue growth, repair or regeneration.

An assay of an osteoinductive gene may be conducted using the bone induction bioassay of Sampath & Reddi (1981; incorporated herein by reference). This is a rat bone formation assay that is routinely used to evaluate the osteogenic activity of bone inductive factors. However, for analyzing the effects of osteogenic genes on bone growth, one is generally directed to use the novel osteotomy model disclosed herein.

In treating humans and animals, progress may be monitored by periodic assessment of bone growth and/or repair, e.g., using x-rays. The therapeutic methods and compositions of the invention are contemplated for use in both medical and veterinary applications, due to the lack of species specificity in bone inductive factors. In particular, it is contemplated that domestic, farm and zoological animals, as well as thoroughbred horses, would be treatable using the nucleic acid transfer protocols disclosed herein.

The present methods and compositions may also have prophylactic uses in closed and open fracture reduction and also in the improved fixation of artificial joints. The invention is applicable to stimulating bone repair in congenital, trauma-induced, or oncologic resection-induced defects, and is even useful in cosmetic plastic surgery.

Important uses of the invention are in the stimulation of bone repair in craniofacial defects resulting from congenital conditions, trauma or oncologic resection, and in the treatment of periodontal disease and other tooth repair processes. Use of the present invention in connection with localized PDGF delivery may be preferred for tissue regeneration connected with periodontal disease (Giannobile, 1996).

A further aspect of the present invention is its use in connection with orthopaedic implants and interfaces and artificial joints, including implants themselves and functional parts of an implant, such as, e.g., surgical screws, pins, and the like. The metal surface or surfaces of an implant or a portion thereof, such as a titanium surface, can be coated with a material that has an affinity for nucleic acids, most preferably, with hydroxyl apatite, and then the coated-metal will be further coated with the gene or nucleic acid that one wishes to transfer. The available chemical groups of the absorptive material, such as hydroxyl apatite, may be readily manipulated to control its affinity for nucleic acids, as is known to those of skill in the art.

The following examples are included to demonstrate preferred embodiments of the invention. It will be appreciated by those of skill in the art that the techniques disclosed in the examples that follow represent techniques discovered by the inventors to function well in the practice of the invention, and thus can be considered to constitute preferred modes for its practice. However, those of skill in the art will, in light of the present disclosure, appreciate that many changes can be made in the specific embodiments that are disclosed and still obtain a like or similar result without departing from the spirit and scope of the invention.

Example I

Animal Model of Wound Repair in Terms of New Bone Formation

To study the effects of nucleic acid transfer on wound repair in terms of new bone formation, one of the inventors developed the following animal model osteotomy system. The rat osteotomy model protocol is generally completed in 25-35 minutes. The osteotomy is generally performed on one femur per animal. Right to left differences have not been apparent, but such differences are monitored in these studies, since the limb receiving the osteotomy is randomized.

After pre-operative preparation (i.e. shaving and betadine scrub), adult male Sprague Dawley rats (~500 gm, retired male breeders) are anesthetized using a 3% halothane 97% oxygen mixture (700 ml/min. flow rate). A lateral approach to the femur is made on one limb. Utilizing specially designed surgical guides, four 1.2 mm diameter pins are screwed into the diaphysis after pre-drilling with a high speed precision bit. A surgical template ensures precise and parallel placement of the pins.

The order of pin placement should generally be the same: outer proximal first and then outer distal, inner proximal and inner distal (with "outer" and "inner" referring to the distance from the hip joint). Pin placement in the center of the femur is ensured by fluoroscopic imaging during pin placement. The external fixator is secured on the pins and a 5 mm or 2 mm segmental defect is created in the central diaphysis through an incision using a Hall Micro 100 Oscillating saw (#5053-60 Hall surgical blades) under constant irrigation. Other than the size of the segmental defect, there is no difference between the 5 mm and 2 mm osteotomy protocols.

Various implant materials may be used for transferring genes into the site of wound healing, bone repair and/or regeneration in vivo. Certain preferred matrices are described herein in Example XI through Example XX. Such materials are soaked in, or fabricated with, a solution containing the DNA or gene that is to be transferred to the bone regrowth site.

Prior to placement in osteotomy sites, implant materials are soaked in solutions of DNA (or virus) under sterile conditions. The soaking is for any appropriate and convenient period, e.g., from 5-6 minutes to over-night. The DNA (e.g., plasmid) solution is a sterile aqueous solution, such as sterile water or an acceptable buffer, with the concentration generally being about 0.5-1.0 mg/ml. Exemplary plasmids are those such as pGL2 (Promega), pSV40b-gal, pAd.CMVlacZ, and pLJ.

The contents of the osteotomy site are irrigated with sterile saline and the implant material or matrix, previously soaked in a solution of plasmid DNA or other DNA construct, if appropriate, is placed in situ. The wound is then closed in layers. Since the fixator provides the necessary stability no limitations on animal ambulation exist, and other supports are not required. The surgical protocol has been successfully performed on numerous animals to date. None of these animals have died and no significant adverse effects have been observed, other than complications that might be associated with surgical fracture repair. Minor complications that were experienced include 1 animal that developed a post-operative osteomyelitis and 1 animal in which 2/4 pins loosened as a consequence of bone fracture.

The rate of new bone formation is analyzed as follows. At necropsy the osteotomy site is carefully dissected for histomorphometric analysis. The A-P and M-L dimensions of the callus tissue are measured using calipers. Specimens are then immersion fixed in Bouins fixative, washed in ethanol, and demineralized in buffered formic acid. Plastic embedding of decalcified materials is used because of the superior dimensional stability of methacrylate during sample preparation and sectioning.

Tissue blocks are dehydrated in increasing alcohol concentrations and embedded. 5 mm thick sections are cut in the coronal plane using a Reichert Polycut microtome. Sections are prepared from midway through the width of the marrow cavity to guard against a sampling bias. Sections for light microscopy are stained using a modified Goldner's trichrome stain, to differentiate bone, osteoid, cartilage, and fibrous tissue. Sections are cover-slipped using Eukitt's mounting medium (Calibrated Instruments, Ardsley, N.Y.). Histomorphometric analyses are performed under brightfield using a Nikon Optiphot Research microscope. Standard point count stereology techniques using a 10 mm×10 mm eyepiece grid reticular are used.

Total callus area is measured at 125× magnification as an index of the overall intensity of the healing reaction. Area fractions of bone, cartilage, and fibrous tissue are measured at 250× magnification to examine the relative contribution of each tissue to callus formation. Since the dimensions of the osteotomy gap reflect the baseline (time 0), a measurement of bone area at subsequent time intervals is used to indicate the rate of bone infill. Statistical significance is assessed using analysis of variance, with post-hoc comparisons between groups conducted using Tukey's studentized range t test.

Example II

Mechanical Properties of New Bone Formation

The mechanical properties of new bone formed during gene transfer are measured using, e.g., whole bone torsion tests that create a stress state in which the maximum tensile stresses occur on planes that lie obliquely to the bone's longitudinal axis. Such tests may provide important inferences about the mechanical anisotropy of callus tissue and the degree of osseous integration of new bone tissue. These tests are particularly advantageous in the evaluation of fracture specimens, e.g., the irregular shape of callus tissue typically precludes the use of whole bone 4-point bending tests because it is difficult to reproducibly align the points from specimen to specimen.

Femurs are tested on an MTS Servohydraulic Testing Machine while moist and at room temperature. A torque sensor and rotary variable displacement transducer provides data for torque-angular displacement curves. Specially designed fixtures support each bone near the metaphyseal-diaphyseal junctions, and apply a 2-point load to the diaphysis. Tests are conducted at a constant rate of displacement equal to 20 degrees/sec. A 250 inch-ounce load cell measures the total applied force. All bones are tested while moist and room temperature. Torque and angular displacement data are acquired using an analog-to-digital converter and a Macintosh computer and software. From this data, the following variables are calculated: a) maximum torque, b) torsional stiffness, the slope of the pre-yield portion of the curve determined from a linear regression of the data, c) energy to failure, the area under the torque-angular displacement curve to the point of failure, and d) the angular displacement ratio, the ratio of displacement at failure to displacement at yield. Statistical significance is determined Analysis of Variance followed by multiple comparisons with appropriate corrections (e.g., Bonferroni).

This invention also provides a means of using osteogenic gene transfer in connection with reconstructive surgery and various bone remodeling procedures. The techniques described herein may thus be employed in connection with the technology described by Yasko et al., (1992), Chen et al., (1991) and Beck et al. (1991), each incorporated herein by reference.

Example III

Gene Constructs

Numerous genes, preferably mammalian or human genes, may be used as wound-healing or osteogenic genes for use in the matrix-gene transfer technology of the present invention. U.S. application Ser. No. 08/199,780, filed Feb. 18, 1994, now U.S. Pat. No. 5,763,416, is incorporated herein by reference for purposes including incorporating the text concerning the preparation and use of the active fragment of the human parathyroid hormone gene (hPTH1-34), expression vectors containing the hPTH1-34 gene and the use of the hPTH1-34 gene in gene transfer to promote wound-healing, as exemplified by new bone formation. Hendy et al. (1981) is also incorporated herein by reference for purposes including describing the DNA and amino acid sequences of hPTH1-34.

U.S. application Ser. No. 08/199,780, now U.S. Pat. No. 5,763,416, is also incorporated herein by reference for purposes including incorporating the text concerning the preparation and use of the mouse bone morphogenetic protein-4 (BMP-4) gene, expression vectors containing the BMP-4 gene and the use of the BMP-4 gene in gene transfer to promote wound-healing, as exemplified by new bone formation. The amino acid sequence encoded by the mouse BMP-4 transgene, including the tag, is represented by SEQ ID NO:1 in U.S. application Ser. No. 08/199,780, filed Feb. 18, 1994, now U.S. Pat. No. 5,763,416, incorporated herein by reference for purposes including the incorporation of the referenced sequence. The human sequence for BMP-4 is well known to those of skill in the art and has been deposited in Genbank.

Placement of the HA epitope at the extreme carboxy terminus does not interfere with the function of the recombinant molecule sequence in vitro or in vivo. The advantage of the epitope is for utilization in immunohistochemical methods to specifically identify the recombinant mouse BMP-4 molecule in osteotomy tissues in vivo, e.g., the epitope can be identified using a commercially available monoclonal antibody (Boehringer-Mannheim).

Each of U.S. application Ser. No. 08/199,780, filed Feb. 18, 1994, now U.S. Pat. No. 5,763,416; U.S. application Ser. No. 08/316,650, filed Sep. 30, 1994% now U.S. Pat. No. 5,942,496; and U.S. application Ser. No. 08/479,722, filed Jun. 7, 1995, now U.S. Pat. No. 6,074,840; are also incorporated herein by reference for the purposes of describing the preparation and use of further isolated novel fibrillin-like genes, particularly latent LTBP-2 and LTBP-3.

For LTBP-2, the nucleotide sequence of SEQ ID NO:1 and the deduced amino acid sequence of SEQ ID NO:2 from U.S. application Ser. No. 08/479,722, now U.S. Pat. No. 6,074,840 are specifically incorporated herein by reference. For LTBP-3, the nucleotide sequence of SEQ ID NO:2 and the polypeptide sequence of SEQ ID NO:3 from U.S. application Ser. No. 08/316,650, now U.S. Pat. No. 5,942,496 are specifically incorporated herein by reference, as are the nucleotide sequence of SEQ ID NO:3 and the polypeptide sequence of SEQ ID NO:4 from U.S. application Ser. No. 08/479,722, now U.S. Pat. No. 6,074,840. The LTBP-3 protein in particular includes a signal peptide, and five structurally distinct regions (Region 1-Region 5), as described in U.S. application Ser. No. 08/479,722, now U.S. Pat. No. 6,074,840, incorporated herein by reference.

U.S. application Ser. No. 08/752,919, filed Nov. 20, 1996, now abandoned, is also incorporated herein by reference in entirety for purposes including describing the preparation and use of further isolated novel genes, particularly activins/inhibins, such as liver activins. U.S. application Ser. No. 08/752,919, now abandoned is particularly incorporated for its teachings concerning vertebrate activins expressed in the liver. Activin $\beta_C$ and $\beta_E$ subunit genes and proteins, and domains and fragments thereof, are described; as are other members of the liver activin subgroup; liver activin genomic regulatory elements that regulate the expression of liver activins; antisense sequences and ribozymes; host cell expression systems, including hepatocytes; liver activin proteins, fusion (chimeric) proteins, polypeptides and peptides; antibodies to liver activin proteins; diagnostic detection methods; transgenic animals that express a liver activin; recombinant knock-out animals that do not express liver activin(s); antagonists and agonists of the liver activins; methods of modulating liver activin gene expression activity to regulate cell growth and/or differentiation and to treat abnormalities related thereto, including intracorporeal and extracorporeal liver tissue growth and regeneration; and methods of promoting hematopoiesis, local and systemic bone growth and regeneration; and compounds that effect all such modulatory, growth and/or regenerative processes.

Figure 2A:
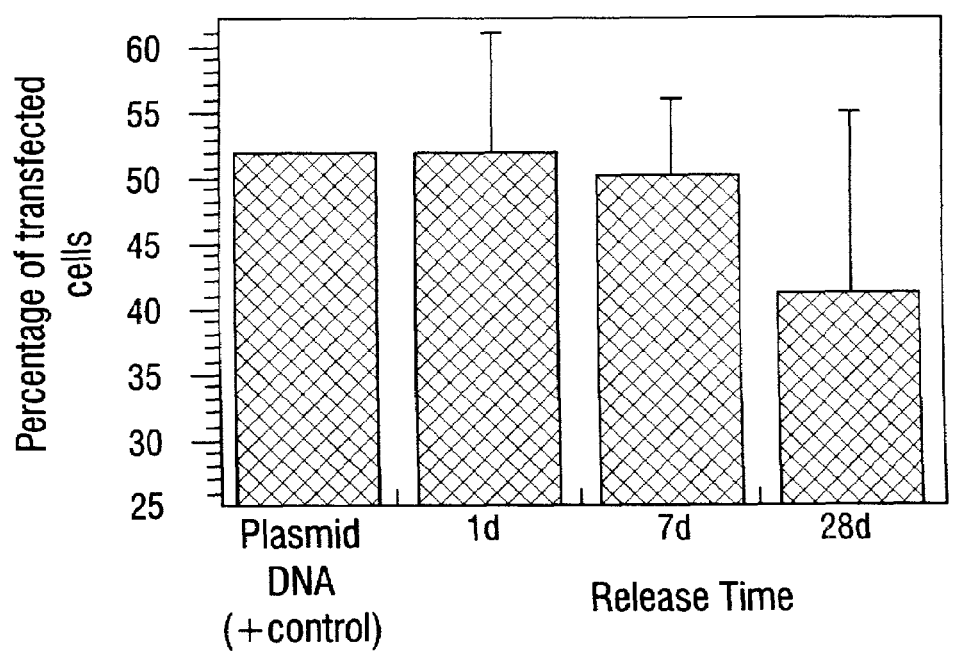
FIG. 2A and FIG. 2B. In vitro transfection by plasmid DNA released at different times from PLGA polymer sponges (75:25 (i.v.=0.2)) fabricated by the gas foaming procedure. Values represent mean and standard deviations. Percentage of cells transfected (FIG. 2A). The percentage of cells transfected was calculated by calcium precipitating unincorporated plasmid DNA (+control) and plasmid DNA collected at different times of release. Quantification of enzymatic activity (FIG. 2B). The quantification of enzymatic activity of the produced protein was determined by a mock transfection (-control), transfection using unincorporated plasmid DNA (+control) and plasmid DNA collected at different times of release. The relative light units (RLU) was recorded from a luminometer and normalized per milligram of total protein. Values represent mean and standard deviation.

In particular, the nucleotide sequence of FIG. 1 of U.S. application Ser. No. 08/752,919, now abandoned is specifically incorporated herein by reference, as is the amino acid sequence of the encoded protein, as shown in FIG. 2 of U.S. application Ser. No. 08/752,919, now abandoned.

U.S. application Ser. No. 08/752,919, now abandoned is particularly incorporated by reference for the purposes of describing activin gene compositions and activin gene-matrix compositions, and methods of using such compositions in the regulation of cell growth and/or differentiation including, but not limited to, stimulating liver regeneration, bone growth and hematopoiesis.

Example IV

Detection Following Transgene Expression

Suitable techniques for the detection of mRNA in tissue obtained from the site of wound healing, e.g., the site of bone regeneration, are known to those of skill in the art. Such techniques are also detailed in U.S. application Ser. No. 08/199,780, filed Feb. 18, 1994, now U.S. Pat. No. 5,763,416, incorporated herein by reference for purposes including describing suitable mRNA detection techniques. Northern analyses may also be employed.

mRNA detection techniques are useful for detecting expression of the transgene mRNA itself, and also in detecting the expression of hormones, growth factor receptors and other molecules in the tissues. For example, in order for a parathyroid hormone (PTH) transgene to function as an osteogenic agent, it is likely that there is a requirement for the PTH/PTHrP receptor to be expressed in the bone repair tissue itself. The presence of PTH/PTHrP receptor expression in osteotomy repair tissue has been demonstrated in the rat osteotomy model (U.S. application Ser. No. 08/199,780, filed Feb. 18, 1994, now U.S. Pat. No. 5,763,416, incorporated herein by reference for this purpose).

Proteins expressed from the transgenes may also be detected immunohistochemically and by substrate utilization assays. U.S. application Ser. No. 08/199,780, filed Feb. 18, 1994, now U.S. Pat. No. 5,763,416, is also incorporated herein by reference for the purpose of describing suitable immunohistochemical and substrate utilization assays. Commercially available radioimmunoassay kits are also suitable for use in such protocols, and may detect the protein product of the transgene itself, or an epitope specifically added for the purposes of immunohistochemical detection (e.g., using a specific antibody that recognizes the HA epitope, Majmudar et al., 1991).

Example V

Gene-Matrix Transfer into Regenerating Bone Ex Vivo

Although the present inventors have already demonstrated the success of direct gene transfer into regenerating bone in vivo (Example VI through Example VIII), the use of ex vivo treatment protocols is also contemplated. In such embodiments, bone progenitor cells are isolated from a particular animal or human subject and maintained in an in vitro environment. Suitable areas of the body from which to obtain bone progenitor cells are areas such as the bone tissue and fluid surrounding a fracture or other skeletal defect (whether or not this is an artificially created site) and from the bone marrow. Isolated cells are then contacted with the DNA or recombinant viral composition, with or without a matrix, allowing the cells to take up the DNA (or be infected by the recombinant virus). The stimulated cells are then returned to the site in the animal or patient where bone repair is to be stimulated.

Example VI

Gene-Matrix Transfer into Regenerating Bone In Vivo

Direct gene transfer into regenerating bone in vivo was demonstrated by marker gene transfer into cells in the rat osteotomy model using both β-galactosidase and luciferase.

Aliquots of a fibrous collagen implant material were soaked in solutions of pure marker gene DNA. The implant materials were then placed in the osteotomy site, and their expression determined. As shown in U.S. application Ser. No. 08/199,780, filed Feb. 18, 1994, now U.S. Pat. No. 5,763,416, incorporated herein by reference for this purpose, both marker genes were successfully transferred and expressed, without any failures, as demonstrated by substrate utilization assays. Since mammalian cells do not normally synthesize either marker gene product, this provides direct evidence that osteotomy repair cells were transfected in vivo and then expressed the β-galactosidase and luciferase transgenes as a functional enzymes.

Example VII

Virus-Gene-Matrix Transfer into Regenerating Bone In Vivo

In vivo gene transfer into regenerating bone was also achieved using matrix-adenovirus-mediated transfer. Adenovirus constructs may be prepared as described by Stratford-Perricaudet et al., 1992, and Davidson et al., 1993, each incorporated herein by reference. Successful adenoviral gene transfer of marker gene constructs into bone repair cells was demonstrated in the rat osteotomy model, and fully described in U.S. application Ser. No. 08/199,780, filed Feb. 18, 1994, now U.S. Pat. No. 5,763,416; U.S. application Ser. No. 08/631,334, filed Apr. 12, 1996, now U.S. Pat. No. 5,962,427; and PCT Application Serial No. PCT/US97/07301, filed Apr. 11, 1997 (WO 97/38729); each incorporated herein by reference for this purpose.

CMVlacZ is an example of a replication-defective adenoviral vector that can replicate in permissive cells (Stratford-Perricaudet et al., 1992). In the vector employed, the early enhancer/promoter of the cytomegalovirus (CMV) is used to drive transcription of lacZ with an SV40 polyadenylation sequence cloned downstream from the reporter gene (Davidson et al., 1993). pAd.RSV4 has essentially the same backbone as pAdCMVlacZ, however the CMV promoter and the single BglII cloning site has been replaced in a cassette-like fashion with a BglII fragment that consists of an RSV promoter, a multiple cloning site, and a poly($A^+$) site. The greater flexibility of this vector is contemplated to be useful in subcloning osteogenic genes, such as the hPTH1-34 cDNA fragment, for use in further studies.

An Ultra Fiber™ implant was soaked for 6 minutes in a solution of AdCMV lacZ virus ($10^{10}$-$10^{11}$ plaque forming units or PFU/ml) and then implanted into an osteotomy site. The defect was allowed to heal for 3 weeks, during which time the progress of the wound healing and bone regeneration responses were monitored by weekly radiographic examination.

By three weeks, it was estimated that 40% of the defect was filled with callus tissue. The mammalian host was sacrificed and tissues were fixed in Bouins fixation and then demineralized for 7 days using standard formic acid solutions. The results obtained conclusively demonstrated expression of the marker gene product in chondrocyte-like cells of the osteotomy gap. The nuclear-targeted signal has also been observed in pre-osteoblasts.

U.S. application Ser. No. 08/662,341, filed Jun. 12, 1996, now U.S. Pat. No. 6,143,037, and PCT Application Serial No. PCT/US97/10079, filed Jun. 11, 1997 (WO 97/47254), are also each specifically incorporated herein by reference without disclaimer for the purposes of describing the preparation and use of coated medical devices as part of a gene transfer protocol for DNA delivery to bone repair cells. The devices described can be effectively used with the aspects of this invention that concern gene delivery to bone cells and tissues.

Example VIII

Osteogenic Gene-Matrix Transfer Stimulates Bone Regeneration

Matrix-mediated gene transfer has also been employed to create transfected cells that constitutively express recombinant hPTH1-34 in vivo and to stimulate bone formation (fully described in U.S. application Ser. No. 08/199,780, filed Feb. 18, 1994 now U.S. Pat. No. 5,763,416, incorporated herein by reference for this purpose).

In the 5 mm rat osteotomy model described above, it was found that PTH transgene expression stimulates bone regeneration/repair in live animals. This is a particularly important finding as it is known that hPTH1-34 is a more powerful anabolic agent when given intermittently as opposed to continuously, and it is the continuous-type delivery that results from the gene transfer methods used here.

Example IX

Gene-Matrix Transfer to Soft Tissues In Vivo

As described in U.S. application Ser. No. 08/631,334, filed Apr. 12, 1996, now U.S. Pat. No. 5,962,427, and PCT Application Serial No. PCT US97/07301, filed Apr. 11, 1997 (WO 97/38729), each incorporated herein by reference for this purpose, there is a clinical need to stimulate scar formation during the repair of soft tissues in order to enhance the mechanical competence of the injured tissue.

A model system has been developed in which incisions in adult rat skeletal muscle are made and a suture preparation coated with a preparation of sustained release PLGA particles and plasmid DNA is used as a skeletal muscle gene delivery device. To demonstrate the feasibility of such DNA-coating compositions and methods, a surgical suture was coated with marker DNA encoding human placental alkaline phosphatase and used to suture rat muscle tissue. The study demonstrates successful transfer and expression of DNA in the tissue repaired with the coated suture.

0.2 mL of a solution containing marker DNA encoding human placental alkaline phosphatase (1 mg DNA, 0.5 mM Tris-EDTA, 0.5 mM EDTA, pH 7.3) was added to 1.5 ml of a PLGA/chloroform solution (3% (w/v) 50/50 polylactic polyglycolic acid PLGA co-polymer, average MW 90,000, inherent viscosity 1.07). The solution was emulsified by vortexing for 2 minutes followed by sonicating for 30 sec at about 0° C. using a microtip probe-type sonicator at 55 Watts output. This process yielded an emulsion that looked very milky.

A hole was pierced in a piece of Teflon-coated foil (Norton Performance Plastic Corp., Akron, Ohio) using a 22-gauge needle. On the hole was placed a drop (about 60 µL) of the DNA-PLGA emulsion. A 70 cm length of 3-0 chromic suture (Ethicon) was drawn through the hole to coat the suture. As the suture passed through the hole it became coated with a thin (ca. 30 µm-thick), uniform coating of the coating composition. The suture was allowed to air dry for about 3 minutes, and the coating process repeated 15 times, allowing each coat to air dry. The coated suture was examined by electron microscopy (150×) and the suture was found to be coated with a uniform coating of DNA-PLGA. The coating remained intact even after passing the suture through tissue multiple times.

The suture prepared above was sewn into the skeletal muscle tissue of two normal adult rats with satisfactory surgical results. The suture exhibited good tie-down properties. One week later, muscle plus suture was dissected, snap frozen in liquid nitrogen and ground into a powder. The powder was incubated in 200 µl lysis buffer, exposed to three freeze-thaw cycles and clarified. The clear liquid was assayed for alkaline phosphatase activity using standard methods after incubation at 65° C.

The results indicated that rat skeletal muscle sewn with coated sutures and retrieved after one week exhibited alkaline phosphatase activity, signifying that the marker alkaline phosphatase gene was expressed in the muscle tissue. Control retrievals showed no significant alkaline phosphatase activity. These data demonstrate that emulsions can be used to effectively coat sutures and deliver genes to proliferating repair cells in vivo.

Each of U.S. application Ser. No. 08/662,341, filed Jun. 12, 1996, now U.S. Pat. No. 6,143,037, and PCT Application Serial No. PCT/US97/10079, filed Jun. 11, 1997 (WO 97/47254), are specifically incorporated herein by reference without disclaimer for the purposes of describing the preparation and use of coated medical devices. Such devices can be used to advantage in combination with the present invention to facilitate repair of soft tissues, e.g., after injury.

Example X

Gene-Matrix Transfer to Blood Vessels In Vivo

As also described in U.S. application Ser. No. 08/631,334, filed Apr. 12, 1996, now U.S. Pat. No. 5,962,427, and PCT Application Serial No. PCT/US97/07301, filed Apr. 11, 1997 (WO 97/38729), each incorporated herein by reference for this purpose, there is a clinical need to prevent excessive fibrosis (restenosis), as may occur during blood vessel repair following angioplasty. This can be accomplished by the delivery of genes that encode lysyl oxidase inhibitors, or by transfer of genes that encode certain TGF-βs. There is, in addition, a clinical need to regulate angiogenesis, e.g., in vascular insufficiency disorders, where the goal is to stimulate new vessel formation in order to prevent tissue hypoxia and cell death.

A model system has been developed in which repair cells in large blood vessels in certain rabbits are transfected with a preparation of sustained release PLGA nanoparticles and plasmid DNA. Repair cells are present because the blood vessels in the chosen rabbits harbor a foam cell lesion that mimics clinical atherosclerosis in humans. The present example demonstrates the ability to deliver and express gene constructs into large blood vessel repair cells.

New Zealand white rabbits of either sex, weighing 3.1 to 3.5 kg, were used. Rabbits were anesthetized using Ketamine (35/mg/Kg) and Xylazine (5 mg/kg) given intramuscularly, and maintenance anesthesia was achieved with intravenous ketamine (8 mg/kg) administered via a marginal vein. Approximately 2 cm segments of both iliac arteries between the descending aortic bifurcation and inguinal ligament were isolated, tied off proximally, and all small branches of this arterial segments were ligated. Local thrombi were prevented by the ear-marginal vein administration of heparin (100 mg). A balloon angioplasty catheter (2.0 mm balloon) was introduced via an iliac arteriotomy into iliac arteric segments and balloon was dilated for 1 minute at 8 atm pressure.

Following balloon dilatation, the angioplasty catheter was removed, 20 mg of heparin was injected intra-arterially to prevent distal thrombosis. Both ends of iliac artery were tightened with 10.0 silk, and a 5 mg/ml DNA-PLGA nanoparticle suspension was infused in each iliac artery over 3 minutes at 0.5 atm. The wound was sutured. Rabbits were sacrificed 2 wk after the balloon angioplasty and nanoparticle delivery. Through a vertical lower abdominal incision, both iliac arteries were isolated. A 2 cm segment of iliac artery was excised bilaterally. Carotid arteries from rabbit was taken as a control sample. The tissue was preserved in liquid nitrogen for alkaline phosphatase assay.

The results of the phosphatase expression assays indicate that a nanoparticle plus DNA formulation was capable of delivering nucleic acids to repair cells in the iliac arterics of adult rabbits injured with a balloon catheter. Both the right and left iliac arterics were positive for phosphatase activity after exposure to nanoparticle matrix-DNA formulations. No phosphatase activity was detected in the control aorta. These positive results indicate that, upon exposure to a gene activated matrix, repair cells in large blood vessels take up and express nucleic acid molecules.

U.S. application Ser. No. 08/662,341, filed Jun. 12, 1996, now U.S. Pat. No. 6,143,037, and PCT Application Serial No. PCT/US97/10079, filed Jun. 11, 1997 (WO 97/47254), are also each specifically incorporated herein by reference without disclaimer for the purposes of describing the preparation and use of coated medical devices for therapeutic intervention connected with blood vessels. Such devices can be advantageously used with those aspects of the present invention that concern gene delivery to blood vessels.

Example XI

Controlled Pore Matrix Preparation

A. Materials and Methods
  1. Matrix Processing

U.S. Provisional Application Ser. No. 60/042,198, filed Mar. 31, 1997, the priority document for U.S. Pat. Nos. 6,281, 256 and 6,797,738 and WO 98/44027, PCT Application No. PCT/US98/06188 (WO 98/44027), filed Mar. 31, 1998 and designating the U.S. and U.S. patent application Ser. No. 09/402,119, filed Sep. 20, 1999, now U.S. Pat. No. 6,281,256, are each specifically incorporated herein by reference without disclaimer for the purpose of even more fully describing controlled and open pore matrix preparation. In the following examples, all temperatures are set forth uncorrected in degrees Celsius and unless otherwise indicated. All parts and percentages are by weight.

Pellets of an 85:15 copolymer of D,L-lactide and glycolide (PLGA) were purchased from Boehringer Ingelheim (Henley, Montvale, N.J.), and utilized to fabricate polymer matrices. The intrinsic viscosity of the polymer was about 1.3-1.7.

Polymer pellets were ground using a Tekmar grinder (Bel-Art Products, Pequannock, N.J.), and sieved to obtain particles ranging from 106 to 250 mµ. In certain studies the polymer particles were mixed with sodium chloride particles (Mallinckrodt, Paris, Ky.). The salt particles were sieved to yield a range of sizes, and the weight ratio of NaCl:PLGA masses ranged from 0 to 50. In all cases, the total mass of PLGA and NaCl was held constant at 0.8 g.

The mixtures of PLGA and NaCl were loaded into a KBr die (1.35 cm in diameter; Aldrich Chemical Co., Milwaukee, Wis.), and compressed at 1500 psi for 1 min using a Carver Laboratory Press (Fred S. Carver, Inc., Menominee Falls, Wis.) to yield solid discs (thickness=3.4 mm). The samples were then exposed to high pressure $CO_2$ gas (800 psi) for 48 h to saturate the polymer with gas. A thermodynamic instability was then created by decreasing the gas pressure to ambient pressure. This led to the nucleation and growth of $CO_2$ pores within the polymer matrices. The NaCl particles were subsequently removed from the matrices by leaching the matrices in dd$H_2$O for 48 h. All processing steps were performed at ambient temperature.

Porous sponges were also fabricated using a previously described solvent casting-particulate leaching technique (Mikos et al., 1994; incorporated herein by reference). In this process, PLGA was dissolved in chloroform (Mallinckrodt; Paris, Ky.) to yield a solution of 10% (w:v), and 0.12 ml of this solution was loaded into Teflon cylinders (diameter 0.5 cm, Cole Parmer) packed with 0.4 g of sodium chloride particles sieved to a size between 250 and 500 mm. Following solvent evaporation, polymer films with entrapped salt particles (3 mm thick) were carefully removed from the molds. The salt was removed by immersing films in distilled water for 48 h.

2. Characterization

The porosity of samples was initially determined by gross measurements and weights after processing using the following equation:

$$\text{porosity}(\%) = 1 - [(\text{weight/volume})/(\text{density of polymer})] \times 100 \qquad \text{Eqn. 1}$$

The samples were imaged using a scanning electron microscope (ISI-DS 130, Topcon Technologies, Pleasanton, Calif.). The samples were gold coated using a Sputter Coater (Desk II, Denton Vacuum, Cherry Hill, N.J.), and the microscope was operated at 10 kV to image the samples. Polaroid 55 film was used for the photomicrographs.

Compression and tensile testing were performed on an MTS Bionix 100 (Sintech, Research Triangle Park, N.C.). Samples were cut into 1×1 cm squares for compression testing. For tensile testing, the samples (1×1 cm) were attached to cardboard using epoxy glue. A 7 mm slot was cut into the center of the card board and the sample was centered, then glued to standardize the gage length. Compression and tensile tests were performed with a constant strain rate (1 mm/min). The moduli were determined from the slopes in the elastic portion of the stress-strain diagram.

Thermogravimetric analysis was utilized to determine the amount of salt residue that remained in the sponge after leaching. Matrices were heated from 150° C. to 300° C. at a constant rate of 10° C./min, and the residual mass was monitored.

B. Results

1. Integrity, Porosity and Pore Structure of Foamed Matrices

Gas foaming of solid polymer discs alone led to the formation of highly porous matrices. However, these matrices had a non-porous skin on the external surfaces and the pores were largely closed, as the inventors had contemplated from their previous studies (Mooney et al., 1996; incorporated herein by reference). In contrast, gas-foaming and subsequent leaching of discs containing a high percentage (95%) of large (250<d<425 µm) NaCl particles, according to the invention, led to the formation of highly porous, open pore matrices with no evidence of an external, non-porous skin.

The pore structure observed in cross-sections of the matrices of the present invention was similar to that observed in cross-sections of matrices formed with a solvent-casting/particulate leaching (SC/PL) technique. However, the pore structure of matrices formed from the SC/PL process is often not uniform throughout the matrix due to evaporation of the organic solvent and subsequent increase in the polymer concentration of the remaining solution entrapped within the salt bed. For example, the surface of the SC/PL matrices that is adjacent to the glass coverslip during processing is typically less porous than the remainder of the matrix. In contrast, the pore structure of gas foamed-particulate leached (GF/PL) matrices of the present invention was uniform throughout the matrix and on the exterior surfaces.

TGA analysis of the matrices of the present invention indicated that negligible amounts of NaCl remained after leaching. There was a trace of a white residue left in the dish. To confirm that the gas foaming was responsible for the formation of stable matrices, control samples were compression molded, but not foamed. Leaching of the NaCl from these matrices led to complete breakdown of the matrices.

2. The Effects of NaCl:PLGA Ratio Variation on Porosity and Pore Structure

The ratio of NaCl:PLGA and the size of NaCl particles in GF/PL matrices were next varied to determine the range of porosity and pore structure that could be obtained with this process (Table 1). The gross porosity of these matrices increased from 85.1%×2.3 to 96.5%×0.5 as the ratio of NaCl:PLGA was similarly increased. At constant NaCl (95%), the increase in salt particle diameter had very little effect on the overall porosity. However, as the salt diameter was increased, the pore size increased in parallel.

TABLE 1

| NaCl Concentration (%) | Gross Porosity of Sponges | | |
|---|---|---|---|
| | Diameter (µm) | | |
| | 106-250 | 250-425 | >425 |
| 80 | — | 85.1 ± 2.3 | — |
| 90 | 87.3 ± 1.9 | 91.5 ± 1.4 | — |
| 95 | 93.9 ± 0.9 | 94.6 ± 0.9 | 95.0 ± 0.8 |
| 97 | — | 96.5 ± 0.5 | — |

3. Matrix Stability

The stability of the matrices was next assessed using compressive and tensile mechanical tests. In general, the GF/PL matrices exhibited improved mechanical properties as compared to the SC/PL matrices. The average compression moduli were 159×130 kPa and 289×25 kPa for the SC/PL and GF/PL matrices, respectively. The average tensile moduli were 334±52 kPa for the SC/PL matrices and 1100±236 kPa for the GF/PL matrices (Table 2). This data represents a 80% increase in compression strength and a 300% increase in tensile strength.

TABLE 2

Mechanical Properties

| Method | Compressive Modulus (kPa) | Tensile Test | |
|---|---|---|---|
| | | Modulus (kPa) | Elongation @ break (%) |
| Solvent/leach | 159 ± 130 | 334 ± 52 | 17.5 ± 1.9 |
| Foam/leach | 289 ± 25 | 1100 ± 236 | 12.0 ± 1.3 |

Example XII

Tissue Development on Controlled Pore Matrices

A. Materials and Methods

1. Cell Studies

The smooth muscle cells (SMC) used in these studies were isolated and cultured using a modification of the techniques described in Rothman et al. (1992; incorporated herein by reference). In brief, the cells were isolated from aortas of 300-350 g adult male Lewis rats (Charles River Laboratories, Wilmington, Mass.) using an enzymatic dissociation. After fat, adventitia, and connective tissue surrounding the arteries were removed by blunt dissection, the SM tissue was cut into multiple small pieces and placed into a spinner flask containing an enzymatic dissociation buffer at 37° C. This buffer contains 0.125 mg/mL elastase (Sigma Chemical Co., St. Louis, Mo., USA), 1.0 mg/mL collagenase (CLS type I, 204 units/mg, Worthington Biochemical Corp., Freehold, N.J., USA), 0.250 mg/mL soybean trypsin inhibitor (type 1-S, Sigma), and 2.0 mg/mL crystallized bovine serum albumin (BSA, Gibco/Life Technologies, Gaithersburg, Md.).

After 90 minutes of incubation, the suspension was filtered through a 100 5 m Nitex filter (Tetko, Inc., Briarcliff Manor, N.Y.) and centrifuged at 200 g for 5 min. The pellet was resuspended in Medium 199 (Sigma) supplemented with 20% (v/v) fetal bovine serum (FBS, Gibco), 2 mM L-glutamine (Gibco), and 50 units/mL penicillin-streptomycin (Gibco). The cells were cultured on tissue culture plastic in a humidified 5% $CO_2$ atmosphere with the medium (Medium 199, 10% (v/v) fetal bovine serum, 50 units/mL penicillin-streptomycin) changed every other day. Cells at passage 17 were used in these studies.

The matrices were seeded with SMCs by placing a 40 mL cell suspension containing $3.14 \times 10^7$ cells/mL on top of each matrix and allowing the cell suspension to absorb into the matrix. Matrices were contained in tissue culture dishes and incubated at 37° C. for ~36 h. Next, the polymer matrices were cultured for two weeks and placed in a spinner flask (100 mL, Bellco Glass, Inc., Vineland, N J, USA) stirred at 40 RPM.

The number of cells in the matrices was determined by measuring the DNA content in enzyme-digested triplicate samples using Hoechst 33258 dye and a fluorometer (Hoefer DyNA Quant 200, Pharmacia Biotech, Uppsala, Sweden). For scanning electron microscopic examination, samples were fixed in 1% glutaraldehyde and 0.1% formaldehyde for 30 min and 24 h, respectively, dehydrated in a graded series of ethanol/water solutions, dried, and then sputter-coated with gold. A scanning electron microscope (ISI-DS 130, Topcon Technologies) was operated at 10 kV to image samples. Histological sections were prepared by fixing cell-polymer matrices (10% formalin), dehydrating, embedding, sectioning and staining with hematoxylin and eosin or VerhoefUs using standard techniques.

B. Results

1. Tissue Development

As described in U.S. Provisional Application Ser. No. 60/042,198, filed Mar. 31, 1997, the priority document for U.S. Pat. Nos. 6,281,256 and 6,797,738 and WO 98/44027, specifically incorporated herein by reference without disclaimer, the ability of the GF/PL matrices to allow cell adhesion and tissue formation was demonstrated in in vitro studies. SMCs adhered to the GF/PL matrix and covered the available surface area following seeding. A significant increase in cell number was noted after 2 wk in culture. The average cell density was $1.71 \times 10^7$ cells/mL and $3.05 \times 10^7$ cells/mL at 0 and 2 wk, respectively. This is a 43.8% increase in cell density.

The cells filled the pores of the matrix and created a new three-dimensional tissue within the synthetic matrix. Most of the cell growth occurred around the periphery of the matrix in a relatively uniform manner, and a low cell concentration was observed in the center of the matrices at 2 wk. There was no observed change in the size and shape of the matrices over this time period.

Example XIII

Controlled Pore Matrices Containing DNA

Controlled, open pore matrices containing plasmid DNA can be fabricated by a one-step gas foaming/particulate leaching process, generally as described in Example XI. In this process, polymer particles and plasmid DNA are mixed with sodium chloride, compressed into a disc, and placed in a pressure vessel with a high pressure gas. Release of the pressure causes the polymer particles to expand. Collisions between adjacent polymer particles cause them to fuse, thereby producing an interconnected structural matrix. Pores are formed within the matrix by leaching out the salt and leaving a matrix with an open pore structure (Example XI).

Controlled, open pore matrices containing plasmid DNA can also be fabricated by a two-step gas foaming/particulate leaching process. The two-step process involves mixing the polymer with plasmid, compressing into a disc, and placing in a pressure vessel with high pressure gas. Release of the pressure produces an interconnected matrix; however, the polymer has a closed pore structure. If cellular invasion is not desired during use of the plasmid-containing matrix, the closed pore polymer can be used for sustained delivery. The second step of this two-step process involves grinding the initial matrix into small pieces, mixing them with salt, pressing into a disc, and placement in a pressure vessel. The matrix is then foamed and the salt removed via leaching.

For use in Example XIV, 75:25 and 85:15 copolymers of D,L-lactide and glycolide (PLGor PLGA) (Henley, Montvale, N.J., USA) were utilized to fabricate matrices with a gas foaming/particulate leaching process (Example XI; Harris et al., 1998; incorporated herein by reference). 75:25 PLG was purchased and used as a powder. The 85:15 PLG was purchased in pellet form and ground to a particle size ranging from 106 to 250 μm.

To incorporate DNA, 40 mg PLG was mixed with an aqueous solution (pH 7.4) containing 5 mM Hepes, 10% mannitol and 1 mg plasmid DNA. Following vigorous mixing, samples were frozen with liquid nitrogen, and lyophilized. The remaining powder was mixed with NaCl and compression molded. The resulting disc was allowed to equilibrate within a high pressure $CO_2$ environment. A rapid reduction in pressure causes the polymer particles to expand and fuse into an interconnected structure. NaCl was leached from the sponge by immersion in water. For scanning electron microscopic examination, samples were dried and sputter-coated with gold.

Example XIV

Release of DNA from Controlled Pore Matrices

1. Incorporation

Plasmid DNA was purified using Qiagen™ reagents (Qiagen Inc., Santa Clarita, Calif., USA). The plasmid used in the release studies was the pNGVL-1 vector containing the gene for nuclear targeted β-galactosidase (nt β-gal).

Plasmid DNA encoding a nuclear targeted β-galactosidase (nt β-gal) was incorporated directly into poly(lactide-co-glycolide) (PLG) matrices processed into three-dimensional matrices using a gas foaming process (Example XIII, Harris et al., 1998; incorporated herein by reference). These matrices are highly porous (>90%) with an interconnected open pore structure, confirmed by mercury porosimetry (Harris et al., 1998).

Matrices containing plasmid DNA were created from three different PLGA copolymers that have varying degradation rates (Wong and Mooney, 1997; incorporated herein by reference). The mass of plasmid DNA incorporated into matrices of 75:25 copolymer of lactide and glycolide (i.v.=0.2), 85:15 copolymer (i.v.=0.7), and 75:25 copolymer (i.v.=0.7) was determined to be 400±146 μg, 764±77 μg, and 970±61 μg respectively. The incorporation efficiencies were 49±6%, 54±3%, and 60±1% respectively. The incorporation efficiency defined here is based on the amount of plasmid that remains in the matrix after the leach step.

In referring to the polymeric matrices, i.v. means intrinsic viscosity, which is a measure of the molecular weight of the polymer. It is understood to be easier for manufacturers to measure intrinsic viscosity than molecular weight, and so is often report instead of direct molecular weights.

2. Sustained Release

Release studies were performed by immersion of PLGA sponges in Tris-EDTA buffer at 37° C. Buffer was removed with replacement at various times. The concentration of DNA in the release buffer was assayed using Hoechst 33258 dye and a fluorometer (Hoefer DyNA™ Quant 200, Pharmacia Biotech, Uppsala, Sweden). Incorporation efficiency was calculated as the ratio of the total mass released during the release study to the sum of the mass lost during the leach and release. The relative amounts of DNA in the different fractions (supercoiled, nicked) were quantified using NIH Image.

Studies showed that plasmid DNA was released from these polymer matrices over various sustained time frames. A sustained release of plasmid DNA was observed for all three PLG matrices, with times for total release of plasmid ranging from 10 days (75:25 i.v.=0.2) to more than 30 days (75:25 i.v.=0.7) (FIG. 1). In certain instances, DNA was released for up to 160 days.

The structural integrity of the released plasmid was confirmed using gel electrophoresis of samples obtained at different times (1, 7, 28 days) of release. The released plasmid is structurally intact for all times of release. The percentage of DNA in the supercoiled conformation for unincorporated plasmid (positive control DNA used as the starting material) and plasmid collected at 1, 7, and 28 days of release was 64%, 43±6%, 16±7%, and 0±0% respectively, indicating a tendency toward the open conformation and potential nicking of the DNA with later times of release.

These results show that the release kinetics depend on the polymer properties and the processing conditions, although sustained release is observed for all polymers tested. The studies described in the following Examples utilized the 75:25 (i.v.=0.2) PLG for plasmid incorporation and delivery.

Example XV

Cell Transfection Using Controlled Pore-DNA Matrices

The transfection competence of plasmid incorporated and released from matrices was assessed by calcium precipitation and in vitro transfection. 293T cells were transfected with the nt β-gal plasmid collected from the release study at 1, 7, 28 and even 70 days of release. The plasmid DNA was condensed and placed in the media above 293T cells. On the third day, cells were fixed and examined for expression of the plasmid.

The percentage of cells transfected was estimated by staining with X-gal and counting the fraction of cells transfected in 5 randomly chosen locations. β-galactosidase activity was determined using the Galacto-Light chemiluminescent reporter assay for the detection of β-gal (Tropix, Inc. Bedford, Mass., USA). The relative light units (RLU) recorded from a (Turner Designs, Sunnyvale, Calif., USA) luminometer are normalized with respect to the mass of protein present, which was determined using the BCA Protein Assay (Pierce Biochemicals, Rockford, Ill., USA).

Figure 2B:
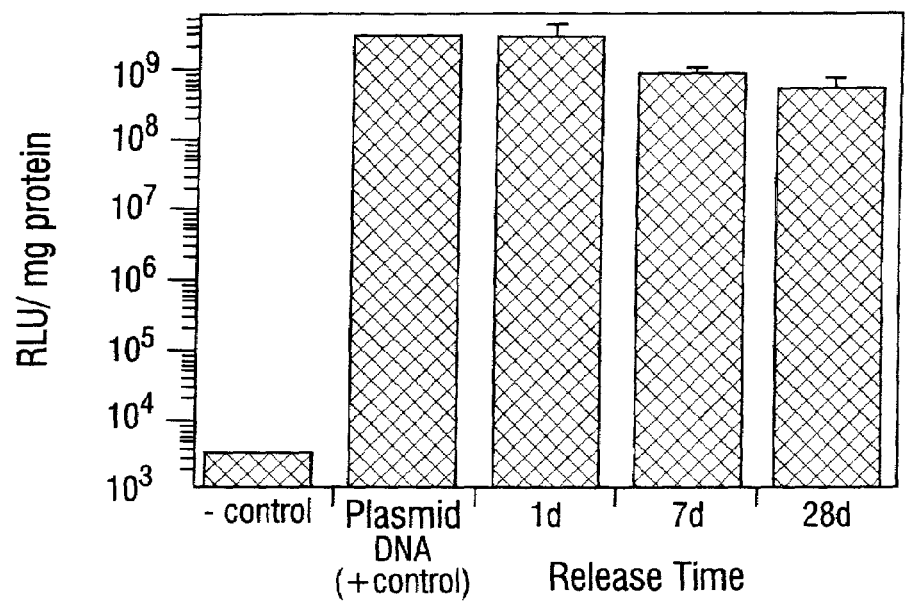

These studies showed a large percentage of the cultured cells were transfected, indicating that the incorporated and released DNA remained functional. The in vitro transfection was quantified by analyzing both the percentage of transfected cells (FIG. 2A), and the enzymatic activity of β-galactosidase in the transfected cells (FIG. 2B). Both remained high for DNA released at all times. Photographs of cells transfected by plasmid DNA released from the PLGA sponges over the first 70 days also supported the quantitative results.

Example XVI

In Vivo Gene Transfer from Controlled Pore-DNA Matrices

In addition to the in vitro studies of Example XV, the present example shows that implantation of the DNA-releasing matrices leads to transfection of the cells within and surrounding the matrix in vivo.

The ability of the released plasmid to transfect cells in vivo was assessed by implantation of the PLGA sponges containing plasmid DNA into subcutaneous tissue of Lewis rats (100-150 g). Marker gene studies utilized nt β-gal for determination of the location of transfected cells. Histological sections cut from frozen tissues were examined following staining with X-gal (Gibco).

The total number of transfected cells per implant was estimated by quantifying the number of transfected cells per section (manual counting), and multiplying by the ratio of the thickness of the matrix (1.3 cm) to the thickness of the section (10 μm).

Controlled pore structural matrices, fabricated as in the previous examples, and loaded with the nuclear targeted β-galactosidase plasmid were implanted into the subcutaneous tissue in the back of Lewis rats. At 2 and 4 weeks, implants were retrieved, sectioned, and stained for expression of the plasmid. At two weeks, a large number of cells surrounding the matrix were transfected. At four weeks, a greater number of transfected cells were detected in the implant periphery, in comparison to the two week sample. Higher magnifications demonstrated the nuclear specific staining of the transfected cells within this region, confirming expression of the delivered nt β-gal plasmid.

The in vivo implantation of an open pore matrix (OPM) sponge fabricated from PLGA and containing nt β-gal plasmid DNA also showed that cells grow into the matrix. A sponge matrix fabricated with the nt β-gal plasmid was prepared and implanted into a rat subdermal site and left for a two week period. The sponge was harvested, fixed, embedded in paraffin, sectioned and stained for expression of the nt β-gal plasmid.

Figure 7:
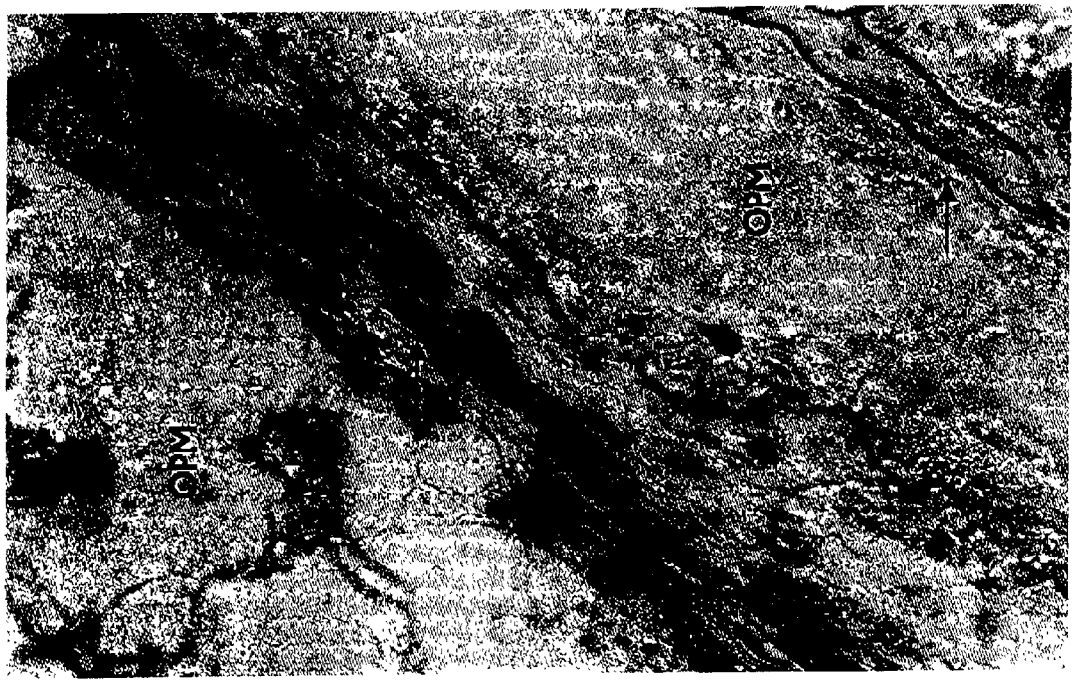
FIG. 7. An open pore matrix (OPM) sponge implant fabricated from PLGA and containing plasmid DNA that encoded nuclear targeted β-galactosidase (nt β-gal) was prepared and implanted into a rat subdermal site as described in Example XVI (Shea et al., 1999; incorporated herein by reference). Following a two week period in-life, the sponge was harvested, fixed, embedded in paraffin, sectioned and processed for bacterial β-galactosidase substrate utilization assay. Shown are granulation tissue fibroblasts with blue nuclei that have grown into the sponge (arrows), taken up the nt β-gal plasmid DNA and expressed functional bacterial β-galactosidase enzyme.
Figure 7:

FIG. 7 shows that granulation tissue fibroblasts have migrated into the sponge (arrows in FIG. 7) and taken up and expressed the nt β-gal plasmid (blue-stained nuclei in FIG. 7). The blue-staining of the histochemical reaction provides direct evidence that cells migrate into the matrix, encounter and express DNA therein.

Example XVII

In Vivo Tissue Growth Using Controlled Pore Matrices with PDGF

The present example shows that implantation of controlled pore structural matrices containing plasmid DNA encoding platelet-derived growth factor (PDGF) stimulates tissue growth in vivo.

PDGF has a major role in the wound healing response and has been shown to affect matrix deposition and to enhance vascularization (Raines and Ross, 1993). The present studies utilized the pNGVL-1 vector containing the gene encoding for human recombinant PDGF B-chain.

These studies first used delivery of the PDGF-encoding plasmid DNA from the structural matrices, wherein release of the nt β-gal plasmid from the same type of matrices served as a control. The potential physiological responses were measured 2 and 4 wks after subcutaneous implantation into Lewis rats. Each animal (n=5) was implanted with both the PDGF-encoding plasmid and the control, nt β-gal plasmid.

Figure 3A:
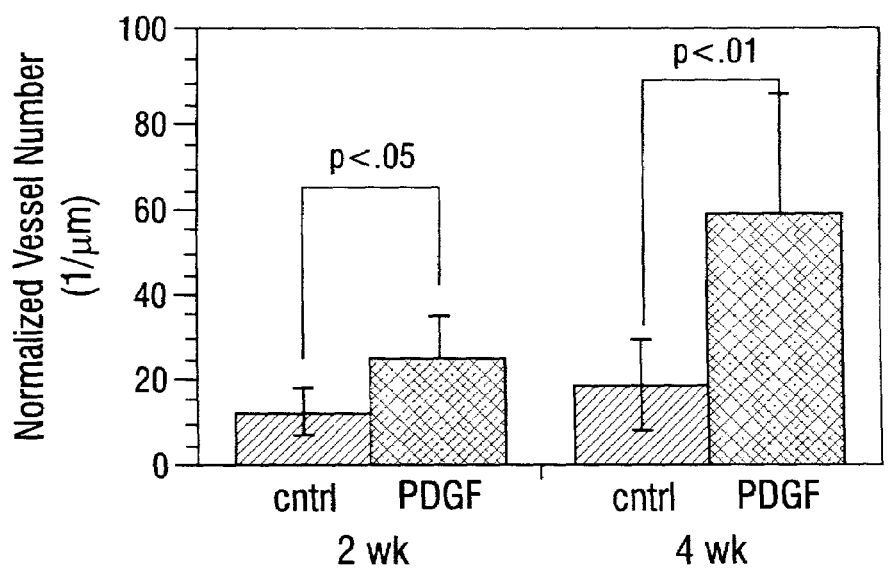
FIG. 3A and FIG. 3B. DNA encoding platelet derived growth factor (PDGF) released from a controlled pore PLGA polymer matrix stimulates blood vessel growth in vivo. PLGA polymer matrices (75:25 (i.v.=0.2)) containing plasmid DNA encoding PDGF or a control (nuclear targeted β-galactosidase) were implanted subcutaneously into rats; samples were retrieved at 2 and 4 weeks and analyzed for the number of blood vessels (FIG. 3A) and the blood vessel area (FIG. 3B). Values represent mean and standard deviations.

Implants retrieved at 2 and 4 weeks were fixed, embedded in paraffin, and sectioned. Histological sections were analyzed for the number of blood vessels (FIG. 3A), the area of blood vessels (FIG. 3B), and the granulation layer thickness (FIG. 4) following staining with the Masson's trichrome procedure.

To quantify the three physiological responses in the histological sections, images were captured to a computer and analyzed. The number and area of blood vessels and the thickness of the granulation layer were determined for each condition. Blood vessel number and area were quantified at 400× magnification. The thickness of the granulation layer was determined from images captured at either 20× or 40×. Statistical analysis of the data was performed using the software program Instat.

The studies demonstrated that tissues containing polymer matrices releasing the PDGF plasmid had an increase in vascularization (FIG. 3A and FIG. 3B), an increase in granulation tissue (FIG. 4) and a loss of adipose tissue adjacent to the muscle layer. In addition to these effects on vascularization and the granulation layer, changes within the muscle layer were also seen with the PDGF encoding plasmid; an effect not seen in the control samples. This effect, at a distance from the implant, is important as it shows that tissues removed from the site of implant can be affected using the present gene-matrix delivery invention.

Figure 3B:
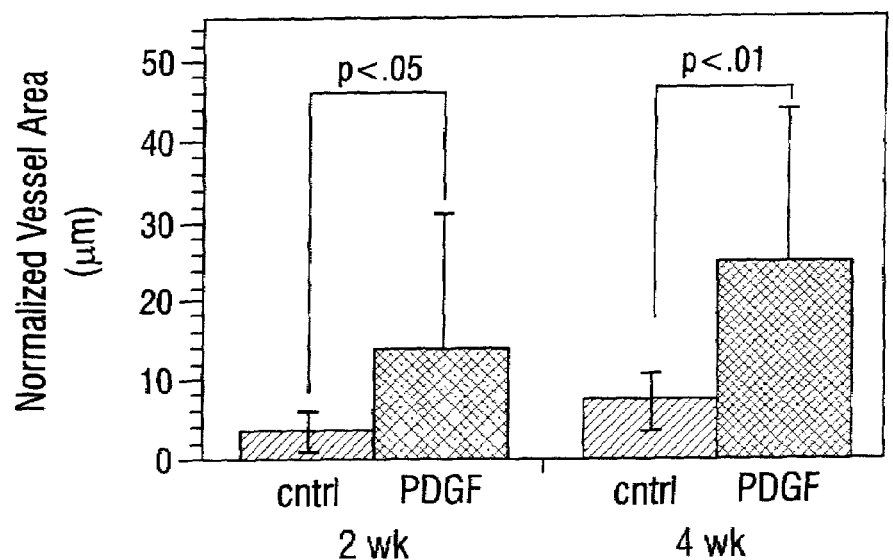
Figure 4:
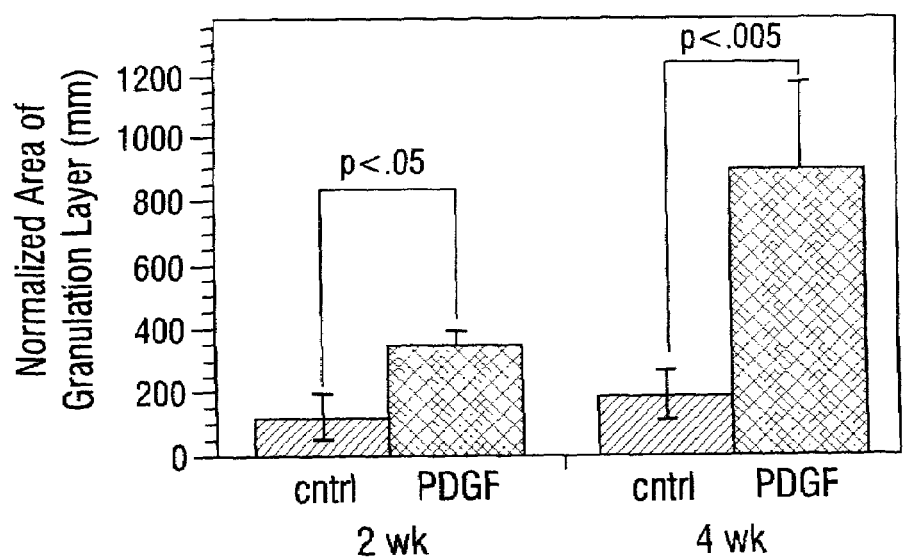
FIG. 4. DNA encoding PDGF released from a controlled pore PLGA polymer matrix stimulates granulation tissue growth in vivo. PLGA polymer matrices (75:25 (i.v.=0.2)) containing plasmid DNA encoding PDGF or a control (nuclear targeted β-galactosidase) were implanted subcutaneously into rats; samples were retrieved at 2 and 4 weeks and analyzed for granulation layer thickness. Granulation tissue thickness was normalized by the mean thickness obtained for delivery of the control plasmid (β-galactosidase) by the same delivery method. Values represent mean and standard deviations. Statistically significant increases are observed in the area of granulation layer stimulated by released PDGF relative to the β-galactosidase control at both 2 weeks ($p<0.05$) and 4 weeks. Statistical analysis was performed using the software program Instat.

Quantification of the samples at both 2 wk and 4 wk showed a statistically significant increase in the number and area of blood vessels (FIG. 3A and FIG. 3B) and the thickness of the granulation tissue (FIG. 4) for matrices releasing PDGF as compared to matrices releasing the control plasmid. At 2 weeks, the statistically significant difference had a value of $p<0.05$ for all three responses (FIG. 3A; FIG. 3B; FIG. 4).

Figure 5A:
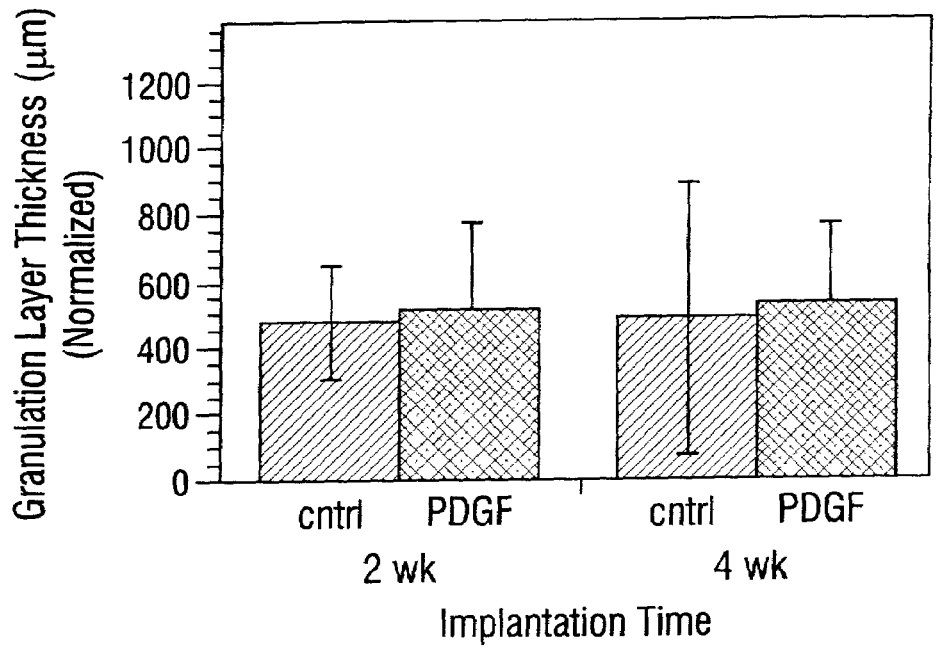
FIG. 5A and FIG. 5B. Injection of DNA encoding PDGF is unable to stimulate granulation tissue or blood vessel growth in vivo. Plasmid DNA encoding PDGF or a control (nuclear targeted β-galactosidase) was directly injected into rats; samples were retrieved at 2 and 4 weeks and analyzed for granulation layer thickness (FIG. 5A) and the number of blood vessels (FIG. 5B). Values represent mean and standard deviations.
Figure 5B:
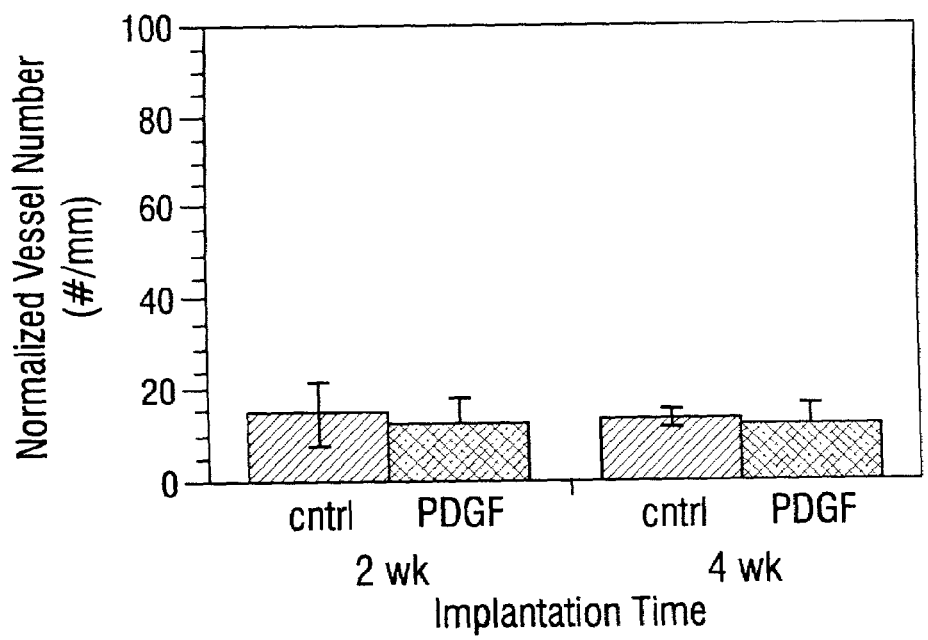

At 4 weeks, the statistically significant difference between control and PDGF encoding plasmid was even larger ($p<0.01$) (FIG. 5A, FIG. 5B and FIG. 6). The significant increases in the vessel number and granulation layer thickness from 2 wk to 4 wk in animals receiving PDGF-releasing polymer matrices is important as it indicates that the delivered gene continued to be expressed and had an increasing effect on tissue formation over time. Control DNA released from these matrices did not exhibit a significant increase between 2 and 4 wk for any of the parameters measured.

To confirm that the matrix-mediated delivery of the PDGF plasmid was responsible for the observed effects, PDGF-encoding plasmids were also directly injected into the subcutaneous pocket (400 μg of plasmid (the average quantity of plasmid incorporated into each matrix) in 100 μL). Histological sections obtained following direct plasmid injection showed no significant difference for PDGF delivery as compared to control. Quantification of the samples showed no significant effect on the thickness of the granulation tissue ($p>0.1$) (FIG. 5A) or the number of blood vessels ($p>0.1$) (FIG. 5B) with this method of plasmid delivery. These negative results are in accordance with the studies of Ledley (1996).

Example XVIII

Matrices Fabricated from Microspheres Incorporating DNA

In addition to Example XIII, controlled open pore matrices containing nucleic acids can also be fabricated by gas foaming/particulate leaching processes applied to polymer particles pre-loaded with nucleic acids. The present example represents one aspect of such processes, where nucleic acids are incorporated into microspheres of poly(lactide-co-glycolide) utilizing an atomization/extraction process operated at cryogenic temperatures. The three-dimensional matrix was then fabricated using a gas foaming/particulate leaching process. These approaches provide high incorporation efficiencies and sustained release of nucleic acids, which can be controlled in part through the microsphere fabrication process.

Plasmid DNA was incorporated into microspheres composed of poly(lactide-co-glycolide) (PLGA) using an atomization and extraction process operated at cryogenic temperatures. The plasmid was dissolved in a Hepes/Mannitol buffer for stability during the lyophilization process. The plasmid solution was passed through a nitrogen atomizer into a vessel containing liquid nitrogen and lyophilized. The lyophilized plasmid was next mixed with a solution of PLGA in chloroform. The plasmid in polymer mixture was mixed and passed through an atomizer into a vessel containing frozen ethanol overlaid with liquid nitrogen. The vessel was then placed at −80° C., allowing the microspheres to harden as the melting ethanol extracted the chloroform. Microspheres incorporating DNA were then isolated by filtering and dried in the lyophilizer.

Open pore matrices containing plasmid DNA were subsequently fabricated with a gas foaming/particulate leaching process. Microspheres incorporating DNA were mixed with sodium chloride, compressed into a disc, and placed in a pressure vessel with a high-pressure gas. Release of the pressure caused the polymer microspheres to expand. Collisions between adjacent microspheres cause them to fuse, thereby producing interconnected structural matrices. Pores were formed within the matrix by leaching out the salt, leaving a matrix with an open pore structure. In situations where an open pore structure is not desired, such as where cellular invasion is not necessary, a closed pore polymer structure can be generated and used, e.g., for sustained DNA delivery.

Figure 8:
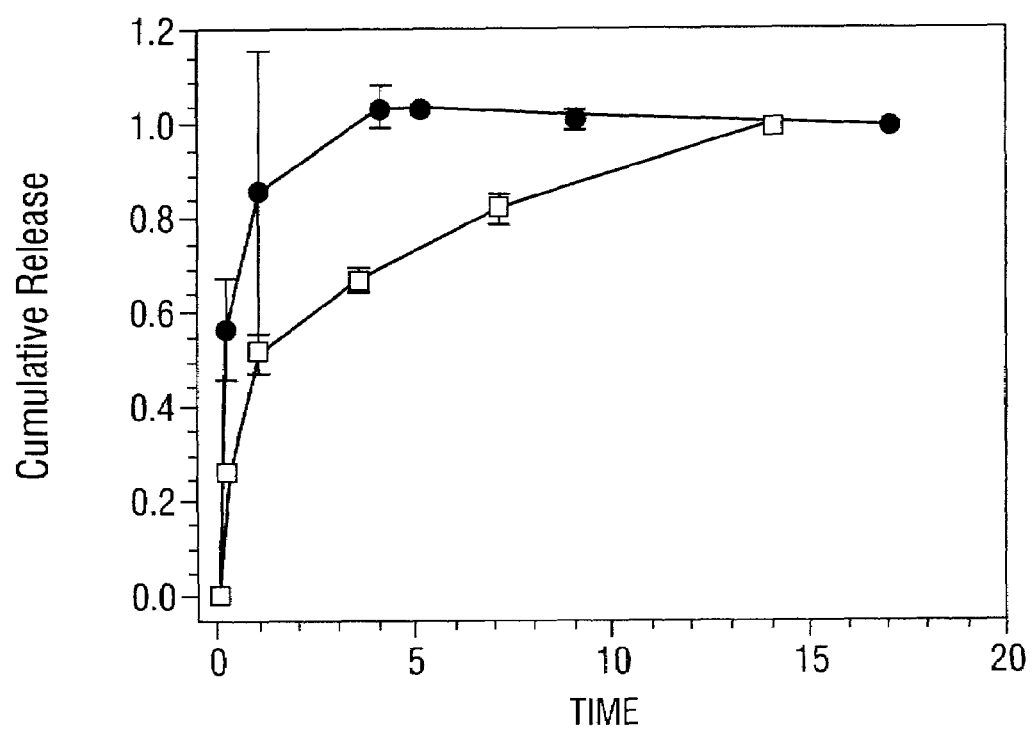
FIG. 8. Release kinetics of DNA from a biodegradable matrix of PLGA fabricated from microspheres pre-loaded with DNA (□; open square) or from a matrix fabricated by mixing the same PLGA polymer with DNA (●; closed circle).

Studies showed that plasmid DNA trapped within biodegradable matrices fabricated from pre-loaded microspheres is gradually released from the matrix. The release kinetics of DNA from various copolymers of poly(lactide-co-glycolide) for the microsphere-loaded foamed matrices are shown in FIG. 8. Release kinetics are also provided for matrices formed by the foaming of an admixture of lyophilized plasmid, polymer, and salt (as in the previous examples). The release kinetics are a function of the processing conditions.

FIG. 8 shows a sustained release of plasmid from the microsphere-loaded matrices for up to 14 days. Release from other foamed sponges of comparable composition but fabricated from a plasmid-polymer admixture occurred in less than 1 day. Gel electrophoresis was performed for the DNA released at different times from the matrices prepared from the microsphere-preloaded particles. At all times of release (0.16, 1, 3, 7, and 14 days), the DNA was not degraded, as evidenced by bands appearing on the gel at the appropriate locations.

Example XIX

Polysaccharide and Alginate Matrices

1. Modified Alginates

Each of U.S. Provisional Application Ser. No. 60/026,362, filed Sep. 19, 1996 the priority document for U.S. Pat. No. 6,642,363; U.S. Provisional Application Ser. No. 60/026,467, the priority document for U.S. Pat. No. 6,642,363, filed Sep. 19, 1996; U.S. Provisional Application Ser. No. 60/041,565, the priority document for U.S. Pat. No. 6,642,363, filed Mar. 21, 1997 and PCT Application Serial PCT/US97/16890, filed Sep. 19, 1997 (WO 98/12228) are specifically incorporated herein by reference without disclaimer for the purposes of describing the preparation and use of further unique polymeric materials and matrices thereof.

In particular, the foregoing applications, specifically incorporated herein by reference, teach the preparation and use of polysaccharides modified to bind biological agents covalently and also provide mechanisms for dissolution of the covalent bond to effect release of the biological agents of interest. Particularly disclosed are alginates modified so that they have controllable physical properties, such as sol-gel properties, and the like.

More particularly, the foregoing incorporated applications describe modified alginates that comprise at least one alginate chain section to which is bonded at least one molecule useful for cellular interaction. Preferred bonding mechanisms are those utilizing one or more uronic acid residues on the alginate chain section. As described in each of the foregoing applications, the biomolecules useful for cellular interaction are exemplified by cell adhesion molecules, cell attachment peptides, proteoglycan attachment peptide sequences, proteoglycans, and polysaccharides exhibiting cell adhesion. Particular examples are RGD peptides, fibronectin, vitronectin, Laminin A, Laminin B1, Laminin B2, collagen 1 or thrombospondin. Various polypeptide or peptide growth factors or enzymes may also be used as the cellular interacting molecules.

In certain embodiments, the alginate backbone of the modified alginate composition may comprise an oligomeric block unit of D-mannuronate, L-guluronate, or various combinations thereof. Alginates with naturally occurring alginate chain sections are also suitable for use in the modified alginate compositions.

In general, the alginate chain sections will have a molecular weight of about 30,000, about 50,000 or up to about 100,000 or more.

As described in each of the foregoing applications, specifically incorporated herein by reference, the modified alginate compositions are suitable for formulation into an injectable composition or solution for use as a cell transplantation matrix. All such matrices can be used in combination with genes or DNA to prepare the DNA-matrix formulations of the present invention. The modified alginate compositions form a network for viable cells to multiply, and are thus effective cell transplantation matrices. The modified alginate components of such matrices may be considered to be "hydrogels".

In certain embodiments, the modified alginates may contain at least one alginate chain section bonded to a polymeric backbone section and/or at least one alginate chain section cross-linked to another alginate chain section on the same or a different molecule. Thus, the polymers may comprise polymeric backbone sections and various side chains bonded to the backbone, optionally through a biological linker. Appropriate linkers are those involving amino acids, amino aldehydes, amino alcohols, or derivatized groups such as hydrazine, hydrazide, or semicarbazide. Appropriate backbone sections are therefore various natural and synthetic polymers, such as peptides and polypeptides, poly(vinyl alcohol), poly (ethylene oxide), and poly(uronic acid) in addition to the alginate-based polymers.

As described in each of the foregoing U.S. and PCT patent applications, each incorporated herein by reference, biodegradable linkers may be provided to form cleavable bonds between the backbone section and the side chain. Exemplary biodegradable bonds are those wherein a linker is bonded to the polymeric backbone section by an ester, imine, hydrozone or semicarbazone group.

Also provided by the foregoing incorporated applications are alginate materials that comprise alginate chains with covalently bonded cross-linking between the chains. This provides alginate material that is cross-linked to the extent such that it resumes essentially its original shape after compression. In certain aspects, the alginate material has sol-gel properties. The alginate material may additionally be gelled by the action of a divalent cation.

In the cross-linked, form-retaining alginate materials, the alginate chains may be cross-linked with a polyfunctional cross-linking agent having at least two functional groups that are covalently bonded to reactable groups within the alginate chains, such as carboxylic or uronic acid groups. These bifunctional cross-linking agents may therefore comprise at least two nitrogen-containing functional groups, as exemplified by containing at least two imine, hydroxide or semicarbazide functional groups, or combinations thereof. In certain embodiments, the cross-linking agents will be lysine or an alkyl ester thereof.

The flexible, cross-linked alginates can generally vary between forms in which 1-75 mole % of the carboxylic or uronic acid groups in the alginate chains are cross-linked. About 1, about 5, about 10, about 20, about 50 and about 75 mole % cross-linking provides useful polymers.

The various cross-linked alginate materials can thus be formulated in a viscous liquid form or in a swellable gel form. As mentioned above, these alginate materials may also be fabricated in non-swellable, compression-resistant forms having "shape memory properties". Any of these various alginate liquids, gels or shape-memory gels may also be bonded to other biomolecules, particularly any of the foregoing molecules useful for cellular interactions.

In the DNA-focused methods of the present invention, the genes or DNA may be linked to any one or more of the foregoing modified alginate compositions via a covalent bond, and preferably, via a biodegradable or releasable bond. Equally, as with any other structural matrix, genetic material may simply be physically and functionally associated with a matrix, and there is no particular requirement for covalent bonding.

2. Porous Alginate Hydrogels

U.S. Provisional Application Ser. No. 60/128,681, filed Apr. 9, 1999, now U.S. Pat. No. 6,511,650, is specifically incorporated herein by reference without disclaimer for the purposes of describing the preparation and use of further unique polymeric materials and matrices thereof. In particular, this application teaches the preparation and use of porous hydrogel materials formed by first creating gas pockets in the gel and then removing the gas to create a material with an open, interconnected pore structure that is maintained over extended time periods and has high mechanical integrity.

Two important aspects for the preparation of porous hydrogel materials are the gas bubble formation and subsequent stabilization. For embodiments using BSA surfactant and a bicarbonate gas-generating component, a certain ratio of BSA to bicarbonate solution is necessary to develop a foamy solution. Stabilization of the gas bubbles is dependent on the viscosity of the starting alginate solution and the concentration of BSA. A low viscosity solution cannot stabilize entrapped gas bubbles, while too high of a viscosity leads to a gel that is so strong that the gas bubbles cannot be readily removed during the vacuum step. In addition, the BSA serves to stabilize the gas bubbles in the alginate solution, and it is important to have the appropriate BSA concentration to enable formation of a stable foam containing gas bubbles.

Specifically, the following conditions resulted in the formation of open, interconnected porous hydrogels.

1. 3 w:w % alginate, 2.0M bicarbonate and 1.5% BSA were used as the starting solutions. 2 g of the alginate solution were mixed with 0.24 g of the BSA solution and 0.12 g of the bicarbonate solution to yield a foamy solution.
2. 3 w:w % alginate, 2.0M bicarbonate and 1.5% BSA were used as the starting solutions. 2 g of the alginate solution were mixed with 0.24 g of the BSA solution and 0.24 g of the bicarbonate solution to yield a foamy solution.
3. 4 w:w % alginate, 2.0M bicarbonate and 1.5% BSA were used as the starting solutions. 2 g of the alginate solution were mixed with 0.32 g of the BSA solution and 0.16 g of the bicarbonate solution to yield a foamy solution.
4. 4 w:w % alginate, 2.0M bicarbonate and 1.5% BSA were used as the starting solutions. 2 g of the alginate solution were mixed with 0.34 g of the BSA solution and 0.34 g of the bicarbonate solution to yield a foamy solution.
5. 5 w:w % alginate, 2.0M bicarbonate and 1.5% BSA were used as the starting solutions. 2 g of the alginate solution were mixed with 0.4 g of the BSA solution and 0.2 g of the bicarbonate solution to yield a foamy solution.
6. 5 w:w % alginate, 2.0M bicarbonate and 1.5% BSA were used as the starting solutions. 2 g of the alginate solution were mixed with 0.4 g of the BSA solution and 0.4 g of the bicarbonate solution to yield a foamy solution.
7. 5 w:w % alginate, 1.0M bicarbonate and 1.5% BSA were used as the starting solutions. 2 g of the alginate solution were mixed with 0.4 g of the BSA solution and 0.2 g of the bicarbonate solution to yield a foamy solution.

In sum, the following ranges of conditions were found preferable for forming interconnected pore structures by this embodiment:

Starting solutions of 3, 4 and 5 w:w % (weight % based on weight of water) alginate with 1.5% BSA and 1.0M to 2.0M bicarbonate solutions lead to the development of foamy solutions. The weight ratio of BSA to the bicarbonate is preferably from 2:1 to 1:1. Their amounts used depend on the concentration of the alginate solution.

Propylene glycol alginate was also used as a surfactant in order to replace the protein BSA. Equal amounts of alginate and propylene glycol alginate were dissolved in dd water to yield a 3% w:w solution. 2 g of this solution was mixed with 0.12 g of a bicarbonate solution to yield a foamy solution.

All other surfactants tested, such as Pluronics F108 and F68, yielded a foamy solution and led to stable interconnected porous hydrogels. Using 2 g of 8% w:w alginate and 0.12 g of 2.0M bicarbonate, 10% w:w solution of F108 yielded a foamy solution when added in amounts of 0.12 g and 0.06 g of the F108 solution, although use of 0.03 g of the F108 solution did not result in a stable and sufficient foamy solution.

Also, the composition of the gelling solution was modified. The 0.1 M $CaCl_2$ containing 10 vol % acetic acid of the prior art (Gotoh et al., 1993) did not lead a fast enough gelling of the alginate. The beads appeared sticky and beads tended to fuse together when in contact with other beads. The concentration of the $CaCl_2$ was raised to 0.5 M.

An indication of the porosity of the beads formed was obtained by observing beads suspended in an aqueous solution. Beads prior to exposure to vacuum appeared opaque and floated on the surface (indicating a low density as one would expect from the large amount of entrapped gas). Following exposure to vacuum, the beads appeared clear and sank to the bottom of the solution (indicating an increased density due to replacement of the gas with the more dense aqueous solution).

The porosity of beads formed was visually examined to confirm their porosity. Following isolation of beads from the gelling solution, a large number of gas bubbles could be observed within the alginate matrices. Following removal of the gas bubbles, an open porous structure was observed.

The interconnected pore structure of the matrices was assessed by seeding a solution of suspended cells onto porous alginate beads, and subsequently visualizing these cells using a MTT (3-(4,5-dimethylthiazol-2-yl-2,5-diphenyl tetrazolium bromide) assay. The porous beads took up cells, and the distribution of dyed cells allowed confirmation of the amount of interconnected pores in the matrix (large pores (greater than approximately 10 microns in diameter) were present).

To determine whether the pore structure remained stable over time, porous beads were allowed to remain in an aqueous solution for varying periods of time (1 day to 2 weeks) and subsequently analyzed for porosity by seeding cells. The incorporation and distribution of cells, and thus the matrix porosity, was unchanged following storage.

The pore structure remains intact in vivo, as shown by transplantation of porous alginate beads into subcutaneous pockets of rats. Invasion of macrophages and fibroblasts was noted throughout the matrices at one week, with more cells being present and greater new collagen deposition in the beads by the invading cells by two weeks. The beads maintained their original shape and dimensions, indicating that their mechanical properties were sufficient to withstand the compressional forces exerted in vivo.

The process to fabricate porous alginate matrices has been scaled up to allow large quantities of these materials to be produced. To incorporate air bubbles in large volumes of the initial solution, the solution is vigorously mixed in a high speed mixer (e.g., Sunbeam hand mixer, Model 2485). A syringe pump is used to generate large numbers of reproducibly sized beads in a semi-automatic fashion.

It is desirable for a variety of biomedical applications to prepare materials that are porous but also show degradation after implantation. As mammals do not carry the appropriate enzyme necessary to optimally degrade alginate at physiological conditions, the use of alginates with an average molecular weight low enough to allow the excretion of the material through the kidneys is an attractive alternative. This molecular weight is usually considered to lay around 50 kD.

Thus, the controlled degradation of alginates was performed to generate materials with a molecular weight below 50 kD, utilizing acid hydrolysis (solution), heat treatment (solution and bulk) and γ-irradiation (solution and bulk). Acid Hydrolysis: Alginate solutions (2% (w:w)) were refluxed in 0.3 M HCl for various times. Heat treatment: Alginate (solution and bulk) were autoclaved (1.034 bar, 121° C.) to generate alginate with lower average molecular weights. Samples were autoclaved for 1 h, 2 h and 2.5 h, respectively. γ-irradiation: Alginate could be degraded through gamma irradiation at a variety of conditions (irradiation of alginate solutions (2 and 3%) was first used). Based on its ease of use, gamma irradiation at 5.0 Mrad for 2.83 h was used to generate alginate fragments.

High molecular weight alginate could be broken down into lower molecular weight fragments using each of the above methods. Each method provided conditions resulting in alginates with molecular weights below 50 kD (as determined by GPC measurements). In addition, all alginate fragments still form gels in the presence of calcium ions.

Porous alginate beads were formed from alginate fragments. 8% w:w alginate, 2.0M bicarbonate and 1.5% BSA were used as the starting solutions. 2 g of the alginate solution were mixed with 0.24 g of the BSA solution and 0.12 g of the bicarbonate solution to yield a foamy solution.

The porosity of the beads formed from alginate fragments was confirmed by environmental scanning electron microscopy (ESEM). The interconnected pore structure of the alginate beads formed from alginate fragments ($M_N$=8920, $M_w$=16800) was assessed by cell seeding and MTT visualization. All beads showed a high degree of cell incorporation with a uniform cell distribution throughout the entire bead. The pore structure remained intact in vivo, as shown by transplantation into subcutaneous pockets of rats, when the porous beads maintained their original shape and dimensions and allowed cell invasion, indicating that their mechanical properties were sufficient to withstand the compressional forces exerted in vivo.

Example XX

DNA Release from DNA-Alginate Matrices

As generally described above, alginate hydrogels are biocompatible, have gentle gelling properties and can be delivered in a minimally invasive manner. Varying the type of alginate (e.g., ratio of mannuronic acid to guluronic acid) along with the fabrication process (e.g., source and amount of calcium, shape) allows control over the release kinetics.

Alginate matrices were fabricated generally as described in Example XIX. In particular, alginate hydrogel matrices containing plasmid DNA were fabricated by ionically crosslinking the gel with calcium. Alginate discs were prepared by mixing an alginate solution with plasmid DNA and a supersaturated solution of $CaSO_4$. The gel was cast between glass plates and allowed to gel. Discs were cut from the slab. Alginate beads were formed by dropping alginate/DNA mixtures into a bath of $CaCl_2$.

DNA release studies were performed by subsequently placing the alginate/DNA gels into a known volume of PBS buffer. The DNA released from the gel was quantified by measuring the concentration of DNA in the PBS solution over time using the Hoechst Dye binding assay.

Figure 6A:
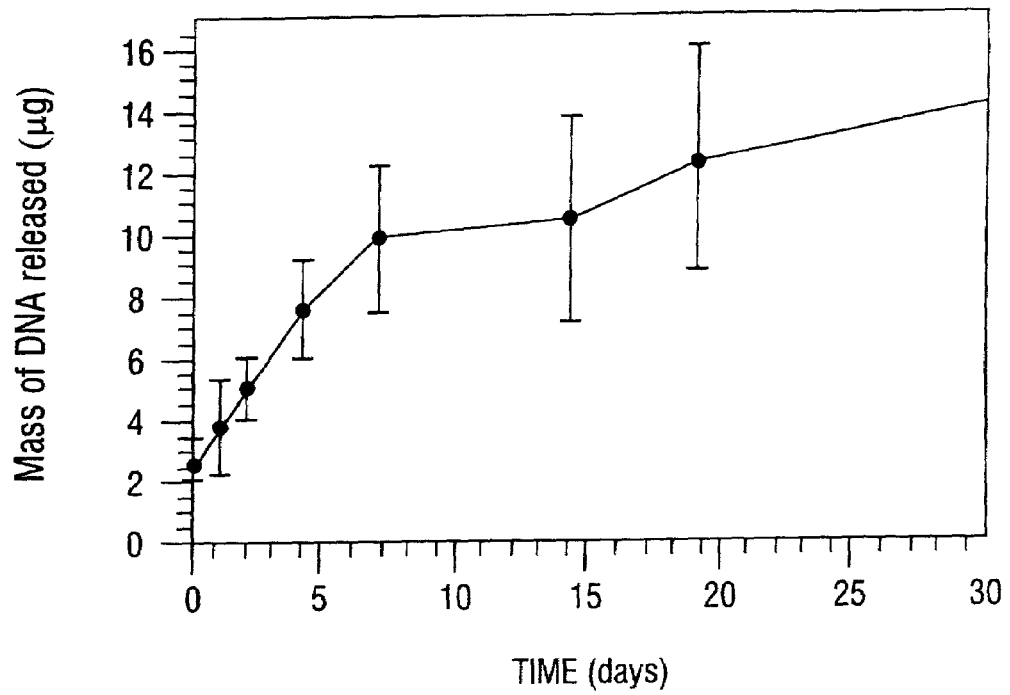
FIG. 6A and FIG. 6B. Release kinetics of DNA from discs of alginate hydrogels. Data are plotted as mass of DNA released (μg) versus time (days).
Figure 6B:
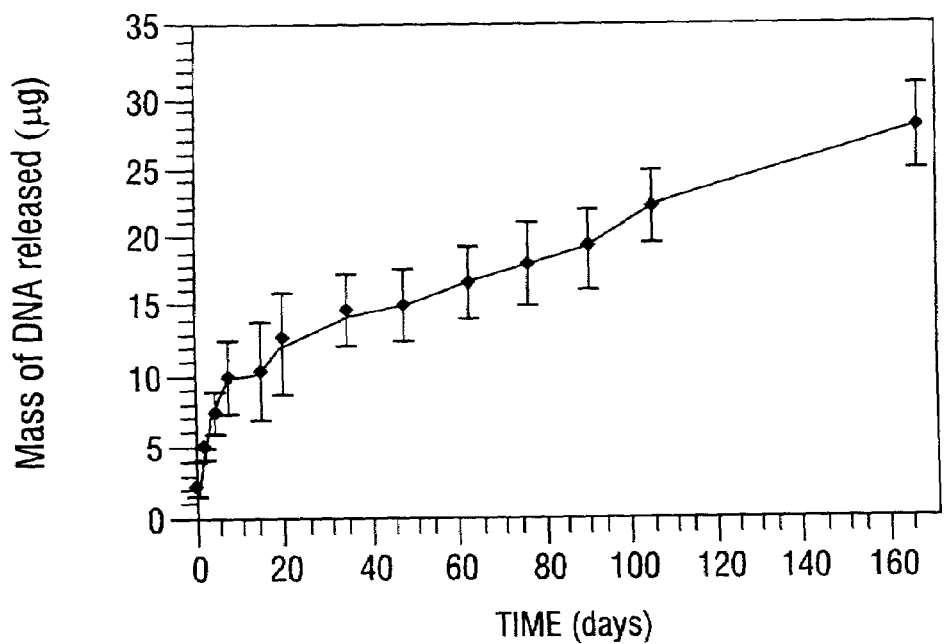

Continuous release of plasmid DNA (>160 days) from the alginate matrices has been demonstrated. FIG. 6A and FIG. 6B show the release kinetics of DNA from alginate hydrogel matrices, with FIG. 6A showing release of DNA for up to 30 days and FIG. 6B showing release of DNA for up to 160 days. Further, virtually all of the plasmid DNA released from beads of alginate is structurally intact when analyzed by electrophoresis.

All of the compositions, methods and apparatus disclosed and claimed herein can be made and executed without undue experimentation in light of the present disclosure. While the compositions, methods and apparatus of this invention have been described in terms of preferred embodiments, it will be apparent to those of skill in the art that variations may be applied to the compositions, methods and apparatus, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference without disclaimer.

Atala et al., *J. Urology*, 152:641-643, 1994.
Beck, Deguzman, Lee, Xu, McFatridge, Gillett, Amento, "TGF-beta 1 induces bone closure of skull defects", *J. Bone Miner. Res.*, 11:1257-65, 1991.
Boden, Joyce, Oliver, and Bolander, "Estrogen receptor mRNA expression in callus during fracture healing in the rat", *Calcif. Tissue Int.* 45:34-325, 1989.
Cavallaso, Kemp, Kraus, "Collagen Fabrics as Biomaterials," *Biotechnology and Bioengineering*, 43:781-791, 1994.
Chen, Bates, Dudley, Hammonds, and Amento, "Bone morphogenetic protein-2b stimulation of growth and osteogenic phenotypes in rat osteoblast-like cells: comparison with TGF-beta 1", *J. Bone Miner. Res.,* 6:1387-93, 1991.

Davidson, Allen, Kozarsky, Wilson, and Roessler, "A model system for in vivo gene transfer into the central nervous system using an adenoviral vector", *Nature Genetics* 3:219-223, 1993.

Deuel, "Growth factors," In: *Principles of Tissue Engineering*, R. P. Lanza, R. Langer, and W. L. Chick (eds.), Academic Press, San Diego, 1997.

Fang, Zhu, Smiley, Bonadio, Rouleau, Goldstein, McCauley, Davidson, Roessler, "Stimulation of new bone formation by direct transfer of osteogenic plasmid genes," *Proc. Nat. Acad. Sci.,* 93:5753-5758, 1996.

Gailet et al., *Curr. Opin. Cell. Biol.,* 6:717-725, 1994.

Ghosh-Choudhury, G. and Graham, F. L. *Biochem. Biophys. Res. Comm.,* 147:964-973, 1987.

Giannobile, "Periodontal tissue engineering by growth factors," *Bone,* 19(1S):23S-37S, 1996.

Gluzman, Y., Reichl, H., and Solnick, D. in: *Eukaryotic Viral Vectors* (Gluzman, Y., ed) pp. 187-192, Cold Spring Harbor Press, Cold Spring Harbor, N.Y., 1982.

Gotoh et al., *Cytotechnology,* 11:35, 1993.

Hanks C. T. et al., In: *Restorative Dental Materials*; Craig, R. G., ed., Ninth Edition, Mosby, 1993.

Harris, Kim, Mooney, "Open pore biodegradable matrices formed with gas foaming," *J. Biomed. Mat. Res.,* 42:396-402, 1998.

Hedley, Curley, Urban, "Microspheres containing plasmid-encoded antigens elicit cytotoxic T-cell responses," *Nature Medicine,* 4(3):365-368, 1998.

Hendy, Kronenberg, Potts, and Rich, "Nucleotide sequence of cloned cDNAs encoding human preproparathyroid hormone", *Proc. Natl. Acad. Sci. U.S.A.* 78:7365-7369, 1981.

Horowitz, Einhom, Philbrick, et al., "Functional and molecular changes in colony stimulating factor secretion by osteoblasts", *Connective Tissue Res.* 20:159-168, 1989.

Ishaug, Yaszemski, Biciog, Mikos, "Osteoblast Function on Synthetic Biodegradable Polymers", *J. Biomed. Mat. Res.,* 28:1445-1453, 1994.

Jingushi, Heydemann, Kana, Macey and Bolander, "Acidic fibroblast growth factor injection stimulates cartilage enlargement and inhibits cartilage gene expression in rat fracture healing", *J. Orthop. Res.* 8:364-371, 1990.

Jong, Jacob, Yip, Gardner, Seitelman, Whitney, Montgomery, Mathiowitz, *J. Cont. Rel.,* 47:123-134, 1997.

Karlsson, S., Van Doren, K., Schweiger, S. G., Nienhuis, A. W., and Gluzman, Y. *EMBO J.,* 5, 2377-2385, 1986.

Kim and Mooney, "Development of biocompatible synthetic extracellular matrices for tissue engineering," *Tr. Biotech,* 16:224-230, 1998.

Kyte & Doolittle, *J. Mol. Biol.* 157:105-132, 1982.

Labhasetwar, Bonadio, Goldstein, Chen, Levy, "A DNA controlled-release coating for gene transfer: transfection in skeletal and cardiac muscle," *J. Pharm. Sci.,* 87(11):1347-1350, 1998.

Langer, "New methods of drug delivery," *Science,* 249:1527-1533, 1992.

Langer, "Drug delivery and targeting," *Nature,* 392S:5-10, 1998.

Langer and Vacanti, "Tissue Engineering," *Science,* 260:920-926, 1993.

Ledley, "Pharmaceutical approach to somatic gene therapy," *Pharm. Res.,* 13(11):1595-1614, 1996.

Lo, Ponticiello, Leong, "Fabrication of controlled release biodegradable foams by phase separation," *Tissue Engineering,* 1:15-28, 1995.

Majmudar, Bole, Goldstein, Bonadio, "Bone cell culture in a three-dimensional polymer bead stabilizes the differentiated phenotype and provides evidence that osteoblastic cells synthesize type III collagen and fibronectin", *J. Bone and Min. Res.* 6:869-881, 1991.

Matthew et al., *Biomaterials,* 16:265-274, 1995.

McGrory, W. J., Bautista, D. S., and Graham, F. L. *Virol.,* 163, 614-617, 1988.

Mikos, Thorsen, Czerwonka, Bao, and Langer, "Preparation and characterization of poly(L-lactic acid) foams," *Polymer,* 35:1068-1077, 1994.

Mooney, Kaufmann, Sano, McNamara, Vacanti, Langer, "Transplantation of hepatocytes using porous biodegradable sponges," *Transplantation Proceedings,* 26:3425-3426, 1994.

Mooney and Langer, "Engineering biomaterials for tissue engineering: the 10-100 micron scale", In: Biomedical Engineering Handbook (Ed., Bronzino), CRC Press, 1609-1618, 1995.

Mooney, Park, Kaufmann, Sano, McNamara, Vacanti, Langer, "Biodegradable sponges for hepatocyte transplantation," *J. Biomed. Mat. Res.,* 29:959-965, 1995.

Mooney, Baldwin, Suh, Vacanti, Langer, "Novel approach to fabricate porous sponges of poly(D,L-lactic-co-glycolic acid) without the use of organic solvents," *Biomaterials,* 17:1417-1422, 1996.

Mooney, Kim, Vacanti, Langer and Atala, In: *Principles of Tissue Engineering*, Academic Press, 264, 1997.

Mooney, Sano, Kaufmann, Majahod, Schloo, Vacanti, Langer, "Long-term engraftment of hepatocytes transplanted on biodegradable polymer sponges," *J. Biomed Mater. Res.,* 37:413-420, 1997.

Nor, Christensen, Mooney, Polyerini, "VEGF enhances the survival of endothelial cells and sustains angiogenesis by inducing expression of Bcl-2," *Am. J. Pathol.,* 154:375-84, 1999.

Park, Baldwin, Sub, "Effect of the Pressure prop Rate on Cell Nucleation in Continuous Processing of Microcellular Polymers," *Polymer Engineering and Science,* 35,432-440, 1995.

Peters and Mooney, "Synthetic extracellular matrices to guide tissue formation," In: *Tissue Engineering for Therapeutic Use* 2, Y. Ikada and S. Enomoto (eds.), Elsevier, Amsterdam 1998.

Raines and Ross, "Platelet-derived growth factor in vivo," In: *Biology of Platelet-Derived Growth Factor,* B. Westermark and C. Sorg (eds.), Karger, Switzerland, 1993.

Raisz and Kream, "Regulation of bone formation", *N. Engl. J. Med.* 309:29-35, 1983.

Rosenfeld, M. A., Siegfried, W., Yoshimura, K., Yoneyama, K., Fukayama, M., Stier, L. E., Pääkkö, P. K., Gilardi, P., Stratford-Perricaudet, L. D., Perricaudet, M., Jallat, S., Pavirani, A., Lecocq, J.-P., and Crystal, R. G. *Science,* 252, 431-434, 1991.

Rosenfeld, M. A., Yoshimura, K., Trapnell, B. C., Yoneyama, K., Rosenthal, E. R., Dalemans, W., Fukayama, M., Bargon, J., Stier, L. E., Stratford-Perricaudet, L. D., Perricaudet, M., Guggino, W. B., Pavirani, A., Lecocq, J.-P., and Crystal, R. G. *Cell,* 68, 143-155, 1992.

Rothman, Kulik, Taubman, Berk, Smith, Nadal-Ginard, "Development and characterization of a cloned rat pulmonary arterial smooth muscle cell line that maintains differentiated properties through multiple subcultures," *Circulation,* 86:1977-1986, 1992.

Sampath and Reddi, "Dissociative extraction and reconstitution of extracellular matrix components involved in local bone differentiation", *Proc. Natl. Acad. Sci. U.S.A.* 78:7599-7603, 1981.

Shea et al., "Biodegradable Polymer Matrices in Dental Tissue Engineering," *In: Tissue Engineering: Fundamentals and Concepts*, Chapter 111.6, 1977.

Shea, Smiley, Bonadio and Mooney, "Controllable DNA delivery from three-dimensional polymer matrices", *Nature Biotech.*, 17:551-554, 1999.

Smidsrød et al., *TIBTECH*, 8:71-78, 1990.

Stein, Lian, Stein, Van Wijnen, Montecino, "Transcriptional control of osteoblast growth and differentiation," *Phys. Rev.*, 76(2):593-629, 1996.

Stratford-Perricaudet, Makeh, Perricaudet, and Birand, "Widespread long-term gene transfer to mouse skeletal muscles and heart", *J. Clin. Invest.* 90:626-630, 1992.

Stratford-Perricaudet, L. D., Levrero, M., Chasse, J.-F., Perricaudet, M., and Briand, P. *Hum. Gene Ther.*, 1, 241-256, 1992.

Thomsen, D. R., Stenberg, R. M., Goins, W. F., and Stinski, M. F. *Proc. Natl. Acad. Sci. USA,* 81, 659-663, 1984.

Wong, and Mooney, "Synthesis and properties of biodegradable polymers used as synthetic matrices for tissue engineering," *In: Synthetic Biodegradable Polymer Scaffolds*, A. Atala and D. J. Mooney (eds.), Birkhausen, Boston, 1997.

Yasko, Lane, Fellinger, Rosen, Wozney, and Wang, "The healing of segmental bone defects, induced by recombinant human bone morphogenetic protein (rhBMP-2). A radiographic, histological, and biomechanical study in rats". *J. Bone Joint Surg.,* 5:659-70, 1992.

What is claimed is:

1. A composition comprising at least a first nucleic acid segment in non-covalent association with a structural, porous modified alginate matrix, that comprises at least one alginate chain section modified by covalent bonding to at least one molecule that mediates cellular interactions.

2. The composition of claim 1, wherein at least a portion of said structural matrix is a modified alginate matrix that comprises at least one alginate chain section bonded to at least one molecule that mediates cellular interactions utilizing one or more uronic acid residues on said alginate chain section.

3. The composition of claim 1, wherein at least a portion of said structural matrix is a modified alginate matrix that comprises at least one alginate chain section bonded to at least one cellular interaction molecule selected from the group consisting of cell adhesion molecules, cell attachment peptides, proteoglycan attachment peptide sequences, proteoglycans, cell adhesion polysaccharides, growth factors and cell adhesion enzymes.

4. The composition of claim 3, wherein at least a portion of said structural matrix is a modified alginate matrix that comprises at least one alginate chain section bonded to at least one cellular interaction molecule selected from the group consisting of an RGR peptide, fibronectin, bitronectin, Laminin A, Laminin B1, Laminin B2, collagen 1 and thrombospondin.

5. The composition of claim 1, wherein at least a portion of said structural matrix is a modified alginate matrix prepared by a method comprising:

(a) providing a solution of a hydrogel-forming material and a surfactant;

(b) mixing said solution in the presence of a gas to form a stable foam;

(c) exposing said stable foam to conditions or agents that result in gelling of the hydrogel-forming material and in the generation of gas bubbles therein; and (d) exposing the hydrogel containing gas bubbles to a vacuum to release the gas and form the hydrogel material having macroporous open pore porosity.

6. The composition of claim 1, wherein at least a portion of said structural matrix is a modified alginate matrix prepared by a method comprising:

(a) providing a solution of a hydrogel-forming material, a surfactant and a gas-generating component, wherein said solution is capable of being mixed in the presence of a gas to incorporate the gas in the solution and form a stable foam;

(b) mixing said solution in the presence of a gas to form a stable foam;

(c) exposing said stable foam to conditions or agents that result in gelling of the hydrogel-forming material and to conditions or agents that result in generation of gas from the gas-generating component, to form a hydrogel containing gas bubbles therein; and (d) exposing said hydrogel containing gas bubbles therein to a vacuum to release the gas and to form the hydrogel material having macroporous open pore porosity.

7. A method for making a structural matrix-nucleic acid composition, comprising providing at least a first nucleic acid segment to a structural matrix, wherein at least a portion of said structural matrix is comprised of a porous polymer that contains pores formed by gas foaming and pores formed by leaching out of a particulate from the polymer.

8. The method of claim 7, comprising leaching out the particulate material from a composition comprising a gas foamed polymeric material, at least a first nucleic acid segment and a leachable particulate material.

9. The method of claim 8, comprising the steps of:

(a) preparing an admixture comprising at least a first nucleic acid segment, particles of a polymeric material capable of forming a gas foamed polymeric structure and a leachable particulate material;

(b) subjecting said admixture to a gas foaming process to create a porous polymeric structure that comprises said at least a first nucleic acid segment and said leachable particulate material; and (c) subjecting said porous polymeric structure to a leaching process that removes said leachable particulate material from said porous polymeric structure, thereby producing a polymeric structure of additional porosity that comprises said at least a first nucleic acid segment.

10. The method of claim 9, wherein said admixture is prepared by first incorporating said at least a first nucleic acid segment within said particles of a polymeric material and then admixing with said leachable particulate material.

11. The method of claim 10, wherein said admixture is prepared by first incorporating said at least a first nucleic acid segment within polymer beads or microspheres and then admixing with said leachable particulate material.

12. The method of claim 9, wherein the gas foaming process of step (b) comprises subjecting said admixture to an elevated pressure atmosphere of an inert gas in a manner effective to dissolve said gas into said polymeric material, and subjecting the gas-dissolved polymeric material to thermodynamic instability in a manner effective to cause nucleation and growth of gas pores sufficient to produce a continuous matrix of polymeric material that comprises said at least a first nucleic acid segment and said leachable particulate material.

13. The method of claim 12, wherein said thermodynamic instability is created by reducing said elevated pressure atmosphere.

14. The method of claim 9, wherein said leachable particulate material is a water-soluble leachable particulate material.

15. The method of claim 14, wherein said leachable particulate material is a salt, sugar or sugar alcohol.

16. The method of claim 15, wherein said leachable particulate material is NaCl, trehalose, glucose, sucrose or mannitol.

17. The method of claim 9, wherein said leaching process is conducted in vitro by contacting said porous polymeric material with a leaching agent.

18. The method of claim 9, wherein said leaching process is conducted in vivo by exposing said porous polymeric material to body fluids.

19. The composition of claim 1, wherein said nucleic acid segment is a DNA molecule, an antisense nucleic acid molecule or a ribozyme.

20. The composition of claim 1, wherein said nucleic acid segment is comprised within a plasmid or a recombinant expression vector.

21. The composition of claim 1, wherein said nucleic acid segment encodes a marker protein.

22. The composition of claim 1, wherein said nucleic acid segment encodes a protein or polypeptide that stimulates a bone progenitor cell when expressed in said cell.

23. The composition of claim 1, wherein said nucleic acid segment encodes a protein or polypeptide that stimulates a wound healing fibroblast, granulation tissue fibroblast or repair cell when expressed in said cell.

24. The composition of claim 1, wherein said nucleic acid segment encodes an antigenic or immunogenic protein or polypeptide that stimulates an immune response when expressed by an antigen presenting cell.

25. The composition of claim 1, wherein said nucleic acid segment encodes a cytotoxic or apoptosis-inducing protein or polypeptide that induces cell death upon expression in a cell.

26. The composition of claim 1, wherein said nucleic acid segment encodes a transcription or elongation factor, cell cycle control protein, kinase, phosphatase, DNA repair protein, oncogene, tumor suppressor, angiogenic protein, anti-angiogenic protein, immune response stimulating protein, cell surface receptor, accessory signaling molecule, transport protein, enzyme, anti-bacterial or anti-viral protein or polypeptide, hormone, neurotransmitter, growth factor, growth factor receptor, interferon, interleukin, chemokine, cytokine, colony stimulating factor or chemotactic factor protein or polypeptide.

27. The composition of claim 1, wherein said nucleic acid segment encodes a human protein or polypeptide.

28. The composition of claim 1, comprising at least a first and second nucleic acid segment.

29. The composition of claim 1, comprising a plurality of nucleic acid segments.

30. The composition of claim 1, further comprising a population of cells.

31. The composition of claim 30, wherein at least a portion of said nucleic acid segment is taken up by the cells comprised within said composition.

32. The composition of claim 26, wherein said nucleic acid segment encodes a growth hormone (GH) protein or polypeptide, a parathyroid hormone (PTH) protein or polypeptide, a PTHI-34 polypeptide or a bone morphogenetic protein (BMP) protein or polypeptide.

33. The composition of claim 32, wherein said nucleic acid segment encodes a BMP-2A, BMP-213, BMP-3, BMP-4, BMP-5, BMP-6, BMP-7 or BMP-8 protein or polypeptide.

34. The composition of claim 26, wherein said nucleic acid segment encodes a transforming growth factor-ut (TGF-a), TGF-PI or TGF-β2 protein or polypeptide, a latent TGFβ binding protein (LTBP) protein or polypeptide, an activin/inhibin protein or polypeptide, a fibroblast growth factor (FGF), a granulocyte/macrophage colony stimulating factor (GMCSF), an epidermal growth factor (EGF), a platelet derived growth factor (PDGF), an insulin-like growth factor (IGF) or a leukemia inhibitory factor (LIF).

* * * * *

UNITED STATES PATENT AND TRADEMARK OFFICE
CERTIFICATE OF CORRECTION

PATENT NO.         : 7,427,602 B1                                   Page 1 of 1
APPLICATION NO. : 09/442542
DATED              : September 23, 2008
INVENTOR(S)        : Jeffrey Bonadio et al.

It is certified that error appears in the above-identified patent and that said Letters Patent is hereby corrected as shown below:

On the Cover Page:

Item (*), add -- This patent is subject to a terminal disclaimer. --.

Item (60), add -- 60/085,305 (US) filed May 13, 1998 -- and -- 60/109,054 (US) filed May 12, 1999 --.

Item (60), add -- co-pending application 09/310,802 filed May 12, 1999 --.

Item (74), "Gernstein" should be -- Gerstein --.

At Column 80, line 29, "TGF-β2" should be -- TGF-P2 --.

At Column 80, line 29, "TGFβ" should be -- TGFP --.

Signed and Sealed this

Seventh Day of July, 2009

JOHN DOLL
*Acting Director of the United States Patent and Trademark Office*